US008143015B2

(12) United States Patent
Smith et al.

(10) Patent No.: US 8,143,015 B2
(45) Date of Patent: Mar. 27, 2012

(54) METHODS OF CLEAVING DNA WITH RATIONALLY-DESIGNED MEGANUCLEASES

(75) Inventors: James Jefferson Smith, Durham, NC (US); Derek Jantz, Durham, NC (US); Homme W. Hellinga, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/245,650

(22) Filed: Sep. 26, 2011

(65) Prior Publication Data
US 2012/0040405 A1    Feb. 16, 2012

Related U.S. Application Data

(63) Continuation of application No. 13/223,852, filed on Sep. 1, 2011, which is a continuation of application No. 11/583,368, filed on Oct. 18, 2006, now Pat. No. 8,021,867.

(60) Provisional application No. 60/727,512, filed on Oct. 18, 2005.

(51) Int. Cl.
*C12Q 1/34* (2006.01)
*C12Q 1/68* (2006.01)
*C07K 14/00* (2006.01)
*C12N 9/16* (2006.01)
*C12P 21/00* (2006.01)

(52) U.S. Cl. .......... 435/18; 435/6.1; 435/196; 435/69.1; 530/350

(58) Field of Classification Search .................. 435/6.1, 435/69.1, 400, 196, 320.1, 252.3, 325
See application file for complete search history.

(56) References Cited

U.S. PATENT DOCUMENTS

| | | | |
|---|---|---|---|
| 5,436,150 | A | 7/1995 | Chandrasegaran |
| 5,474,896 | A | 12/1995 | Dujon et al. |
| 5,789,215 | A | 8/1998 | Berns et al. |
| 5,792,632 | A | 8/1998 | Dujon et al. |
| 5,792,640 | A | 8/1998 | Chandrasegaran |
| 5,830,729 | A | 11/1998 | Jaisser et al. |
| 5,866,361 | A | 2/1999 | Dujon et al. |
| 5,948,678 | A | 9/1999 | Dujon et al. |
| 5,962,327 | A | 10/1999 | Dujon et al. |
| 6,238,924 | B1 | 5/2001 | Dujon et al. |
| 6,265,196 | B1 | 7/2001 | Chandrasegaran |
| 6,395,959 | B1 | 5/2002 | Dujon et al. |
| 6,566,579 | B1 | 5/2003 | Jaisser et al. |
| 6,610,545 | B2 | 8/2003 | Dujon et al. |
| 6,794,136 | B1 | 9/2004 | Eisenberg et al. |
| 6,822,137 | B1 | 11/2004 | Dujon et al. |
| 6,833,252 | B1 | 12/2004 | Dujon et al. |
| 7,214,536 | B2 | 5/2007 | Dujon et al. |
| 7,271,000 | B2 | 9/2007 | Dujon et al. |
| 7,309,605 | B1 | 12/2007 | Dujon et al. |
| 2002/0107214 | A1 | 8/2002 | Choulika et al. |
| 2002/0110898 | A1 | 8/2002 | Choulika et al. |
| 2003/0113887 | A1 | 6/2003 | Dujon et al. |
| 2003/0175968 | A1 | 9/2003 | Golic et al. |
| 2003/0182670 | A1 | 9/2003 | Dujon et al. |
| 2003/0229039 | A1 | 12/2003 | Choulika et al. |
| 2004/0002092 | A1 | 1/2004 | Arnould et al. |
| 2004/0019002 | A1 | 1/2004 | Choulika et al. |
| 2004/0068761 | A1 | 4/2004 | Golic et al. |
| 2004/0171154 | A1 | 9/2004 | Storici et al. |
| 2005/0026157 | A1 | 2/2005 | Baltimore et al. |
| 2005/0032223 | A1 | 2/2005 | Dujon et al. |
| 2005/0064474 | A1 | 3/2005 | Urnov et al. |
| 2005/0172365 | A1 | 8/2005 | Puchta et al. |
| 2005/0208489 | A1 | 9/2005 | Carroll et al. |
| 2006/0078552 | A1 | 4/2006 | Arnould et al. |
| 2006/0153826 | A1 | 7/2006 | Arnould et al. |
| 2006/0206949 | A1 | 9/2006 | Arnould et al. |
| 2006/0282914 | A1 | 12/2006 | D'Halluin et al. |

FOREIGN PATENT DOCUMENTS

| | | |
|---|---|---|
| EP | 1485475 | 12/2004 |
| WO | WO-96/14408 | 5/1996 |
| WO | WO-0046386 A3 | 8/2000 |
| WO | WO-03078619 A1 | 9/2003 |
| WO | WO-2004031346 A2 | 4/2004 |
| WO | WO-2004067736 A2 | 8/2004 |
| WO | WO-2004067753 A2 | 8/2004 |
| WO | WO-2005049842 A2 | 6/2005 |
| WO | 2007/049095 | * 10/2005 |
| WO | WO-2005105989 A1 | 11/2005 |
| WO | WO-2006097784 A1 | 9/2006 |
| WO | WO-2006097853 A1 | 9/2006 |
| WO | WO-2006097854 A1 | 9/2006 |
| WO | WO-2007034262 A1 | 3/2007 |
| WO | WO-2007049095 A1 | 5/2007 |
| WO | WO-2007049156 A2 | 5/2007 |
| WO | WO-2007057781 A3 | 5/2007 |
| WO | WO-2007060495 A1 | 5/2007 |
| WO | WO-2007093836 A1 | 8/2007 |

(Continued)

OTHER PUBLICATIONS

Phillips, A., J. Pharm. Pharmacology 53:1169-1174, 2001.*
Gardlik et al., Med. Sci. Monit. 11(4):RA110-121, 2005.*
Rosen et al., Nucleic Acids Research 34(17):4791-4800, published online Sep. 13, 2006.*
Adler, David A. et al. "Bioinformatics." *Encyclopedia of Life Sciences*. No month listed—2001. John Wiley & Sons Ltd. pp. 1-8.
Aggarwal et al., Novel site-specific DNA endonucleases, Structural Biology, 1998, pp. 19-25, vol. 8.
Argast et al., I-Ppol and I-Crel homing site sequence degeneracy determined by random mutagenesis and sequential in vitro enrichment, J. Mol. Biol., 1998, pp. 345-353, vol. 280.

(Continued)

*Primary Examiner* — Delia Ramirez
(74) *Attorney, Agent, or Firm* — Wilmer Cutler Pickering Hale and Dorr LLP

(57) ABSTRACT

Rationally-designed LAGLIDADG meganucleases and methods of making such meganucleases are provided. In addition, methods are provided for using the meganucleases to generate recombinant cells and organisms having a desired DNA sequence inserted into a limited number of loci within the genome, as well as methods of gene therapy, for treatment of pathogenic infections, and for in vitro applications in diagnostics and research.

25 Claims, 3 Drawing Sheets

FOREIGN PATENT DOCUMENTS

| WO | WO-2007093918 A2 | 8/2007 |
|---|---|---|
| WO | WO-2008010009 A1 | 1/2008 |
| WO | WO-2008010093 A2 | 1/2008 |

OTHER PUBLICATIONS

Arnould et al., Engineering of large numbers of highly specific homing endonucleases that induce recombination of novel DNA targets, J. Mol. Biol., 2006, pp. 443-458, vol. 355.
Ashworth et al. Jun. 2006. Computational redesign of endonucleases DNA binding and cleavage specificity. Nature, 441, 656-659.
Belfort et al., Homing enconucleases: keeping the house in order, Nucleic Acids Research, 1997, vol. 25, No. 17, pp. 3379-3388.
Beumer et al., Efficient gene targeting in *Drosophila* with zinc finger nucleases, Genetics, Feb. 1, 2006, pp. 1-48, 10.1534/genetics.105.052829.
Bibikova et al., Enhancing gene targeting with designed zinc finger nucleases, Science, May 2, 2003, p. 764, vol. 300.
Bibikova et al., Stimulation of homologous recombination through targeted cleavage by chimeric nucleases, Molecular and Cellular Biology, Jan. 2001, pp. 289-297, vol. 21 No. 1.
Bibikova et al., Targeted chromosomal cleavage and mutagenesis in *Drosophila* using zinc-finger nucleases, Genetics, Jul. 2002, pp. 1169-1175, vol. 161.
Bolduc et al. Revised Sep. 2003. Structural and biochemical analyses of DNA and RNA binding by a bifunctional homing endonuclease and group I intron splicing factor. Genes Dev, 17, 2875-2888.
Chames et al., In vivo selection of engineered homing endonucleases using double-strand break induced homologous recombination, Nucleic Acids Research, 2005, pp. 1-10, vol. 33 No. 20 e178.
Chen et al., A highly sensitive selection method for directed evolution of homing endonucleases, Nucleic Acids Research, 2005, pp. 1-7, vol. 33 No. 18 e154.
Chen, R. Jan. 1, 2001. Enzyme engineering: rational redesign versus directed evolution. Trends Biotechnol, 19, 13-14.
Chevalier B. S. et al. "Homing Endonucleases: Structural and Functional Insight Into the Catalysts if Intron/Intein Mobility." *Nucleic Acids Research*. Oxford University Press. Surrey, Great Britain. vol. 29, No. 18, Sep. 15, 2001. pp. 3757-3774.
Chevalier et al., Design, activity, and structure of a highly specific artificial endonuclease, Molecular Cell, Oct. 2002, pp. 895-905, vol. 10.
Chevalier et al., Flexible DNA target site recognition by divergent homing endoculease isoschizomers I-CreI and I-MsoI, J. Mol. Biol., 2003, pp. 253-269, vol. 329.
Chevalier et al., Metal-dependent DNA cleavage mechanism of the I-CreI LAGLIDADG homing endonuclease, Biochemistry, 2004, pp. 14015-14026, vol. 43.
Chevalier et al., The homing endonuclease I-CreI uses three metals, one of which is shared between the two active sites, Nature Structural Biology, Apr. 2001, pp. 312-316, vol. 8 No. 4.
Chilton et al., Targeted integration of T-DNA into the tobacco genome at double-stranded breaks: new insights on the mechanism of T-DNA integration, Plant Physiology, Nov. 2003, pp. 956-965, vol. 133.
Cozzone, Alain J. "Proteins: Fundamental Chemical Properties." *Encyclopedia of Life Sciences*. No month listed—2002. John Wiley & Sons Ltd. pp. 1-10.
Dalgaard, Jacob Z. et al. "A Site-Specific Endonuclease Encoded by a Typical Archaeal Intron." *Proc. Natl. Acad. Sci.* Jun. 1993. vol. 90. pp. 5414-5417.
DesJarlais et al., Use of a zinc-finger consensus sequence framework and specificity rules to design specific DNA binding proteins, Proc. Natl. Acad. Sci. USA, Mar. 1993, pp. 2256-2260, vol. 90.
Dhanasekaran et al., Designer zinc finger proteins: tools for creating artificial DNA-binding functional proteins, Acc. Chem. Res., 2006, pp. 45-52, vol., 30 No. 1.
Doyon et al., Directed evolution and substrate specificity profile of homing endonuclease I-SceI, J. Am. Chem. Soc., 2006, pp. 2477-2484, vol. 128.
Duan et al. May 16, 1997. Crystal structure of PI-SceI, a homing endonuclease with protein splicing activity. Cell, 89, 555-564.
Durai et al. Oct. 26, 2005. Zinc finger nucleases: custom-designed molecular scissors for genome engineering of plant and mammalian cells. Nucleic Acids Res, 33, 5978-5990.
Epinat et al., A novel engineered meganuclease induces homologous recombination in yeast and mammalian cells, Nucleic Acids Research, 2003, pp. 2952-2962, vol. 31 No. 11.
European Office Action, European Patent Application No. 06 826 293.0, dated Nov. 20, 2008 (3 pages).
European Search Report for European Patent Application No. 10191885.2 mailed Apr. 26, 2011. 12 pages.
European Search Report for European Patent Application No. 10191888.6 mailed May 18, 2011. 5 pages.
European Search Report for European Patent Application No. 10191904.1 mailed May 13, 2011. 9 pages.
Fitzsimons Hall et al., Creation of an artificial bifunctional intein by grafting a homing endonuclease into a mini-intein, J. Mol. Biol., 2002, pp. 173-179, vol. 323.
Gimble et al. Oct. 2003. Assessing the plasticity of DNA target site recognition of the PI-SceI homing endonuclease using a bacterial two-hybrid selection system. J Mol Biol, 334, 993-1008.
Gimble, F.S. Engineering Homing Endonulceases for Genomic Applications. In Homing Endonucleases and Inteins. Belfort, Derbyshire, Stoddard and Woods, Eds. Springer-Verlag, Berlin Heidelberg. 2005. 16 pages.
Grindl et al., The protein splicing domain of the homing endonuclease PI-SceI is responsible for specific DNA binding, Nucleic Acids Research, 1998, vol. 26, No. 8, pp. 1857-1862.
Guhan et al., Structural and functional characteristics of homing endonucleases, Critical Reviews in Biochemistry and Molecular Biology, 2003, pp. 199-248, vol. 38 No. 3.
Harris, J.L. and Craik, C.S. Engineering enzyme specificity. Curr Opin Chem Biol, 2, 127-132. No month listed—1998.
Heath, Patrick J. et al. "The Structure of I-CreI, A Group I Intron-encoded Homing Endonuclease." *Nature Structural Biology*. vol. 4, No. 6. Jun. 1997. pp. 468-476.
Hu et al. "Probing the Structure of the PI-SeeI-DNA Complex by Affinity Cleavage and Affinity Photcross-linking." *The Journal of Biological Chemistry*. Jan. 28, 2000. vol. 275, No. 4. pp. 2705-2712.
Ichiyanagi et al., Crystal structure of an archaeal intein-encoded homing endonuclease PI-PfuI, J. Mol. Biol., 2000, pp. 889-901, vol. 300.
Jurica et al., DNA recognication and cleavage by the LAGLIDADG homing endonuclease I-CreI, Molecular Cell, Oct. 1998, pp. 469-476, vol. 2.
Jurica, M.S. et al. "Homing Endonucleases: Structure, Function and Evolution." *CMLS: Cellular and Molecular Life Sciences*. Feb. 1999. vol. 55. pp. 1304-1326.
Liang et al. "Genetic Fusion of Subunits of a Dimeric Protein Substantially Enhances its Stability and Rate of Folding." *Proc. Natl. Acad. Sci.* vol. 90. Aug. 1993. pp. 7010-7014.
Lloyd et al., Targeted mutagenesis using zinc-finger nucleases in *Arabidopsis*, PNAS, Feb. 8, 2005, pp. 2232-2237, vol. 102 No. 6.
Looger, L. et al., Computational Design of Receptor and Sensor Proteins with Novel Functions, Nature, 2003, pp. 185-190, vol. 423 No. 6936.
Lucas et al., Rapid evolution of the DNA-binding site in LAGLIDADG homing endonucleases, Nucleic Acids Research, 2001, pp. 960-969, vol. 29 No. 4.
Maggert et al., Highly efficient sex chromosome interchanges produced by I-CreI expression in *Drosophila*, Genetics, Nov. 2005, pp. 1103-1114, vol. 171.
Mani et al., Binding of two zinc finger nuclease monomers to two specific sites is required for effective double-strand DNA cleavage, Biochemical and Biophysical Research Communications, 2005, pp. 1191-1197, vol. 334.
Mani et al., Design, engineering, and characterization of zinc finger nucleases, Biochemical and Biophysical Research Communications, 2005, pp. 447-457, vol. 335.
Matsumura et al. Feb. 21, 2006. Crystal structure of intein homing endonuclease II encoded in DNA polymerase gene from hyperthermophilic archaeon *Thermococcus kodakaraensis* strain KOD1. Proteins, 63, 711-715.

McDaniel et al., Advances in synthetic biology: on the path from prototypes to applications, Current Opinion in Biotechnology, 2005, pp. 476-483, vol. 16.

Monnat et al., Generation of highly site-specific DNA double-strand breaks in human cells by the homing endonucleases I-Ppol and I Crel, Biochemical and Biophysical Research Communications, 1999, pp. 88-93, vol. 255.

Moure et al. Sep. 2003. The crystal structure of the gene targeting homing endonuclease I-Scel reveals the origins of its target site specificity. J Mol Biol, 334, 685-695.

Moure et al., Crystal structure of the intein homing endonuclease PI-Scel bound to its recognition sequence, Nature Structural Biology, Oct. 2002, pp. 764-770, vol. 9 No. 10.

Moure, Carmen M. et al. "Crystal Structure of the Intein Homing Endonuclease PI-Scel Bound to its Recognition Sequence." Howard Hughes Medical Institute, Baylor College of Medicine, Houston Texas. Nature Publishing Group. Sep. 3, 2002. 7 pages.

Pabo et al., Transcription factors: structural families and principles of DNA recognition, Annu. Rev. Biochem., 1992, pp. 1053-1095, vol. 61.

Pace, C. Nick et al. "Protein Stability." *Encyclopedia of Life Sciences*. No month listed—2001. John Wiley & Sons Ltd. pp. 1-4.

Poland, Bradley W. et al. "Structural Insights into the Protein Splicing Mechanism of PI-Scel." *The Journal of Biological Chemistry*. Jun. 2000. vol. 275, No. 22. pp. 16408-16413.

Porteus et al., Gene targeting using zinc finger nucleases, Nature Biotechnology, Aug. 2005, pp. 967-973, vol. 23 No. 8.

Porteus, Mammalian gene targeting with designed zinc finger nucleases, Molecular Therapy, Feb. 2006, pp. 438-446, vol. 13 No. 2.

Puchta et al., Two different but related mechanisms are used in plants for the repair of genomic double-strand breaks by homologous recombination, Proc. Natl. Acad. Sci. USA, May 1996, pp. 5055-5060, vol. 93.

Rong et al., Targeted mutagenesis by homologous recombination in *D. melanogaster*, Genes & Dev., 2002, pp. 1568-1581, vol. 16.

Rosen et al. Sep. 13, 2006. Homing endonuclease I-Crel derivatives with novel DNA target specificities. Nucleic Acids Res, 34, 4791-4800.

Rouet et al., Introduction of double-strand breaks into the genome of mouse cells by expression of a rare-cutting endonuclease, Molecular and Cellular Biology, Dec. 1994, pp. 8096-8106, vol. 14 No. 12.

Sali, Andrej et al. "Comparative Protein Modelling by Satisfaction of Spatial Restraints." *J. Mol. Biol.* Jul. 1993. pp. 779-815.

Seligman et al., Genetic Analysis of the *Chlamydomonas reinhardtii* I-Crel mobile intron homing system in *Escherichia coli*, Genetics, Dec. 1997, pp. 1653-1664, vol. 147.

Seligman et al., Mutations altering the cleavage specificity of a homing endonuclease, Nucleic Acids Research, 2002, pp. 3870-3879, vol. 30 No. 17.

Shen et al. Jul. 2004. DNA binding and cleavage by the HNH homing endonuclease I-Hmul. J Mol Biol, 342, 43-56.

Silva et al., Analysis of the LAGLIDADG interface of the monomeric homing endonuclease I-Dmol, Nucleic Acids Research, 2004, pp. 3156-3168, vol. 32 No. 10.

Silva et al., Crystal structure of the thermostable archaeal intron-encoded endonuclease I-Dmol, J. Mol. Biol., 1999, pp. 1123-1136, vol. 286.

Silva, George H. et al. "From Monomeric to Homodimeric Endonucleases and Back: Engineering Novel Specificity of LAGLIDADG Enzymes." *J. Mol. Biol.* Jul. 2006. pp. 744-754.

Smith et al., A combinatorial approach to create artificial homing endonucleases cleaving chosen sequences, Nucleic Acids Research, vol. 00, No. 00, Nov. 27, 2006, pp. 1-12.

Smith et al., A detailed study of the substrate specificity of a chimeric restriction enzyme, Nucleic Acids Research, 1999, pp. 674-681, vol. 27 No. 2.

Smith et al., Requirements for double-strand cleavage by chimeric restriction enzymes with zinc finger DNA-recognition domains, Nucleic Acids Research, 2000, pp. 3361-3369, vol. 28 No. 17.

Spiegel et al., The structure of I-Ceul homing endonuclease: evolving asymmetric DNA recognition from a symmetric protein scaffold, Structure, May 2006, pp. 869-880, vol. 14.

Stoddard, Homing endonuclease structure and function, Quarterly Reviews of Biophysics, 2005, pp. 1-47.

Sussman et al., Isolation and characterization of new homing endonuclease specificities at individual target site positions, J. Mol. Biol., 2004, pp. 31-41, vol. 342.

Turmel, Monique et al. "Evolutionary Conserved and Functionally Important Residues in the I-Ceul Homing Endonuclease." *Nucleic Acid Research.* Apr. 1997. vol. 25, No. 13. pp. 2610-2619.

Tzfira et al., Towards targeted mutagenesis and gene replacement in plants, Trends in Biotechnology, Dec. 2005, pp. 567-569, vol. 23 No. 12.

Urnov et al., Designed transcription factors as structural, functional and therapeutic probes of chromatin in vivo, EMBO Reports, 2002, pp. 610-615, vol. 3 No. 7.

Urnov et al., Highly efficient endogenous human gene correction using designed zinc-finger nucleases, Nature, Jun. 2, 2005, pp. 646-651, vol. 435.

Wang et al., Purification, biochemical characterization and protein-DNA interactions of the I-Crel endonuclease produced in *Escherichia coli*, Nucleic Acids Research, 1997, pp. 3767-3776, vol. 25 No. 19.

Werner, Erik et al. "High Resolution Crystal Structure of Domain I of the *Saccharomyces cerevisiae* Homing Endonuclease PI-Scel." *Nucelic Acid Research*. Jul. 2002. vol. 30, No. 18. pp. 3962-3971.

Wright et al., High-frequency homologous recombination in plants mediated by zinc-finger nucleases, The Plant Journal, 2005, pp. 693-705, vol. 44.

Gouble et al. "Efficient in toto Targeted Recombination in Mouse Liver by Meganuclease-induced Double-strand Break." The Journal of Gene Medicine. Feb. 13, 2006. Wiley Interscience. vol. 8. p. 616-622.

* cited by examiner

| | |
|---|---|
| WT | CAAACTGTCGTGAGACAGTTTG |
| CF1/CF2 | GAAAATATCATTGGTGTTTCCT |
| MYD1/MYD2 | GACCTCGTCCTCCGACTCGCTG |
| CCR1/CCR2 | AACCCTCTCCAGTGAGATGCCT |
| ACH1/ACH2 | CTGGGAGTCTCAGGACAGCCTG |
| TAT1/TAT2 | GAAGAGCTCATCAGAACAGTCA |
| HSV1/HSV2 | CTCGATGTCGGACGACACGGCA |
| LAM1/LAM2 | TGCGGTGTCCGGCGACAGCCTG |
| POX1/POX2 | AAAACTGTCAAATGACATCGCA |
| URA1/URA2 | TTAGATGACAAGGGAGACGCAT |
| GLA1/GLA2 | CACTAACTCGTATGAGTCGGTG |
| BRP1/BRP2 | TGCCTCCTCTAGAGACCCGGAG |

B

| Enzyme → Site ↓ | WT | CF | MYD | CCR | ACH | TAT | HSV | LAM | POX | URA | GLA | BRP | |
|---|---|---|---|---|---|---|---|---|---|---|---|---|---|
| WT | 100 | 0 | 0 | 0 | 0 | 0 | 47 | 0 | 100 | 100 | 0 | 0 | Wild type |
| CF1/CF2 | 0 | 63 | 0 | 0 | 0 | 0 | 0 | 0 | 0 | 0 | 0 | 0 | Cystic Fibrosis |
| MYD1/MYD2 | 0 | 0 | 94 | 0 | 0 | 0 | 16 | 0 | 0 | 0 | 0 | 0 | Myotonic Dystrophy |
| CCR1/CCR2 | 0 | 0 | 0 | 100 | 0 | 0 | 0 | 0 | 0 | 0 | 0 | 0 | CCR5 |
| ACH1/ACH2 | 0 | 0 | 0 | 0 | 87 | 0 | 0 | 0 | 0 | 0 | 0 | 0 | Achondroplasia |
| TAT1/TAT2 | 0 | 0 | 0 | 0 | 0 | 81 | 0 | 0 | 0 | 0 | 0 | 0 | HIV-1 |
| HSV1/HSV2 | 0 | 0 | 0 | 0 | 0 | 0 | 67 | 0 | 0 | 0 | 0 | 0 | Herpes Simplex 1 |
| LAM1/LAM2 | 0 | 0 | 0 | 0 | 0 | 0 | 0 | 87 | 0 | 0 | 0 | 0 | Lambda Phage |
| POX1/POX2 | 100 | 0 | 0 | 0 | 0 | 0 | 0 | 0 | 100 | 0 | 0 | 0 | Variola Virus |
| URA1/URA2 | 0 | 0 | 0 | 0 | 0 | 0 | 0 | 0 | 0 | 70 | 0 | 0 | S. cerevisiae URA3 |
| GLA1/GLA2 | 0 | 0 | 0 | 0 | 0 | 0 | 0 | 0 | 0 | 0 | 88 | 0 | A. thaliana GL2 |
| BRP1/BRP2 | 0 | 0 | 0 | 0 | 0 | 0 | 0 | 0 | 0 | 0 | 0 | 100 | A. thaliana BP1 | ent applica-

SEQUENCE LISTING

<160> NUMBER OF SEQ ID NOS: 37

<210> SEQ ID NO 1
<211> LENGTH: 163
<212> TYPE: PRT
<213> ORGANISM: Chlamydomonas reinhardtii

<400> SEQUENCE: 1

Met Asn Thr Lys Tyr Asn Lys Glu Phe Leu Leu Tyr Leu Ala Gly Phe
1               5                   10                  15

```
Val Asp Gly Asp Gly Ser Ile Ile Ala Gln Ile Lys Pro Asn Gln Ser
            20                  25                  30

Tyr Lys Phe Lys His Gln Leu Ser Leu Ala Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro

<210> SEQ ID NO 2
<211> LENGTH: 22
<212> TYPE: DNA
<213> ORGANISM: Chlamydomonas reinhardtii

<400> SEQUENCE: 2
gaaactgtct cacgacgttt tg                                           22

<210> SEQ ID NO 3
<211> LENGTH: 22
<212> TYPE: DNA
<213> ORGANISM: Chlamydomonas reinhardtii

<400> SEQUENCE: 3
caaaacgtcg tgagacagtt tc                                           22

<210> SEQ ID NO 4
<211> LENGTH: 22
<212> TYPE: DNA
<213> ORGANISM: Chlamydomonas reinhardtii

<400> SEQUENCE: 4
caaactgtcg tgagacagtt tg                                           22

<210> SEQ ID NO 5
<211> LENGTH: 22
<212> TYPE: DNA
<213> ORGANISM: Chlamydomonas reinhardtii

<400> SEQUENCE: 5
caaactgtct cacgacagtt tg                                           22

<210> SEQ ID NO 6
<211> LENGTH: 170
<212> TYPE: PRT
<213> ORGANISM: Monomastix sp.

<400> SEQUENCE: 6

Met Thr Thr Lys Asn Thr Leu Gln Pro Thr Glu Ala Ala Tyr Ile Ala
1               5                   10                  15
```

-continued

```
Gly Phe Leu Asp Gly Asp Gly Ser Ile Tyr Ala Lys Leu Ile Pro Arg
                20                  25                  30

Pro Asp Tyr Lys Asp Ile Lys Tyr Gln Val Ser Leu Ala Ile Ser Phe
            35                  40                  45

Ile Gln Arg Lys Asp Lys Phe Pro Tyr Leu Gln Asp Ile Tyr Asp Gln
 50                  55                  60

Leu Gly Lys Arg Gly Asn Leu Arg Lys Asp Arg Gly Asp Gly Ile Ala
 65                  70                  75                  80

Asp Tyr Thr Ile Ile Gly Ser Thr His Leu Ser Ile Ile Leu Pro Asp
                85                  90                  95

Leu Val Pro Tyr Leu Arg Ile Lys Lys Gln Ala Asn Arg Ile Leu
            100                 105                 110

His Ile Ile Asn Leu Tyr Pro Gln Ala Gln Lys Asn Pro Ser Lys Phe
            115                 120                 125

Leu Asp Leu Val Lys Ile Val Asp Asp Val Gln Asn Leu Asn Lys Arg
130                 135                 140

Ala Asp Glu Leu Lys Ser Thr Asn Tyr Asp Arg Leu Leu Glu Glu Phe
145                 150                 155                 160

Leu Lys Ala Gly Lys Ile Glu Ser Ser Pro
                165                 170

<210> SEQ ID NO 7
<211> LENGTH: 22
<212> TYPE: DNA
<213> ORGANISM: Monomastix sp.

<400> SEQUENCE: 7
cagaacgtcg tgagacagtt cc                                              22

<210> SEQ ID NO 8
<211> LENGTH: 22
<212> TYPE: DNA
<213> ORGANISM: Monomastix sp.

<400> SEQUENCE: 8
ggaactgtct cacgacgttc tg                                              22

<210> SEQ ID NO 9
<211> LENGTH: 235
<212> TYPE: PRT
<213> ORGANISM: Saccharomyces cerevisiae

<400> SEQUENCE: 9

Met Lys Asn Ile Lys Lys Asn Gln Val Met Asn Leu Gly Pro Asn Ser
 1               5                  10                  15

Lys Leu Leu Lys Glu Tyr Lys Ser Gln Leu Ile Glu Leu Asn Ile Glu
                20                  25                  30

Gln Phe Glu Ala Gly Ile Gly Leu Ile Leu Gly Asp Ala Tyr Ile Arg
            35                  40                  45

Ser Arg Asp Glu Gly Lys Thr Tyr Cys Met Gln Phe Glu Trp Lys Asn
 50                  55                  60

Lys Ala Tyr Met Asp His Val Cys Leu Leu Tyr Asp Gln Trp Val Leu
 65                  70                  75                  80

Ser Pro Pro His Lys Lys Glu Arg Val Asn His Leu Gly Asn Leu Val
                85                  90                  95

Ile Thr Trp Gly Ala Gln Thr Phe Lys His Gln Ala Phe Asn Lys Leu
                100                 105                 110
```

```
Ala Asn Leu Phe Ile Val Asn Lys Lys Thr Ile Pro Asn Asn Leu
        115                 120                 125

Val Glu Asn Tyr Leu Thr Pro Met Ser Leu Ala Tyr Trp Phe Met Asp
130                 135                 140

Asp Gly Gly Lys Trp Asp Tyr Asn Lys Asn Ser Thr Asn Lys Ser Ile
145                 150                 155                 160

Val Leu Asn Thr Gln Ser Phe Thr Phe Glu Glu Val Glu Tyr Leu Val
                165                 170                 175

Lys Gly Leu Arg Asn Lys Phe Gln Leu Asn Cys Tyr Val Lys Ile Asn
            180                 185                 190

Lys Asn Lys Pro Ile Ile Tyr Ile Asp Ser Met Ser Tyr Leu Ile Phe
        195                 200                 205

Tyr Asn Leu Ile Lys Pro Tyr Leu Ile Pro Gln Met Met Tyr Lys Leu
210                 215                 220

Pro Asn Thr Ile Ser Ser Glu Thr Phe Leu Lys
225                 230                 235
```

<210> SEQ ID NO 10
<211> LENGTH: 18
<212> TYPE: DNA
<213> ORGANISM: Saccharomyces cerevisiae

<400> SEQUENCE: 10
ttaccctgtt atccctag                                                 18

<210> SEQ ID NO 11
<211> LENGTH: 18
<212> TYPE: DNA
<213> ORGANISM: Saccharomyces cerevisiae

<400> SEQUENCE: 11
ctagggataa cagggtaa                                                 18

<210> SEQ ID NO 12
<211> LENGTH: 218
<212> TYPE: PRT
<213> ORGANISM: Chlamydomonas eugametos

<400> SEQUENCE: 12

```
Met Ser Asn Phe Ile Leu Lys Pro Gly Glu Lys Leu Pro Gln Asp Lys
1               5                   10                  15

Leu Glu Glu Leu Lys Lys Ile Asn Asp Ala Val Lys Lys Thr Lys Asn
            20                  25                  30

Phe Ser Lys Tyr Leu Ile Asp Leu Arg Lys Leu Phe Gln Ile Asp Glu
        35                  40                  45

Val Gln Val Thr Ser Glu Ser Lys Leu Phe Leu Ala Gly Phe Leu Glu
    50                  55                  60

Gly Glu Ala Ser Leu Asn Ile Ser Thr Lys Lys Leu Ala Thr Ser Lys
65                  70                  75                  80

Phe Gly Leu Val Val Asp Pro Glu Phe Asn Val Thr Gln His Val Asn
                85                  90                  95

Gly Val Lys Val Leu Tyr Leu Ala Leu Glu Val Phe Lys Thr Gly Arg
            100                 105                 110

Ile Arg His Lys Ser Gly Ser Asn Ala Thr Leu Val Leu Thr Ile Asp
        115                 120                 125

Asn Arg Gln Ser Leu Glu Glu Lys Val Ile Pro Phe Tyr Glu Gln Tyr
130                 135                 140

Val Val Ala Phe Ser Ser Pro Glu Lys Val Lys Arg Val Ala Asn Phe
```

```
                145                 150                 155                 160
Lys Ala Leu Leu Glu Leu Phe Asn Asn Asp Ala His Gln Asp Leu Glu
                165                 170                 175

Gln Leu Val Asn Lys Ile Leu Pro Ile Trp Asp Gln Met Arg Lys Gln
        180                 185                 190

Gln Gly Gln Ser Asn Glu Gly Phe Pro Asn Leu Glu Ala Ala Gln Asp
    195                 200                 205

Phe Ala Arg Asn Tyr Lys Lys Gly Ile Lys
        210                 215

<210> SEQ ID NO 13
<211> LENGTH: 22
<212> TYPE: DNA
<213> ORGANISM: Chlamydomonas eugametos

<400> SEQUENCE: 13
ataacggtcc taaggtagcg aa                                              22

<210> SEQ ID NO 14
<211> LENGTH: 22
<212> TYPE: DNA
<213> ORGANISM: Chlamydomonas eugametos

<400> SEQUENCE: 14
ttcgctacct taggaccgtt at                                              22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gaagagctca tcagaacagt ca                                              22

<210> SEQ ID NO 16
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16 gaagagctc                                                              9

<210> SEQ ID NO 17
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17 tgactgttc                                                              9

<210> SEQ ID NO 18
<211> LENGTH: 9
<212> TYPE: DNA
<213> ORGANISM: Artificial Sequence
<220> FEATURE:
<223> OTHER INFORMATION: Description of Artificial Sequence: Synthetic
```

```
                        oligonucleotide

<400> SEQUENCE: 18 aaccctctc                                                                  9

<210> SEQ ID NO 19
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19 ctccgggtc                                                                  9

<210> SEQ ID NO 20
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20 tgcggtgtc                                                                  9

<210> SEQ ID NO 21
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21 caggctgtc                                                                  9

<210> SEQ ID NO 22
<211> LENGTH: 22
<212> TYPE: DNA
<213> ORGANISM: Bacteriophage lamda-p05

<400> SEQUENCE: 22
tgcggtgtcc ggcgacagcc tg                                                  22

<210> SEQ ID NO 23
<211> LENGTH: 22
<212> TYPE: DNA
<213> ORGANISM: Homo sapiens

<400> SEQUENCE: 23
ctgggagtct caggacagcc tg                                                  22

<210> SEQ ID NO 24
<211> LENGTH: 22
<212> TYPE: DNA
<213> ORGANISM: Homo sapiens

<400> SEQUENCE: 24
ccaggtgtct ctggactcct cc                                                  22

<210> SEQ ID NO 25
<211> LENGTH: 22
<212> TYPE: DNA
<213> ORGANISM: Homo sapiens
```

```
<400> SEQUENCE: 25
gaaaatatca ttggtgtttc ct                                              22

<210> SEQ ID NO 26
<211> LENGTH: 22
<212> TYPE: DNA
<213> ORGANISM: Homo sapiens

<400> SEQUENCE: 26
aaccctctcc agtgagatgc ct                                              22

<210> SEQ ID NO 27
<211> LENGTH: 22
<212> TYPE: DNA
<213> ORGANISM: Homo sapiens

<400> SEQUENCE: 27
gacctcgtcc tccgactcgc tg                                              22

<210> SEQ ID NO 28
<211> LENGTH: 22
<212> TYPE: DNA
<213> ORGANISM: Herpes Simplex Virus 2

<400> SEQUENCE: 28
ctcgatgtcg gacgacacgg ca                                              22

<210> SEQ ID NO 29
<211> LENGTH: 22
<212> TYPE: DNA
<213> ORGANISM: Bacillus anthracis

<400> SEQUENCE: 29
acaagtgtct atggacagtt ta                                              22

<210> SEQ ID NO 30
<211> LENGTH: 22
<212> TYPE: DNA
<213> ORGANISM: Variola virus

<400> SEQUENCE: 30
aaaactgtca aatgacatcg ca                                              22

<210> SEQ ID NO 31
<211> LENGTH: 22
<212> TYPE: DNA
<213> ORGANISM: Epstein-Barr Virus

<400> SEQUENCE: 31
cggggtctcg tgcgaggcct cc                                              22

<210> SEQ ID NO 32
<211> LENGTH: 22
<212> TYPE: DNA
<213> ORGANISM: Arabidopsis thaliana

<400> SEQUENCE: 32
cactaactcg tatgagtcgg tg                                              22

<210> SEQ ID NO 33
<211> LENGTH: 22
<212> TYPE: DNA
<213> ORGANISM: Arabidopsis thaliana
```

```
<400> SEQUENCE: 33
tgcctcctct agagacccgg ag                                              22

<210> SEQ ID NO 34
<211> LENGTH: 22
<212> TYPE: DNA
<213> ORGANISM: Nicotiana tabacum

<400> SEQUENCE: 34
taaaatctct aaggtctgtg ca                                              22

<210> SEQ ID NO 35
<211> LENGTH: 22
<212> TYPE: DNA
<213> ORGANISM: Nicotiana tabacum

<400> SEQUENCE: 35
caagaattca agcgagcatt aa                                              22

<210> SEQ ID NO 36
<211> LENGTH: 22
<212> TYPE: DNA
<213> ORGANISM: Saccharomyces cerevisiae

<400> SEQUENCE: 36
ttagatgaca agggagacgc at                                              22

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 37

Leu Ala Gly Leu Ile Asp Ala Asp Gly
 1               5
```

METHODS OF CLEAVING DNA WITH RATIONALLY-DESIGNED MEGANUCLEASES

RELATED APPLICATION

This application is a continuation of U.S. patent application Ser. No. 13/223,852, filed Sep. 1, 2011, which is a continuation of U.S. patent application Ser. No. 11/583,368, filed Oct. 18, 2006, now U.S. Pat. No. 8,021,867, which claimed benefit of priority to U.S. Provisional Patent Application No. 60/727,512, filed Oct. 18, 2005, the entire disclosure of which is hereby incorporated by reference.

GOVERNMENT SUPPORT

The invention was supported in part by grants 2R01-GM-0498712, 5F32-GM072322 and 5 DP1 OD000122 from the National Institute of General Medical Sciences of National Institutes of Health of the United States of America. Therefore, the U.S. government may have certain rights in the invention.

FIELD OF THE INVENTION

The invention relates to the field of molecular biology and recombinant nucleic acid technology. In particular, the invention relates to rationally-designed, non-naturally-occurring meganucleases with altered DNA recognition sequence specificity and/or altered affinity. The invention also relates to methods of producing such meganucleases, and methods of producing recombinant nucleic acids and organisms using such meganucleases.

BACKGROUND OF THE INVENTION

Genome engineering requires the ability to insert, delete, substitute and otherwise manipulate specific genetic sequences within a genome, and has numerous therapeutic and biotechnological applications. The development of effective means for genome modification remains a major goal in gene therapy, agrotechnology, and synthetic biology (Porteus et al. (2005), Nat. Biotechnol. 23: 967-73; Tzfira et al. (2005), Trends Biotechnol. 23: 567-9; McDaniel et al. (2005), Curr. Opin. Biotechnol. 16: 476-83). A common method for inserting or modifying a DNA sequence involves introducing a transgenic DNA sequence flanked by sequences homologous to the genomic target and selecting or screening for a successful homologous recombination event. Recombination with the transgenic DNA occurs rarely but can be stimulated by a double-stranded break in the genomic DNA at the target site. Numerous methods have been employed to create DNA double-stranded breaks, including irradiation and chemical treatments. Although these methods efficiently stimulate recombination, the double-stranded breaks are randomly dispersed in the genome, which can be highly mutagenic and toxic. At present, the inability to target gene modifications to unique sites within a chromosomal background is a major impediment to successful genome engineering.

One approach to achieving this goal is stimulating homologous recombination at a double-stranded break in a target locus using a nuclease with specificity for a sequence that is sufficiently large to be present at only a single site within the genome (see, e.g., Porteus et al. (2005), Nat. Biotechnol. 23: 967-73). The effectiveness of this strategy has been demonstrated in a variety of organisms using chimeric fusions between an engineered zinc finger DNA-binding domain and the non-specific nuclease domain of the FokI restriction enzyme (Porteus (2006), Mol Ther 13: 438-46; Wright et al. (2005), Plant J. 44: 693-705; Urnov et al. (2005), Nature 435: 646-51). Although these artificial zinc finger nucleases stimulate site-specific recombination, they retain residual non-specific cleavage activity resulting from under-regulation of the nuclease domain and frequently cleave at unintended sites (Smith et al. (2000), Nucleic Acids Res. 28: 3361-9). Such unintended cleavage can cause mutations and toxicity in the treated organism (Porteus et al. (2005), Nat. Biotechnol. 23: 967-73).

A group of naturally-occurring nucleases which recognize 15-40 base-pair cleavage sites commonly found in the genomes of plants and fungi may provide a less toxic genome engineering alternative. Such "meganucleases" or "homing endonucleases" are frequently associated with parasitic DNA elements, such as group 1 self-splicing introns and inteins. They naturally promote homologous recombination or gene insertion at specific locations in the host genome by producing a double-stranded break in the chromosome, which recruits the cellular DNA-repair machinery (Stoddard (2006), Q. Rev. Biophys. 38: 49-95). Meganucleases are commonly grouped into four families: the LAGLIDADG family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif (see Chevalier et al. (2001), Nucleic Acids Res. 29(18): 3757-3774). The LAGLIDADG meganucleases with a single copy of the LAGLIDADG motif form homodimers, whereas members with two copies of the LAGLIDADG motif are found as monomers. Similarly, the GIY-YIG family members have a GIY-YIG module, which is 70-100 residues long and includes four or five conserved sequence motifs with four invariant residues, two of which are required for activity (see Van Roey et al. (2002), Nature Struct. Biol. 9: 806-811). The His-Cys box meganucleases are characterized by a highly conserved series of histidines and cysteines over a region encompassing several hundred amino acid residues (see Chevalier et al. (2001), Nucleic Acids Res. 29(18): 3757-3774). In the case of the NHN family, the members are defined by motifs containing two pairs of conserved histidines surrounded by asparagine residues (see Chevalier et al. (2001), Nucleic Acids Res. 29(18): 3757-3774). The four families of meganucleases are widely separated from one another with respect to conserved structural elements and, consequently, DNA recognition sequence specificity and catalytic activity.

Natural meganucleases, primarily from the LAGLIDADG family, have been used to effectively promote site-specific genome modification in plants, yeast, Drosophila, mammalian cells and mice, but this approach has been limited to the modification of either homologous genes that conserve the meganuclease recognition sequence (Monnat et al. (1999), Biochem. Biophys. Res. Commun. 255: 88-93) or to pre-engineered genomes into which a recognition sequence has been introduced (Rouet et al. (1994), Mol. Cell. Biol. 14: 8096-106; Chilton et al. (2003), Plant Physiol. 133: 956-65; Puchta et al. (1996), Proc. Natl. Acad. Sci. USA 93: 5055-60; Rong et al. (2002), Genes Dev. 16: 1568-81; Gouble et al. (2006), J. Gene Med. 8(5):616-622).

Systematic implementation of nuclease-stimulated gene modification requires the use of engineered enzymes with customized specificities to target DNA breaks to existing sites in a genome and, therefore, there has been great interest in adapting meganucleases to promote gene modifications at medically or biotechnologically relevant sites (Porteus et al. (2005), *Nat. Biotechnol.* 23: 967-73; Sussman et al. (2004), *J. Mol. Biol.* 342: 31-41; Epinat et al. (2003), *Nucleic Acids Res.* 31: 2952-62).

The meganuclease I-CreI from *Chlamydomonas reinhardtii* is a member of the LAGLIDADG family which recognizes and cuts a 22 base-pair recognition sequence in the chloroplast chromosome, and which presents an attractive target for meganuclease redesign. The wild-type enzyme is a homodimer in which each monomer makes direct contacts with 9 base pairs in the full-length recognition sequence. Genetic selection techniques have been used to identify mutations in I-CreI that alter base preference at a single position in this recognition sequence (Sussman et al. (2004), *J. Mol. Biol.* 342: 31-41; Chames et al. (2005), *Nucleic Acids Res.* 33: e178; Seligman et al. (2002), *Nucleic Acids Res.* 30: 3870-9) or, more recently, at three positions in the recognition sequence (Arnould et al. (2006), *J. Mol. Biol.* 355: 443-58). The I-CreI protein-DNA interface contains nine amino acids that contact the DNA bases directly and at least an additional five positions that can form potential contacts in modified interfaces. The size of this interface imposes a combinatorial complexity that is unlikely to be sampled adequately in sequence libraries constructed to select for enzymes with drastically altered cleavage sites.

There remains a need for nucleases that will facilitate precise modification of a genome. In addition, there remains a need for techniques for generating nucleases with pre-determined, rationally-designed recognition sequences that will allow manipulation of genetic sequences at specific genetic loci and for techniques utilizing such nucleases to genetically engineer organisms with precise sequence modifications.

SUMMARY OF THE INVENTION

The present invention is based, in part, upon the identification and characterization of specific amino acid residues in the LAGLIDADG family of meganucleases that make contacts with DNA bases and the DNA backbone when the meganucleases associate with a double-stranded DNA recognition sequence, and thereby affect the specificity and activity of the enzymes. This discovery has been used, as described in detail below, to identify amino acid substitutions which can alter the recognition sequence specificity and/or DNA-binding affinity of the meganucleases, and to rationally design and develop meganucleases that can recognize a desired DNA sequence that naturally-occurring meganucleases do not recognize. The invention also provides methods that use such meganucleases to produce recombinant nucleic acids and organisms by utilizing the meganucleases to cause recombination of a desired genetic sequence at a limited number of loci within the genome of the organism, for gene therapy, for treatment of pathogenic infections, and for in vitro applications in diagnostics and research.

Thus, in some embodiments, the invention provides recombinant meganucleases having altered specificity for at least one recognition sequence half-site relative to a wild-type I-CreI meganuclease, in which the meganuclease includes a polypeptide having at least 85% sequence similarity to residues 2-153 of the wild-type I-CreI meganuclease of SEQ ID NO: 1, but in which the recombinant meganuclease has specificity for a recognition sequence half-site which differs by at least one base pair from a half-site within an I-CreI meganuclease recognition sequence selected from SEQ ID NO: 2, SEQ ID NO: 3, SEQ ID NO: 4 and SEQ ID NO: 5, and in which the recombinant meganuclease includes at least one modification listed in Table 1 which is not an excluded modification found in the prior art.

In other embodiments, the invention provides recombinant meganucleases having altered specificity for at least one recognition sequence half-site relative to a wild-type I-MsoI meganuclease, in which the meganuclease includes a polypeptide having at least 85% sequence similarity to residues 6-160 of the I-MsoI meganuclease of SEQ ID NO: 6, but in which the recombinant meganuclease has specificity for a recognition sequence half-site which differs by at least one base pair from a half-site within an I-MsoI meganuclease recognition sequence selected from SEQ ID NO: 7 and SEQ ID NO: 8, and in which the recombinant meganuclease includes at least one modification listed in Table 2 which is not an excluded modification found in the prior art.

In other embodiments, the invention provides recombinant meganucleases having altered specificity for a recognition sequence relative to a wild-type I-SceI meganuclease, in which the meganuclease includes a polypeptide having at least 85% sequence similarity to residues 3-186 of the I-SceI meganuclease of SEQ ID NO: 9, but in which the recombinant meganuclease has specificity for a recognition sequence which differs by at least one base pair from an I-SceI meganuclease recognition sequence of SEQ ID NO: 10 and SEQ ID NO: 11, and in which the recombinant meganuclease includes at least one modification listed in Table 3 which is not an excluded modification found in the prior art.

In other embodiments, the invention provides recombinant meganucleases having altered specificity for at least one recognition sequence half-site relative to a wild-type I-CeuI meganuclease, in which the meganuclease includes a polypeptide having at least 85% sequence similarity to residues 5-211 of the I-CeuI meganuclease of SEQ ID NO: 12, but in which the recombinant meganuclease has specificity for a recognition sequence half-site which differs by at least one base pair from a half-site within an I-CeuI meganuclease recognition sequence selected from SEQ ID NO: 13 and SEQ ID NO: 14, and in which the recombinant meganuclease includes at least one modification listed in Table 4 which is not an excluded modification found in the prior art.

The meganucleases of the invention can include one, two, three or more of the modifications which have been disclosed herein in order to affect the sequence specificity of the recombinant meganucleases at one, two, three or more positions within the recognition sequence. The meganucleases can include only the novel modifications disclosed herein, or can include the novel modifications disclosed herein in combination with modifications found in the prior art. Specifically excluded, however, are recombinant meganucleases comprising only the modifications of the prior art.

In another aspect, the invention provides for recombinant meganucleases with altered binding affinity for double-stranded DNA which is not sequence-specific. This is accomplished by modifications of the meganuclease residues which make contacts with the backbone of the double-stranded DNA recognition sequence. The modifications can increase or decrease the binding affinity and, consequently, can increase or decrease the overall activity of the enzyme. Moreover, increases/decreases in binding and activity have been found to causes decreases/increases in sequence specificity. Thus, the invention provides a means for altering sequence specificity generally by altering DNA-binding affinity.

Thus, in some embodiments, the invention provides for recombinant meganucleases having altered binding affinity for double-stranded DNA relative to a wild-type I-CreI meganuclease, in which the meganuclease includes a polypeptide having at least 85% sequence similarity to residues 2-153 of the I-CreI meganuclease of SEQ ID NO: 1, and in which the DNA-binding affinity has been either (1) increased by at least one modification corresponding to a substitution selected from (a) substitution of E80, D137, I81, L112, P29, V64 or Y66 with H, N, Q, S, T, K or R, or (b) substitution of T46, T140 or T143 with K or R; or, conversely, (2) decreased by at least one modification corresponding to a substitution selected from (a) substitution of K34, K48, R51, K82, K116 or K139 with H, N, Q, S, T, D or E, or (b) substitution of I81, L112, P29, V64, Y66, T46, T140 or T143 with D or E.

In other embodiments, the invention provides for recombinant meganucleases having altered binding affinity for double-stranded DNA relative to a wild-type I-MsoI meganuclease, in which the meganuclease includes a polypeptide having at least 85% sequence similarity to residues 6-160 of the I-MsoI meganuclease of SEQ ID NO: 6, and in which the DNA-binding affinity has been either (1) increased by at least one modification corresponding to a substitution selected from (a) substitution of E147, I85, G86 or Y118 with H, N, Q, S, T, K or R, or (b) substitution of Q41, N70, S87, T88, H89, Q122, Q139, S150 or N152 with K or R; or, conversely, (2) decreased by at least one modification corresponding to a substitution selected from (a) substitution of K36, R51, K123, K143 or R144 with H, N, Q, S, T, D or E, or (b) substitution of I85, G86, Y118, Q41, N70, S87, T88, H89, Q122, Q139, S150 or N152 with D or E.

In other embodiments, the invention provides for recombinant meganucleases having altered binding affinity for double-stranded DNA relative to a wild-type I-SceI meganuclease, in which the meganuclease includes a polypeptide having at least 85% sequence similarity to residues 3-186 of the I-SceI meganuclease of SEQ ID NO: 9, and in which the DNA-binding affinity has been either (1) increased by at least one modification corresponding to a substitution selected from (a) substitution of D201, L19, L80, L92, Y151, Y188, I191, Y199 or Y222 with H, N, Q, S, T, K or R, or (b) substitution of N15, N17, S81, H84, N94, N120, T156, N157, S159, N163, Q165, S166, N194 or 5202 with K or R; or, conversely, (2) decreased by at least one modification corresponding to a substitution selected from (a) substitution of K20, K23, K63, K122, K148, K153, K190, K193, K195 or K223 with H, N, Q, S, T, D or E, or (b) substitution of L19, L80, L92, Y151, Y188, I191, Y199, Y222, N15, N17, S81, H84, N94, N120, T156, N157, S159, N163, Q165, S166, N194 or 5202 with D or E.

In other embodiments, the invention provides for recombinant meganucleases having altered binding affinity for double-stranded DNA relative to a wild-type I-CeuI meganuclease, in which the meganuclease includes a polypeptide having at least 85% sequence similarity to residues 5-211 of the I-CeuI meganuclease of SEQ ID NO: 12, and in which the DNA-binding affinity has been either (1) increased by at least one modification corresponding to a substitution selected from (a) substitution of D25 or D128 with H, N, Q, S, T, K or R, or (b) substitution of S68, N70, H94, S117, N120, N129 or H172 with K or R; or, conversely, (2) decreased by at least one modification corresponding to a substitution selected from (a) substitution of K21, K28, K31, R112, R114 or R130 with H, N, Q, S, T, D or E, or (b) substitution of S68, N70, H94, S117, N120, N129 or H172 with D or E.

The meganucleases of the invention can include one, two, three or more of the modifications of backbone contact residues which have been disclosed herein in order to affect DNA-binding affinity. In addition, these modifications affecting DNA-binding affinity can be combined with one or more of the novel modifications of the base contact residues described above which alter the sequence specificity of the recombinant meganucleases at specific positions within the recognition sequence, or with the prior art modifications described above, or with a combination of the novel modifications and prior art modifications. In particular, by combining backbone contact modifications and base contact modifications, recombinant meganucleases can be rationally-designed with desired specificity and activity. For example, increases in DNA-binding affinity can be designed which may offset losses in affinity resulting from designed changes to base contact residues, or decreases in affinity can be designed which may also decrease sequence specificity and broaden the set of recognition sequences for an enzyme.

In another aspect, the invention provides for rationally-designed meganuclease monomers with altered affinity for homo- or heterodimer formation. The affinity for dimer formation can be measured with the same monomer (i.e., homodimer formation) or with a different monomer (i.e., heterodimer formation) such as a reference wild-type meganuclease. These recombinant meganucleases have modifications to the amino acid residues which are present at the protein-protein interface between monomers in a meganuclease dimer. The modifications can be used to promote heterodimer formation and create meganucleases with non-palindromic recognition sequences.

Thus, in some embodiments, the invention provides recombinant meganuclease monomers having altered affinity for dimer formation with a reference meganuclease monomer, in which the recombinant monomer includes a polypeptide having at least 85% sequence similarity to residues 2-153 of the I-CreI meganuclease of SEQ ID NO: 1, but in which affinity for dimer formation has been altered by at least one modification corresponding to a substitution selected from (a) substitution of K7, K57 or K96 with D or E, or (b) substitution of E8 or E61 with K or R. Based upon such recombinant monomers, the invention also provides recombinant meganuclease heterodimers including (1) a first polypeptide having at least 85% sequence similarity to residues 2-153 of the I-CreI meganuclease of SEQ ID NO: 1, but in which affinity for dimer formation has been altered by at least one modification corresponding to a substitution selected from (a) substitution of K7, K57 or K96 with D or E, and (2) a second polypeptide having at least 85% sequence similarity to residues 2-153 of the I-CreI meganuclease of SEQ ID NO: 1, but i which affinity for dimer formation has been altered by at least one modification corresponding to a substitution selected from (b) substitution of E8 or E61 with K or R.

In other embodiments, the invention provides recombinant meganuclease monomers having altered affinity for dimer formation with a reference meganuclease monomer, in which the recombinant monomer includes a polypeptide having at least 85% sequence similarity to residues 6-160 of the I-MsoI meganuclease of SEQ ID NO: 6, but in which affinity for dimer formation has been altered by at least one modification corresponding to a substitution selected from (a) substitution of R302 with D or E, or (b) substitution of D20, E11 or Q64 with K or R. Based upon such recombinant monomers, the invention also provides recombinant meganuclease heterodimers including (1) a first polypeptide having at least 85% sequence similarity to residues 6-160 of the I-MsoI meganuclease of SEQ ID NO: 6, but in which affinity for dimer formation has been altered by at least one modification corresponding to a substitution selected from (a) substitution of R302 with D or E, and (2) a second polypeptide having at least 85% sequence similarity to residues 6-160 of the I-MsoI meganuclease of SEQ ID NO: 6, but in which affinity for dimer formation has been altered by at least one modification corresponding to a substitution selected from (b) substitution of D20, E11 or Q64 with K or R.

In other embodiments, the invention provides recombinant meganuclease monomers having altered affinity for dimer formation with a reference meganuclease monomer, in which the recombinant monomer includes a polypeptide having at least 85% sequence similarity to residues 5-211 of the I-CeuI meganuclease of SEQ ID NO: 12, but in which affinity for dimer formation has been altered by at least one modification corresponding to a substitution selected from (a) substitution of R93 with D or E, or (b) substitution of E152 with K or R. Based upon such recombinant monomers, the invention also provides recombinant meganuclease heterodimers including (1) a first polypeptide having at least 85% sequence similarity to residues 5-211 of the I-CeuI meganuclease of SEQ ID NO: 12, but in which affinity for dimer formation has been altered by at least one modification corresponding to a substitution selected from (a) substitution of R93 with D or E, and (2) a second polypeptide having at least 85% sequence similarity to residues 5-211 of the I-CeuI meganuclease of SEQ ID NO: 12, but in which affinity for dimer formation has been altered by at least one modification corresponding to a substitution selected from (b) substitution of E152 with K or R.

The recombinant meganuclease monomers or heterodimers with altered affinity for dimer formation can also include one, two, three or more of the modifications of base contact residues described above; one, two, three or more of the modifications of backbone contact residues described above; or combinations of both. Thus, for example, the base contacts of a monomer can be modified to alter sequence specificity, the backbone contacts of a monomer can be modified to alter DNA-binding affinity, and the protein-protein interface can be modified to affect dimer formation. Such a recombinant monomer can be combined with a similarly modified monomer to produce a rationally-designed meganuclease heterodimer with desired sequence specificity and activity.

In another aspect, the invention provides for various methods of use for the rationally-designed meganucleases described and enabled herein. These methods include producing genetically-modified cells and organisms, treating diseases by gene therapy, treating pathogen infections, and using the recombinant meganucleases for in vitro applications for diagnostics and research.

Thus, in one aspect, the invention provides methods for producing a genetically-modified eukaryotic cell including an exogenous sequence of interest inserted in a chromosome, by transfecting the cell with (i) a first nucleic acid sequence encoding a meganuclease of the invention, and (ii) a second nucleic acid sequence including said sequence of interest, wherein the meganuclease produces a cleavage site in the chromosome and the sequence of interest is inserted into the chromosome at the cleavage site either by homologous recombination or non-homologous end joining.

Alternatively, in another aspect, the invention provides methods for producing a genetically-modified eukaryotic cell including an exogenous sequence of interest inserted in a chromosome, by introducing a meganuclease protein of the invention into the cell, and transfecting the cell with a nucleic acid including the sequence of interest, wherein the meganuclease produces a cleavage site in the chromosome and the sequence of interest is inserted into the chromosome at the cleavage site either by homologous recombination or non-homologous end joining.

In another aspect, the invention provides methods for producing a genetically-modified eukaryotic cell by disrupting a target sequence in a chromosome, by transfecting the cell with a nucleic acid encoding a meganuclease of the invention, wherein the meganuclease produces a cleavage site in the chromosome and the target sequence is disrupted by non-homologous end joining at the cleavage site.

In another aspect, the invention provides methods of producing a genetically-modified organism by producing a genetically-modified eukaryotic cell according to the methods described above, and growing the genetically-modified eukaryotic cell to produce the genetically-modified organism. In these embodiments, the eukaryotic cell can be selected from a gamete, a zygote, a blastocyst cell, an embryonic stem cell, and a protoplast cell.

In another aspect, the invention provides methods for treating a disease by gene therapy in a eukaryote, by transfecting at least one cell of the eukaryote with one or more nucleic acids including (i) a first nucleic acid sequence encoding a meganuclease of the invention, and (ii) a second nucleic acid sequence including a sequence of interest, wherein the meganuclease produces a cleavage site in the chromosome and the sequence of interest is inserted into the chromosome by homologous recombination or non-homologous end-joining, and insertion of the sequence of interest provides gene therapy for the disease.

Alternatively, in another aspect, the invention provides methods for treating a disease by gene therapy in a eukaryote, by introducing a meganuclease protein of the invention into at least one cell of the eukaryote, and transfecting the cell with a nucleic acid including a sequence of interest, wherein the meganuclease produces a cleavage site in the chromosome and the sequence of interest is inserted into the chromosome at the cleavage site by homologous recombination or non-homologous end-joining, and insertion of the sequence of interest provides gene therapy for the disease.

In another aspect, the invention provides methods for treating a disease by gene therapy in a eukaryote by disrupting a target sequence in a chromosome of the eukaryotic, by transfecting at least one cell of the eukaryote with a nucleic acid encoding a meganuclease of the invention, wherein the meganuclease produces a cleavage site in the chromosome and the target sequence is disrupted by non-homologous end joining at the cleavage site, wherein disruption of the target sequence provides the gene therapy for the disease.

In another aspect, the invention provides methods for treating a viral or prokaryotic pathogen infection in a eukaryotic host by disrupting a target sequence in a genome of the pathogen, by transfecting at least one infected cell of the host with a nucleic acid encoding a meganuclease of the invention, wherein the meganuclease produces a cleavage site in the genome and the target sequence is disrupted by either (1) non-homologous end joining at the cleavage site or (2) by homologous recombination with a second nucleic acid, and wherein disruption of the target sequence provides treatment for the infection.

More generally, in another aspect, the invention provides methods for rationally-designing recombinant meganucleases having altered specificity for at least one base position of a recognition sequence, by (1) determining at least a portion of a three-dimensional structure of a reference meganuclease-DNA complex; (2) identifying amino acid residues forming a base contact surface at the base position; (3) determining a distance between a β-carbon of at least a first residue of the contact surface and at least a first base at the base position; and (4) identifying an amino acid substitution to promote the desired change by either (a) for a first residue which is <6 Å from the first base, selecting a substitution from Group 1 and/or Group 2 which is a member of an appropriate one of Group G, Group C, Group T or Group A; or (b) for a first residue which is >6 Å from said first base, selecting a substitution from Group 2 and/or Group 3 which is a member of an appropriate one of Group G, Group C, Group T or Group A, where each of the Groups is defined herein. This method may be repeated for additional contact residues for the same base, and for contact residues for the other base at the same position, as well as for additional positions.

In addition, in another general aspect, the invention provides methods for rationally-designing a recombinant meganuclease having increased DNA-binding affinity, by (1) determining at least a portion of a three-dimensional structure of a reference meganuclease-DNA complex; (2) identifying amino acid contact residues forming a backbone contact surface; and (3) identifying an amino acid substitution to increase the DNA-binding affinity by (a) for a contact residue having a negatively-charged or hydrophobic side chain, selecting a substitution having an uncharged/polar or positively-charged side chain; or (b) for a contact residue having an uncharged/polar side chain, selecting a substitution having a positively-charged side chain. Conversely, the invention also provides methods for rationally-designing a recombinant meganuclease having decreased DNA-binding affinity, by (1) determining at least a portion of a three-dimensional structure of a reference meganuclease-DNA complex; (2) identifying amino acid contact residues forming a backbone contact surface; (3) identifying an amino acid substitution to decrease the DNA-binding affinity by (a) for a contact residue having a positively-charged side chain, selecting a substitution having an uncharged/polar or negatively-charged side chain; or (b) for a contact residue having an hydrophobic or uncharged/polar side chain, selecting a substitution having a negatively-charged side chain.

These and other aspects and embodiments of the invention will be apparent to one of ordinary skill in the art based upon the following detailed description of the invention.

BRIEF DESCRIPTION OF THE FIGURES

FIG. 2(A) shows a comparison of one recognition sequence for each of the wild type I-CreI meganuclease (WT) and 11 rationally-designed meganuclease heterodimers of the invention. Bases that are conserved relative to the WT recognition sequence are shaded. The 9 bp half-sites are bolded. WT: wild-type (SEQ ID NO: 4); CF: ΔF508 allele of the human CFTR gene responsible for most cases of cystic fibrosis (SEQ ID NO: 25); MYD: the human DM kinase gene associated with myotonic dystrophy (SEQ ID NO: 27); CCR: the human CCR5 gene (a major HIV co-receptor) (SEQ ID NO: 26); ACH: the human FGFR3 gene correlated with achondroplasia (SEQ ID NO: 23); TAT: the HIV-1 TAT/REV gene (SEQ ID NO: 15); HSV: the HSV-1 UL36 gene (SEQ ID NO: 28); LAM: the bacteriophage λ p05 gene (SEQ ID NO: 22); POX: the Variola (smallpox) virus gp009 gene (SEQ ID NO: 30); URA: the *Saccharomyces cerevisiae* URA3 gene (SEQ ID NO: 36); GLA: the *Arabidopsis thaliana* GL2 gene (SEQ ID NO: 32); BRP: the *Arabidopsis thaliana* BP-1 gene (SEQ ID NO: 33).

FIG. 2(B) illustrates the results of incubation of each of wild-type I-CreI (WT) and 11 rationally-designed meganuclease heterodimers with plasmids harboring the recognition sites for all 12 enzymes for 6 hours at 37° C. Percent cleavage is indicated in each box.

Figure 1:
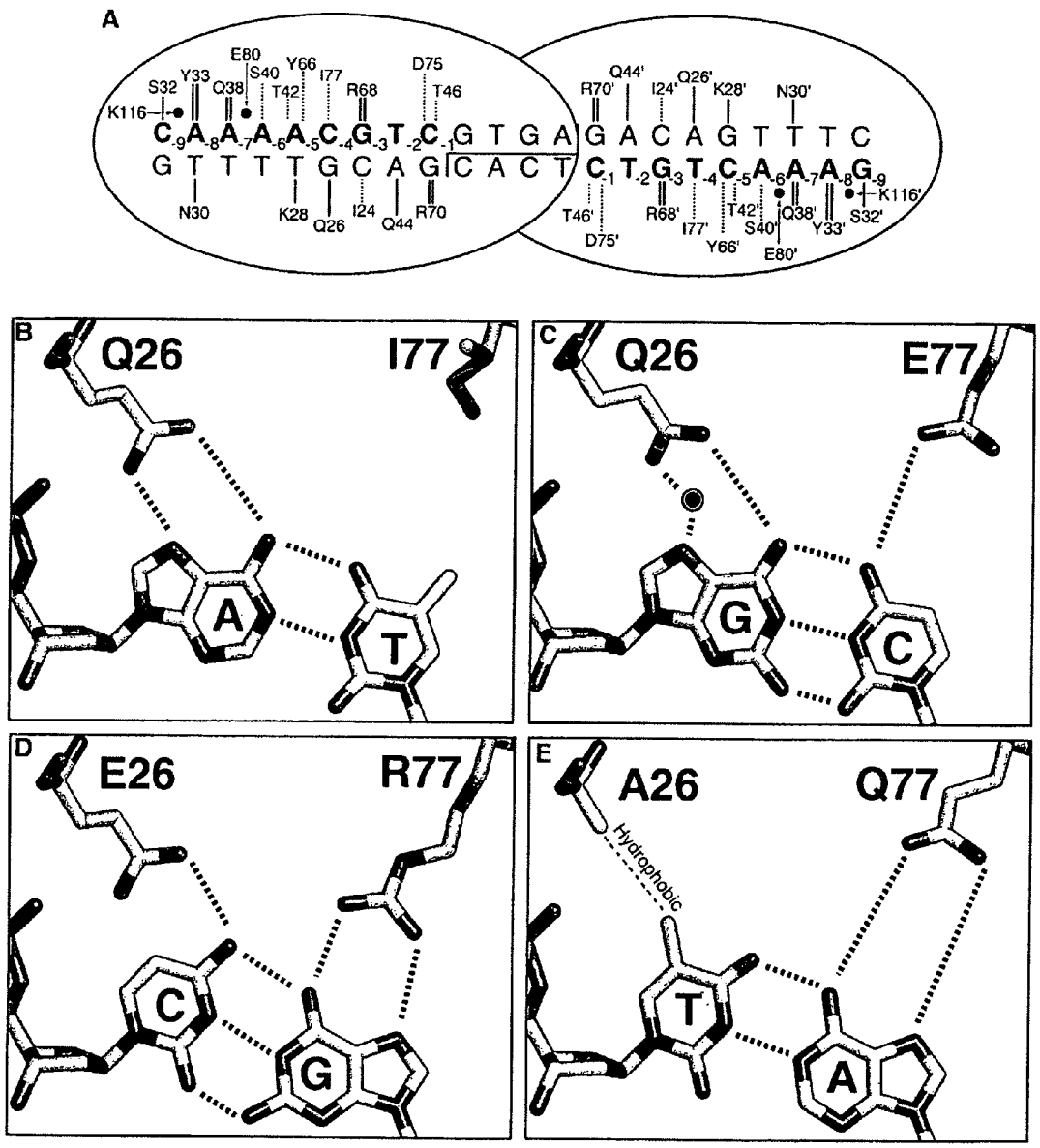
FIG. 1(A) illustrates the interactions between the I-CreI homodimer and its naturally-occurring double-stranded recognition sequence, based upon crystallographic data. This schematic representation depicts the recognition sequence (SEQ ID NO: 2 and SEQ ID NO: 3), shown as unwound for illustration purposes only, bound by the homodimer, shown as two ovals. The bases of each DNA half-site are numbered −1 through −9, and the amino acid residues of I-CreI which form the recognition surface are indicated by one-letter amino acid designations and numbers indicating residue position. Solid black lines: hydrogen bonds to DNA bases. Dashed lines: amino acid positions that form additional contacts in enzyme designs but do not contact the DNA in the wild-type complex. Arrows: residues that interact with the DNA backbone and influence cleavage activity.
FIG. 1(B) illustrates the wild-type contacts between the A-T base pair at position −4 of the cleavage half-site on the right side of FIG. 1(A). Specifically, the residue Q26 is shown to interact with the A base. Residue 177 is in proximity to the base pair but not specifically interacting.
FIG. 1(C) illustrates the interactions between a rationally-designed variant of the I-CreI meganuclease in which residue 177 has been modified to E77. As a result of this change, a G-C base pair is preferred at position −4. The interaction between Q26 and the G base is mediated by a water molecule, as has been observed crystallographically for the cleavage half-site on the left side of FIG. 1(A).
FIG. 1(D) illustrates the interactions between a rationally-designed variant of the I-CreI meganuclease in which residue Q26 has been modified to E26 and residue 177 has been modified to R77. As a result of this change, a C-G base pair is preferred at position −4.
FIG. 1(E) illustrates the interactions between a rationally-designed variant of the I-CreI meganuclease in which residue Q26 has been modified to A26 and residue 177 has been modified to Q77. As a result of this change, a T-A base pair is preferred at position −4.

DETAILED DESCRIPTION OF THE INVENTION 1.1 Introduction

The present invention is based, in part, upon the identification and characterization of specific amino acids in the LAGLIDADG family of meganucleases that make specific contacts with DNA bases and non-specific contacts with the DNA backbone when the meganucleases associate with a double-stranded DNA recognition sequence, and which thereby affect the recognition sequence specificity and DNA-binding affinity of the enzymes. This discovery has been used, as described in detail below, to identify amino acid substitutions in the meganucleases that can alter the specificity and/or affinity of the enzymes, and to rationally design and develop meganucleases that can recognize a desired DNA sequence that naturally-occurring meganucleases do not recognize, and/or that have increased or decreased specificity and/or affinity relative to the naturally-occurring meganucleases. Furthermore, because DNA-binding affinity affects enzyme activity as well as sequence-specificity, the invention provides rationally-designed meganucleases with altered activity relative to naturally-occurring meganucleases. In addition, the invention provides rationally-designed meganucleases in which residues at the interface between the monomers associated to form a dimer have been modified in order to promote heterodimer formation. Finally, the invention provides uses for the rationally-designed meganucleases in the production of recombinant cells and organisms, as well as in gene therapy, anti-pathogen, anti-cancer, and in vitro applications, as disclosed herein.

As a general matter, the invention provides methods for generating rationally-designed LAGLIDADG meganucleases containing altered amino acid residues at sites within the meganuclease that are responsible for (1) sequence-specific binding to individual bases in the double-stranded DNA recognition sequence, or (2) non-sequence-specific binding to the phosphodiester backbone of a double-stranded DNA molecule. Because enzyme activity is correlated to DNA-binding affinity, however, altering the amino acids involved in binding to the DNA recognition sequence can alter not only the specificity of the meganuclease through specific base pair interactions, but also the activity of the meganuclease by increasing or decreasing overall binding affinity for the double-stranded DNA. Similarly, altering the amino acids involved in binding to the DNA backbone can alter not only the activity of the enzyme, but also the degree of specificity or degeneracy of binding to the recognition sequence by increasing or decreasing overall binding affinity for the double-stranded DNA.

As described in detail below, the methods of rationally-designing meganucleases include the identification of the amino acids responsible for DNA recognition/binding, and the application of a series of rules for selecting appropriate amino acid changes. With respect to meganuclease sequence specificity, the rules include both steric considerations relating to the distances in a meganuclease-DNA complex between the amino acid side chains of the meganuclease and the bases in the sense and anti-sense strands of the DNA, and considerations relating to the non-covalent chemical interactions between functional groups of the amino acid side chains and the desired DNA base at the relevant position.

Finally, a majority of natural meganucleases that bind DNA as homodimers recognize pseudo- or completely palindromic recognition sequences. Because lengthy palindromes are expected to be rare, the likelihood of encountering a palindromic sequence at a genomic site of interest is exceedingly low. Consequently, if these enzymes are to be redesigned to recognize genomic sites of interest, it is necessary to design two enzyme monomers recognizing different half-sites that can heterodimerize to cleave the non-palindromic hybrid recognition sequence. Therefore, in some aspects, the invention provides rationally-designed meganucleases in which monomers differing by at least one amino acid position are dimerized to form heterodimers. In some cases, both monomers are rationally-designed to form a heterodimer which recognizes a non-palindromic recognition sequence. A mixture of two different monomers can result in up to three active forms of meganuclease dimer: the two homodimers and the heterodimer. In addition or alternatively, in some cases, amino acid residues are altered at the interfaces at which monomers can interact to form dimers, in order to increase or decrease the likelihood of formation of homodimers or heterodimers.

Thus, in one aspect, the invention provide methods for rationally designing LAGLIDADG meganucleases containing amino acid changes that alter the specificity and/or activity of the enzymes. In another aspect, the invention provides the rationally-designed meganucleases resulting from these methods. In another aspect, the invention provides methods that use such rationally-designed meganucleases to produce recombinant nucleic acids and organisms in which a desired DNA sequence or genetic locus within the genome of an organism is modified by the insertion, deletion, substitution or other manipulation of DNA sequences. In another aspect, the invention provides methods for reducing the survival of pathogens or cancer cells using rationally-designed meganucleases which have pathogen-specific or cancer-specific recognition sequences.

1.2 References and Definitions

The patent and scientific literature referred to herein establishes knowledge that is available to those of skill in the art. The issued U.S. patents, allowed applications, published foreign applications, and references, including GenBank database sequences, that are cited herein are hereby incorporated by reference to the same extent as if each was specifically and individually indicated to be incorporated by reference.

As used herein, the term "meganuclease" refers to an endonuclease that binds double-stranded DNA at a recognition sequence that is greater than 12 base pairs. Naturally-occurring meganucleases can be monomeric (e.g., I-SceI) or dimeric (e.g., I-CreI). The term meganuclease, as used herein, can be used to refer to monomeric meganucleases, dimeric meganucleases, or to the monomers which associate to form a dimeric meganuclease. The term "homing endonuclease" is synonymous with the term "meganuclease."

As used herein, the term "LAGLIDADG meganuclease" refers either to meganucleases including a single LAGLIDADG motif, which are naturally dimeric, or to meganucleases including two LAGLIDADG motifs, which are naturally monomeric. The term "mono-LAGLIDADG meganuclease" is used herein to refer to meganucleases including a single LAGLIDADG motif, and the term "di-LAGLIDADG meganuclease" is used herein to refer to meganucleases including two LAGLIDADG motifs, when it is necessary to distinguish between the two. Each of the two structural domains of a di-LAGLIDADG meganuclease which includes a LAGLIDADG motif can be referred to as a LAGLIDADG subunit.

As used herein, the term "rationally-designed" means non-naturally occurring and/or genetically engineered. The rationally-designed meganucleases of the invention differ from wild-type or naturally-occurring meganucleases in their amino acid sequence or primary structure, and may also differ in their secondary, tertiary or quaternary structure. In addition, the rationally-designed meganucleases of the invention also differ from wild-type or naturally-occurring meganucleases in recognition sequence-specificity and/or activity.

As used herein, with respect to a protein, the term "recombinant" means having an altered amino acid sequence as a result of the application of genetic engineering techniques to nucleic acids which encode the protein, and cells or organisms which express the protein. With respect to a nucleic acid, the term "recombinant" means having an altered nucleic acid sequence as a result of the application of genetic engineering techniques. Genetic engineering techniques include, but are not limited to, PCR and DNA cloning technologies; transfection, transformation and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant.

As used herein with respect to recombinant proteins, the term "modification" means any insertion, deletion or substitution of an amino acid residue in the recombinant sequence relative to a reference sequence (e.g., a wild-type).

As used herein, the term "genetically-modified" refers to a cell or organism in which, or in an ancestor of which, a genomic DNA sequence has been deliberately modified by recombinant technology. As used herein, the term "genetically-modified" encompasses the term "transgenic."

As used herein, the term "wild-type" refers to any naturally-occurring form of a meganuclease. The term "wild-type" is not intended to mean the most common allelic variant of the enzyme in nature but, rather, any allelic variant found in nature. Wild-type meganucleases are distinguished from recombinant or non-naturally-occurring meganucleases.

As used herein, the term "recognition sequence half-site" or simply "half site" means a nucleic acid sequence in a double-stranded DNA molecule which is recognized by a monomer of a mono-LAGLIDADG meganuclease or by one LAGLIDADG subunit of a di-LAGLIDADG meganuclease.

As used herein, the term "recognition sequence" refers to a pair of half-sites which is bound and cleaved by either a mono-LAGLIDADG meganuclease dimer or a di-LAGLIDADG meganuclease monomer. The two half-sites may or may not be separated by base pairs that are not specifically recognized by the enzyme. In the cases of I-CreI, I-MsoI and I-CeuI, the recognition sequence half-site of each monomer spans 9 base pairs, and the two half-sites are separated by four base pairs which are not recognized specifically but which constitute the actual cleavage site (which has a 4 base pair overhang). Thus, the combined recognition sequences of the I-CreI, I-MsoI and I-CeuI meganuclease dimers normally span 22 base pairs, including two 9 base pair half-sites flanking a 4 base pair cleavage site. The base pairs of each half-site are designated −9 through −1, with the −9 position being most distal from the cleavage site and the −1 position being adjacent to the 4 central base pairs, which are designated $N_1$—$N_4$. The strand of each half-site which is oriented 5' to 3' in the direction from −9 to −1 (i.e., towards the cleavage site), is designated the "sense" strand and the opposite strand is designated the "antisense strand", although neither strand may encode protein. Thus, the "sense" strand of one half-site is the antisense strand of the other half-site. See, for example, FIG. 1(A). In the case of the I-SceI meganuclease, which is a di-LAGLIDADG meganuclease monomer, the recognition sequence is an approximately 18 bp non-palindromic sequence, and there are no central base pairs which are not specifically recognized. By convention, one of the two strands is referred to as the "sense" strand and the other the "antisense" strand, although neither strand may encode protein.

As used herein, the term "specificity" means the ability of a meganuclease to recognize and cleave double-stranded DNA molecules only at a particular sequence of base pairs referred to as the recognition sequence, or only at a particular set of recognition sequences. The set of recognition sequences will share certain conserved positions or sequence motifs, but may be degenerate at one or more positions. A highly-specific meganuclease is capable of cleaving only one or a very few recognition sequences. Specificity can be determined in a cleavage assay as described in Example 1. As used herein, a meganuclease has "altered" specificity if it binds to and cleaves a recognition sequence which is not bound to and cleaved by a reference meganuclease (e.g., a wild-type) or if the rate of cleavage of a recognition sequence is increased or decreased by a statistically significant ($p<0.05$) amount relative to a reference meganuclease.

As used herein, the term "degeneracy" means the opposite of "specificity." A highly-degenerate meganuclease is capable of cleaving a large number of divergent recognition sequences. A meganuclease can have sequence degeneracy at a single position within a half-site or at multiple, even all, positions within a half-site. Such sequence degeneracy can result from (i) the inability of any amino acid in the DNA-binding domain of a meganuclease to make a specific contact with any base at one or more positions in the recognition sequence, (ii) the ability of one or more amino acids in the DNA-binding domain of a meganuclease to make specific contacts with more than one base at one or more positions in the recognition sequence, and/or (iii) sufficient non-specific DNA binding affinity for activity. A "completely" degenerate position can be occupied by any of the four bases and can be designated with an "N" in a half-site. A "partially" degenerate position can be occupied by two or three of the four bases (e.g., either purine (Pu), either pyrimidine (Py), or not G).

As used herein with respect to meganucleases, the term "DNA-binding affinity" or "binding affinity" means the tendency of a meganuclease to non-covalently associate with a reference DNA molecule (e.g., a recognition sequence or an arbitrary sequence). Binding affinity is measured by a dissociation constant, $K_D$ (e.g., the $K_D$ of I-CreI for the WT recognition sequence is approximately 0.1 nM). As used herein, a meganuclease has "altered" binding affinity if the $K_D$ of the recombinant meganuclease for a reference recognition sequence is increased or decreased by a statistically significant ($p<0.05$) amount relative to a reference meganuclease.

As used herein with respect to meganuclease monomers, the term "affinity for dimer formation" means the tendency of a meganuclease monomer to non-covalently associate with a reference meganuclease monomer. The affinity for dimer formation can be measured with the same monomer (i.e., homodimer formation) or with a different monomer (i.e., heterodimer formation) such as a reference wild-type meganuclease. Binding affinity is measured by a dissociation constant, $K_D$. As used herein, a meganuclease has "altered" affinity for dimer formation if the $K_D$ of the recombinant meganuclease monomer for a reference meganuclease monomer is increased or decreased by a statistically significant ($p<0.05$) amount relative to a reference meganuclease monomer.

As used herein, the term "palindromic" refers to a recognition sequence consisting of inverted repeats of identical half-sites. In this case, however, the palindromic sequence need not be palindromic with respect to the four central base pairs, which are not contacted by the enzyme. In the case of dimeric meganucleases, palindromic DNA sequences are recognized by homodimers in which the two monomers make contacts with identical half-sites.

As used herein, the term "pseudo-palindromic" refers to a recognition sequence consisting of inverted repeats of non-identical or imperfectly palindromic half-sites. In this case, the pseudo-palindromic sequence not only need not be palindromic with respect to the four central base pairs, but also can deviate from a palindromic sequence between the two half-sites. Pseudo-palindromic DNA sequences are typical of the natural DNA sites recognized by wild-type homodimeric meganucleases in which two identical enzyme monomers make contacts with different half-sites.

As used herein, the term "non-palindromic" refers to a recognition sequence composed of two unrelated half-sites of a meganuclease. In this case, the non-palindromic sequence need not be palindromic with respect to either the four central base pairs or the two monomer half-sites. Non-palindromic DNA sequences are recognized by either di-LAGLIDADG meganucleases, highly degenerate mono-LAGLIDADG meganucleases (e.g., I-CeuI) or by heterodimers of mono-LAGLIDADG meganuclease monomers that recognize non-identical half-sites.

As used herein, the term "activity" refers to the rate at which a meganuclease of the invention cleaves a particular recognition sequence. Such activity is a measurable enzymatic reaction, involving the hydrolysis of phosphodiester bonds of double-stranded DNA. The activity of a meganuclease acting on a particular DNA substrate is affected by the affinity or avidity of the meganuclease for that particular DNA substrate which is, in turn, affected by both sequence-specific and non-sequence-specific interactions with the DNA.

As used herein, the term "homologous recombination" refers to the natural, cellular process in which a double-stranded DNA-break is repaired using a homologous DNA sequence as the repair template (see, e.g. Cahill et al. (2006), *Front. Biosci.* 11:1958-1976). The homologous DNA sequence may be an endogenous chromosomal sequence or an exogenous nucleic acid that was delivered to the cell. Thus, in some embodiments, a rationally-designed meganuclease is used to cleave a recognition sequence within a target sequence and an exogenous nucleic acid with homology to or substantial sequence similarity with the target sequence is delivered into the cell and used as a template for repair by homologous recombination. The DNA sequence of the exogenous nucleic acid, which may differ significantly from the target sequence, is thereby incorporated into the chromosomal sequence. The process of homologous recombination occurs primarily in eukaryotic organisms. The term "homology" is used herein as equivalent to "sequence similarity" and is not intended to require identity by descent or phylogenetic relatedness.

As used herein, the term "non-homologous end-joining" refers to the natural, cellular process in which a double-stranded DNA-break is repaired by the direct joining of two non-homologous DNA segments (see, e.g. Cahill et al. (2006), *Front. Biosci.* 11:1958-1976). DNA repair by non-homologous end joining is error-prone and frequently results in the untemplated addition or deletion of DNA sequences at the site of repair. Thus, in certain embodiments, a rationally-designed meganuclease can be used to produce a double-stranded break at a meganuclease recognition sequence within a target sequence to disrupt a gene (e.g., by introducing base insertions, base deletions, or frameshift mutations) by non-homologous end-joining. In other embodiments, an exogenous nucleic acid lacking homology to or substantial sequence similarity with the target sequence may be captured at the site of a meganuclease-stimulated double-stranded DNA break by non-homologous end joining (see, e.g. Salomon, et al. (1998), *EMBO J.* 17:6086-6095). The process of non-homologous end joining occurs in both eukaryotes and prokaryotes such as bacteria.

As used herein, the term "sequence of interest" means any nucleic acid sequence, whether it codes for a protein, RNA, or regulatory element (e.g., an enhancer, silencer, or promoter sequence), that can be inserted into a genome or used to replace a genomic DNA sequence using a meganuclease protein. Sequences of interest can have heterologous DNA sequences that allow for tagging a protein or RNA that is expressed from the sequence of interest. For instance, a protein can be tagged with tags including, but not limited to, an epitope (e.g., c-myc, FLAG) or other ligand (e.g., poly-His). Furthermore, a sequence of interest can encode a fusion protein, according to techniques known in the art (see, e.g., Ausubel et al., *Current Protocols in Molecular Biology*, Wiley 1999). In some embodiments, the sequence of interest is flanked by a DNA sequence that is recognized by the recombinant meganuclease for cleavage. Thus, the flanking sequences are cleaved allowing for proper insertion of the sequence of interest into genomic recognition sequences cleaved by the recombinant meganuclease. In some embodiments, the entire sequence of interest is homologous to or has substantial sequence similarity with the a target sequence in the genome such that homologous recombination effectively replaces the target sequence with the sequence of interest. In other embodiments, the sequence of interest is flanked by DNA sequences with homology to or substantial sequence similarity with the target sequence such that homologous recombination inserts the sequence of interest within the genome at the locus of the target sequence. In some embodiments, the sequence of interest is substantially identical to the target sequence except for mutations or other modifications in the meganuclease recognition sequence such that the meganuclease can not cleave the target sequence after it has been modified by the sequence of interest.

As used herein with respect to both amino acid sequences and nucleic acid sequences, the terms "percentage similarity" and "sequence similarity" refer to a measure of the degree of similarity of two sequences based upon an alignment of the sequences which maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (ncbi.nlm.nih.gov/), and are described in, for example, Altschul et al. (1990), *J. Mol. Biol.* 215:403-410; Gish and States (1993), *Nature Genet.* 3:266-272; Madden et al. (1996), *Meth. Enzymol.* 266:131-141; Altschul et al. (1997), *Nucleic Acids Res.* 25:33 89-3402); Zhang et al. (2000), *J. Comput. Biol.* 7(1-2):203-14. As used herein, percent similarity of two amino acid sequences is the score based upon the following parameters for the BLASTp algorithm: word size=3; gap opening penalty=−11; gap extension penalty=−1; and scoring matrix=BLOSUM62. As used herein, percent similarity of two nucleic acid sequences is the score based upon the following parameters for the BLASTn algorithm: word size=11; gap opening penalty=−5; gap extension penalty=−2; match reward=1; and mismatch penalty=−3.

As used herein with respect to modifications of two proteins or amino acid sequences, the term "corresponding to" is used to indicate that a specified modification in the first protein is a substitution of the same amino acid residue as in the modification in the second protein, and that the amino acid position of the modification in the first proteins corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment, and despite the fact that X and Y may be different numbers.

As used herein, the recitation of a numerical range for a variable is intended to convey that the invention may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values $\geq 0$ and $\leq 2$ if the variable is inherently continuous.

As used herein, unless specifically indicated otherwise, the word "or" is used in the inclusive sense of "and/or" and not the exclusive sense of "either/or."

2.1 Rationally-Designed Meganucleases with Altered Sequence-Specificity

In one aspect of the invention, methods for rationally designing recombinant LAGLIDADG family meganucleases are provided. In this aspect, recombinant meganucleases are rationally-designed by first predicting amino acid substitutions that can alter base preference at each position in the half-site. These substitutions can be experimentally validated individually or in combinations to produce meganucleases with the desired cleavage specificity.

In accordance with the invention, amino acid substitutions that can cause a desired change in base preference are predicted by determining the amino acid side chains of a reference meganuclease (e.g., a wild-type meganuclease, or a non-naturally-occurring reference meganuclease) that are able to participate in making contacts with the nucleic acid bases of the meganuclease's DNA recognition sequence and the DNA phosphodiester backbone, and the spatial and chemical nature of those contacts. These amino acids include but are not limited to side chains involved in contacting the reference DNA half-site. Generally, this determination requires having knowledge of the structure of the complex between the meganuclease and its double-stranded DNA recognition sequence, or knowledge of the structure of a highly similar complex (e.g., between the same meganuclease and an alternative DNA recognition sequence, or between an allelic or phylogenetic variant of the meganuclease and its DNA recognition sequence).

Three-dimensional structures, as described by atomic coordinates data, of a polypeptide or complex of two or more polypeptides can be obtained in several ways. For example, protein structure determinations can be made using techniques including, but not limited to, X-ray crystallography, NMR, and mass spectrometry. Another approach is to analyze databases of existing structural co-ordinates for the meganuclease of interest or a related meganuclease. Such structural data is often available from databases in the form of three-dimensional coordinates. Often this data is accessible through online databases (e.g., the RCSB Protein Data Bank at rcsb.org/pdb).

Structural information can be obtained experimentally by analyzing the diffraction patterns of, for example, X-rays or electrons, created by regular two- or three-dimensional arrays (e.g., crystals) of proteins or protein complexes. Computational methods are used to transform the diffraction data into three-dimensional atomic co-ordinates in space. For example, the field of X-ray crystallography has been used to generate three-dimensional structural information on many protein-DNA complexes, including meganucleases (see, e.g., Chevalier et al. (2001), *Nucleic Acids Res.* 29(18): 3757-3774).

Nuclear Magnetic Resonance (NMR) also has been used to determine inter-atomic distances of molecules in solution. Multi-dimensional NMR methods combined with computational methods have succeeded in determining the atomic co-ordinates of polypeptides of increasing size (see, e.g., Tzakos et al. (2006), *Annu. Rev. Biophys. Biomol. Struct.* 35:19-42).

Alternatively, computational modeling can be used by applying algorithms based on the known primary structures and, when available, secondary, tertiary and/or quaternary structures of the protein/DNA, as well as the known physio-chemical nature of the amino acid side chains, nucleic acid bases, and bond interactions. Such methods can optionally include iterative approaches, or experimentally-derived constraints. An example of such computational software is the CNS program described in Adams et al. (1999), *Acta Crystallogr. D. Biol. Crystallogr.* 55 (Pt 1): 181-90. A variety of other computational programs have been developed that predict the spatial arrangement of amino acids in a protein structure and predict the interaction of the amino acid side chains of the protein with various target molecules (see, e.g., U.S. Pat. No. 6,988,041).

Thus, in some embodiments of the invention, computational models are used to identify specific amino acid residues that specifically interact with DNA nucleic acid bases and/or facilitate non-specific phosphodiester backbone interactions. For instance, computer models of the totality of the potential meganuclease-DNA interaction can be produced using a suitable software program, including, but not limited to, MOL-SCRIPT™ 2.0 (Avatar Software AB, Stockholm, Sweden), the graphical display program O (Jones et. al. (1991), *Acta Crystallography*, A47: 110), the graphical display program GRASP™ (Nicholls et al. (1991), *PROTEINS, Structure, Function and Genetics* 11(4): 281ff), or the graphical display program INSIGHT™ (TSI, Inc., Shoreview, Minn.). Computer hardware suitable for producing, viewing and manipulating three-dimensional structural representations of protein-DNA complexes are commercially available and well known in the art (e.g., Silicon Graphics Workstation, Silicon Graphics, Inc., Mountainview, Calif.).

Specifically, interactions between a meganuclease and its double-stranded DNA recognition sequences can be resolved using methods known in the art. For example, a representation, or model, of the three dimensional structure of a multi-component complex structure, for which a crystal has been produced, can be determined using techniques which include molecular replacement or SIR/MIR (single/multiple isomorphous replacement) (see, e.g., Brunger (1997), *Meth. Enzym.* 276: 558-580; Navaza and Saludjian (1997), *Meth. Enzym.* 276: 581-594; Tong and Rossmann (1997), *Meth. Enzym.* 276: 594-611; and Bentley (1997), *Meth. Enzym.* 276: 611-619) and can be performed using a software program, such as AMoRe/Mosflm (Navaza (1994), *Acta Cryst.* A50: 157-163; CCP4 (1994), *Acta Cryst.* D50: 760-763) or XPLOR (see, Brünger et al. (1992), *X-PLOR Version 3.1. A System for X-ray Crystallography and NMR*, Yale University Press, New Haven, Conn.).

The determination of protein structure and potential meganuclease-DNA interaction allows for rational choices concerning the amino acids that can be changed to affect enzyme activity and specificity. Decisions are based on several factors regarding amino acid side chain interactions with a particular base or DNA phosphodiester backbone. Chemical interactions used to determine appropriate amino acid substitutions include, but are not limited to, van der Waals forces, steric hindrance, ionic bonding, hydrogen bonding, and hydrophobic interactions. Amino acid substitutions can be selected which either favor or disfavor specific interactions of the meganuclease with a particular base in a potential recognition sequence half-site in order to increase or decrease specificity for that sequence and, to some degree, overall binding affinity and activity. In addition, amino acid substitutions can be selected which either increase or decrease binding affinity for the phosphodiester backbone of double-stranded DNA in order to increase or decrease overall activity and, to some degree, to decrease or increase specificity.

Thus, in specific embodiments, a three-dimensional structure of a meganuclease-DNA complex is determined and a "contact surface" is defined for each base-pair in a DNA recognition sequence half-site. In some embodiments, the contact surface comprises those amino acids in the enzyme with β-carbons less than 9.0 Å from a major groove hydrogen-bond donor or acceptor on either base in the pair, and with side chains oriented toward the DNA, irrespective of whether the residues make base contacts in the wild-type meganuclease-DNA complex. In other embodiments, residues can be excluded if the residues do not make contact in the wild-type meganuclease-DNA complex, or residues can be included or excluded at the discretion of the designer to alter the number or identity of the residues considered. In one example, as described below, for base positions −2, −7, −8, and −9 of the wild-type I-CreI half-site, the contact surfaces were limited to the amino acid positions that actually interact in the wild-type enzyme-DNA complex. For positions −1, −3, −4, −5, and −6, however, the contact surfaces were defined to contain additional amino acid positions that are not involved in wild-type contacts but which could potentially contact a base if substituted with a different amino acid.

It should be noted that, although a recognition sequence half-site is typically represented with respect to only one strand of DNA, meganucleases bind in the major groove of double-stranded DNA, and make contact with nucleic acid bases on both strands. In addition, the designations of "sense" and "antisense" strands are completely arbitrary with respect to meganuclease binding and recognition. Sequence specificity at a position can be achieved either through interactions with one member of a base pair, or by a combination of interactions with both members of a base-pair. Thus, for example, in order to favor the presence of an A/T base pair at position X, where the A base is on the "sense" strand and the T base is on the "antisense" strand, residues are selected which are sufficiently close to contact the sense strand at position X and which favor the presence of an A, and/or residues are selected which are sufficiently close to contact the antisense strand at position X and which favor the presence of a T. In accordance with the invention, a residue is considered sufficiently close if the β-carbon of the residue is within 9 Å of the closest atom of the relevant base.

Thus, for example, an amino acid with a β-carbon within 9 Å of the DNA sense strand but greater than 9 Å from the antisense strand is considered for potential interactions with only the sense strand. Similarly, an amino acid with a β-carbon within 9 Å of the DNA antisense strand but greater than 9 Å from the sense strand is considered for potential interactions with only the antisense strand. Amino acids with β-carbons that are within 9 Å of both DNA strands are considered for potential interactions with either strand.

For each contact surface, potential amino acid substitutions are selected based on their predicted ability to interact favorably with one or more of the four DNA bases. The selection process is based upon two primary criteria: (i) the size of the amino acid side chains, which will affect their steric interactions with different nucleic acid bases, and (ii) the chemical nature of the amino acid side chains, which will affect their electrostatic and bonding interactions with the different nucleic acid bases.

With respect to the size of side chains, amino acids with shorter and/or smaller side chains can be selected if an amino acid β-carbon in a contact surface is <6 Å from a base, and amino acids with longer and/or larger side chains can be selected if an amino acid β-carbon in a contact surface is >6 Å from a base. Amino acids with side chains that are intermediate in size can be selected if an amino acid β-carbon in a contact surface is 5-8 Å from a base.

The amino acids with relatively shorter and smaller side chains can be assigned to Group 1, including glycine (G), alanine (A), serine (S), threonine (T), cysteine (C), valine (V), leucine (L), isoleucine (I), aspartate (D), asparagine (N) and proline (P). Proline, however, is expected to be used less frequently because of its relative inflexibility. In addition, glycine is expected to be used less frequently because it introduces unwanted flexibility in the peptide backbone and its very small size reduces the likelihood of effective contacts when it replaces a larger residue. On the other hand, glycine can be used in some instances for promoting a degenerate position. The amino acids with side chains of relatively intermediate length and size can be assigned to Group 2, including lysine (K), methionine (M), arginine (R), glutamate (E) and glutamine (Q). The amino acids with relatively longer and/or larger side chains can be assigned to Group 3, including lysine (K), methionine (M), arginine (R), histidine (H), phenylalanine (F), tyrosine (Y), and tryptophan (W). Tryptophan, however, is expected to be used less frequently because of its relative inflexibility. In addition, the side chain flexibility of lysine, arginine, and methionine allow these amino acids to make base contacts from long or intermediate distances, warranting their inclusion in both Groups 2 and 3. These groups are also shown in tabular form below:

| Group 1 | Group 2 | Group 3 |
|---|---|---|
| glycine (G) | glutamine (Q) | arginine (R) |
| alanine (A) | glutamate (E) | histidine (H) |
| serine (S) | lysine (K) | phenylalanine (F) |
| threonine (T) | methionine (M) | tyrosine (Y) |
| cysteine (C) | arginine (R) | tryptophan (W) |
| valine (V) | | lysine (K) |
| leucine (L) | | methionine (M) |
| isoleucine (I) | | |
| aspartate (D) | | |
| asparagine (N) | | |
| proline (P) | | |

With respect to the chemical nature of the side chains, the different amino acids are evaluated for their potential interactions with the different nucleic acid bases (e.g., van der Waals forces, ionic bonding, hydrogen bonding, and hydrophobic interactions) and residues are selected which either favor or disfavor specific interactions of the meganuclease with a particular base at a particular position in the double-stranded DNA recognition sequence half-site. In some instances, it may be desired to create a half-site with one or more complete or partial degenerate positions. In such cases, one may choose residues which favor the presence of two or more bases, or residues which disfavor one or more bases. For example, partial degenerate base recognition can be achieved by sterically hindering a pyrimidine at a sense or antisense position.

Recognition of guanine (G) bases is achieved using amino acids with basic side chains that form hydrogen bonds to N7 and O6 of the base. Cytosine (C) specificity is conferred by negatively-charged side chains which interact unfavorably with the major groove electronegative groups present on all bases except C. Thymine (T) recognition is rationally-designed using hydrophobic and van der Waals interactions between hydrophobic side chains and the major groove methyl group on the base. Finally, adenine (A) bases are recognized using the carboxamide side chains Asn and Gln or the hydroxyl side chain of Tyr through a pair of hydrogen bonds to N7 and N6 of the base. Lastly, His can be used to confer specificity for a purine base (A or G) by donating a hydrogen bond to N7. These straightforward rules for DNA recognition can be applied to predict contact surfaces in which one or both of the bases at a particular base-pair position are recognized through a rationally-designed contact.

Thus, based on their binding interactions with the different nucleic acid bases, and the bases which they favor at a position with which they make contact, each amino acid residue can be assigned to one or more different groups corresponding to the different bases they favor (i.e., G, C, T or A). Thus, Group G includes arginine (R), lysine (K) and histidine (H); Group C includes aspartate (D) and glutamate (E); Group T includes alanine (A), valine (V), leucine (L), isoleucine (I), cysteine (C), threonine (T), methionine (M) and phenylalanine (F); and Group A includes asparagine (N), glutamine (N), tyrosine (Y) and histidine (H). Note that histidine appears in both Group G and Group A; that serine (S) is not included in any group but may be used to favor a degenerate position; and that proline, glycine, and tryptophan are not included in any particular group because of predominant steric considerations. These groups are also shown in tabular form below:

| Group G | Group C | Group T | Group A |
| --- | --- | --- | --- |
| arginine (R) | aspartate (D) | alanine (A) | asparagine (N) |
| lysine (K) | glutamate (E) | valine (V) | glutamine (Q) |
| histidine (H) | | leucine (L) | tyrosine (Y) |
| | | isoleucine (I) | histidine (H) |
| | | cysteine (C) | |
| | | threonine (T) | |
| | | methionine (M) | |
| | | phenylalanine (F) | |

Thus, in accordance with the invention, in order to effect a desired change in the recognition sequence half-site of a meganuclease at a given position X, (1) determine at least the relevant portion of the three-dimensional structure of the wild-type or reference meganuclease-DNA complex and the amino acid residue side chains which define the contact surface at position X; (2) determine the distance between the β-carbon of at least one residue comprising the contact surface and at least one base of the base pair at position X; and (3)(a) for a residue which is <6 Å from the base, select a residue from Group 1 and/or Group 2 which is a member of the appropriate one of Group G, Group C, Group T or Group A to promote the desired change, and/or (b) for a residue which is >6 Å from the base, select a residue from Group 2 and/or Group 3 which is a member of the appropriate one of Group G, Group C, Group T or Group A to promote the desired change. More than one such residue comprising the contact surface can be selected for analysis and modification and, in some embodiments, each such residue is analyzed and multiple residues are modified. Similarly, the distance between the β-carbon of a residue included in the contact surface and each of the two bases of the base pair at position X can be determined and, if the residue is within 9 Å of both bases, then different substitutions can be made to affect the two bases of the pair (e.g., a residue from Group 1 to affect a proximal base on one strand, or a residue from Group 3 to affect a distal base on the other strand). Alternatively, a combination of residue substitutions capable of interacting with both bases in a pair can affect the specificity (e.g., a residue from the T Group contacting the sense strand combined with a residue from the A Group contacting the antisense strand to select for T/A). Finally, multiple alternative modifications of the residues can be validated either empirically (e.g., by producing the recombinant meganuclease and testing its sequence recognition) or computationally (e.g., by computer modeling of the meganuclease-DNA complex of the modified enzyme) to choose amongst alternatives.

Once one or more desired amino acid modifications of the wild-type or reference meganuclease are selected, the rationally-designed meganuclease can be produced by recombinant methods and techniques well known in the art. In some embodiments, non-random or site-directed mutagenesis techniques are used to create specific sequence modifications. Non-limiting examples of non-random mutagenesis techniques include overlapping primer PCR (see, e.g., Wang et al. (2006), *Nucleic Acids Res.* 34(2): 517-527), site-directed mutagenesis (see, e.g., U.S. Pat. No. 7,041,814), cassette mutagenesis (see, e.g., U.S. Pat. No. 7,041,814), and the manufacturer's protocol for the Altered Sites® II Mutagenesis Systems kit commercially available from Promega Biosciences, Inc. (San Luis Obispo, Calif.).

The recognition and cleavage of a specific DNA sequence by a rationally-designed meganuclease can be assayed by any method known by one skilled in the art (see, e.g., U.S. Pat. Pub. No. 2006/0078552). In certain embodiments, the determination of meganuclease cleavage is determined by in vitro cleavage assays. Such assays use in vitro cleavage of a polynucleotide substrate comprising the intended recognition sequence of the assayed meganuclease and, in certain embodiments, variations of the intended recognition sequence in which one or more bases in one or both half-sites have been changed to a different base. Typically, the polynucleotide substrate is a double-stranded DNA molecule comprising a target site which has been synthesized and cloned into a vector. The polynucleotide substrate can be linear or circular, and typically comprises only one recognition sequence. The meganuclease is incubated with the polynucleotide substrate under appropriate conditions, and the resulting polynucleotides are analyzed by known methods for identifying cleavage products (e.g., electrophoresis or chromatography). If there is a single recognition sequence in a linear, double-strand DNA substrate, the meganuclease activity is detected by the appearance of two bands (products) and the disappearance of the initial full-length substrate band. In one embodiment, meganuclease activity can be assayed as described in, for example, Wang et al. (1997), *Nucleic Acid Res.*, 25: 3767-3776.

In other embodiments, the cleavage pattern of the meganuclease is determined using in vivo cleavage assays (see, e.g., U.S. Pat. Pub. No. 2006/0078552). In particular embodiments, the in vivo test is a single-strand annealing recombination test (SSA). This kind of test is known to those of skill in the art (Rudin et al. (1989), *Genetics* 122: 519-534; Fishman-Lobell et al. (1992), *Science* 258: 480-4).

As will be apparent to one of skill in the art, additional amino acid substitutions, insertions or deletions can be made to domains of the meganuclease enzymes other than those involved in DNA recognition and binding without complete loss of activity. Substitutions can be conservative substitutions of similar amino acid residues at structurally or functionally constrained positions, or can be non-conservative substitutions at positions which are less structurally or functionally constrained. Such substitutions, insertions and deletions can be identified by one of ordinary skill in the art by routine experimentation without undue effort. Thus, in some embodiments, the recombinant meganucleases of the invention include proteins having anywhere from 85% to 99% sequence similarity (e.g., 85%, 87.5%, 90%, 92.5%, 95%, 97.5%, 99%) to a reference meganuclease sequence. With respect to each of the wild-type I-CreI, I-MsoI, I-SceI and I-CeuI proteins, the most N-terminal and C-terminal sequences are not clearly visible in X-ray crystallography studies, suggesting that these positions are not structurally or functionally constrained. Therefore, these residues can be excluded from calculation of sequence similarity, and the following reference meganuclease sequences can be used: residues 2-153 of SEQ ID NO: 1 for I-CreI, residues 6-160 of SEQ ID NO: 6 for I-MsoI, residues 3-186 of SEQ ID NO: 9 for I-SceI, and residues 5-211 of SEQ ID NO: 12 for I-CeuI.

2.2 LAGLIDADG Family Meganucleases

The LAGLIDADG meganuclease family is composed of more than 200 members from a diverse phylogenetic group of host organisms. All members of this family have one or two copies of a highly conserved LAGLIDADG motif along with other structural motifs involved in cleavage of specific DNA sequences. Enzymes that have a single copy of the LAGLIDADG motif (i.e., mono-LAGLIDADG meganucleases) function as dimers, whereas the enzymes that have two copies of this motif (i.e., di-LAGLIDADG meganucleases) function as monomers.

All LAGLIDADG family members recognize and cleave relatively long sequences (>12 bp), leaving four nucleotide 3' overhangs. These enzymes also share a number of structural motifs in addition to the LAGLIDADG motif, including a similar arrangement of anti-parallel β-strands at the protein-DNA interface. Amino acids within these conserved structural motifs are responsible for interacting with the DNA bases to confer recognition sequence specificity. The overall structural similarity between some members of the family (e.g., I-CreI, I-MsoI, I-SceI and I-CeuI) has been elucidated by X-ray crystallography. Accordingly, the members of this family can be modified at particular amino acids within such structural motifs to change the over-all activity or sequence-specificity of the enzymes, and corresponding modifications can reasonable be expected to have similar results in other family members. See, generally, Chevalier et al. (2001), *Nucleic Acid Res.* 29(18): 3757-3774).

2.2.1 Meganucleases Derived from I-CreI

In one aspect, the present invention relates to rationally-designed meganucleases which are based upon or derived from the I-CreI meganuclease of *Chlamydomonas reinhardtii*. The wild-type amino acid sequence of the I-CreI meganuclease is shown in SEQ ID NO: 1, which corresponds to Genbank Accession #P05725. Two recognition sequence half sites of the wild-type I-CreI meganuclease from crystal structure PDB #1BP7 are shown below:

```
Position      -9-8-7-6-5-4-3-2-1
         5'-G A A A C T G T C T C A C G A C G T T T T G-3'  SEQ ID NO: 2

3'-C T T T G A C A G A G T G C T G C A A A A C-5'  SEQ ID NO: 3
Position                               -1-2-3-4-5-6-7-8-9
```

Note that this natural recognition sequence is not perfectly palindromic, even outside the central four base pairs. The two recognition sequence half-sites are shown in bold on their respective sense strands.

Wild-type I-CreI also recognizes and cuts the following perfectly palindromic (except for the central $N_1$—$N_4$ bases) sequence:

```
Position      -9-8-7-6-5-4-3-2-1
         5'-C A A A C T G T C G T G A G A C A G T T T G-3'  SEQ ID NO: 4

3'-G T T T G A C A G C A C T C T G T C A A A C-5'  SEQ ID NO: 5
Position                               -1-2-3-4-5-6-7-8-9
```

The palindromic sequence of SEQ ID NO: 4 and SEQ ID NO: 5 is considered to be a better substrate for the wild-type I-CreI because the enzyme binds this site with higher affinity and cleaves it more efficiently than the natural DNA sequence. For the purposes of the following disclosure, and with particular regard to the experimental results presented herein, this palindromic sequence cleaved by wild-type I-CreI is referred to as "WY" (see, e.g., FIG. 2(A)). The two recognition sequence half-sites are shown in bold on their respective sense strands.

FIG. 1(A) depicts the interactions of a wild-type I-CreI meganuclease homodimer with a double-stranded DNA recognition sequence, FIG. 1(B) shows the specific interactions between amino acid residues of the enzyme and bases at the −4 position of one half-site for a wild-type enzyme and one wild-type recognition sequence, and FIGS. 1(C)-(E) show the specific interactions between amino acid residues of the enzyme and bases at the −4 position of one half-site for three rationally-designed meganucleases of the invention with altered specificity at position −4 of the half-site.

Thus, the base preference at any specified base position of the half-site can be rationally altered to each of the other three base pairs using the methods disclosed herein. First, the wild type recognition surface at the specified base position is determined (e.g., by analyzing meganuclease-DNA complex co-crystal structures; or by computer modeling of the meganuclease-DNA complexes). Second, existing and potential contact residues are determined based on the distances between the β-carbons of the surrounding amino acid positions and the nucleic acid bases on each DNA strand at the specified base position. For example, and without limitation, as shown in FIG. 1(A), the I-CreI wild type meganuclease-DNA contact residues at position −4 involve a glutamine at position 26 which hydrogen bonds to an A base on the antisense DNA strand. Residue 77 was also identified as potentially being able to contact the −4 base on the DNA sense strand. The β-carbon of residue 26 is 5.9 Å away from N7 of the A base on the antisense DNA strand, and the β-carbon of residue 77 is 7.15 Å away from the C5-methyl of the T on the sense strand. According to the distance and base chemistry rules described herein, a C on the sense strand could hydrogen bond with a glutamic acid at position 77 and a G on the antisense strand could bond with glutamine at position 26 (mediated by a water molecule, as observed in the wild-type I-CreI crystal structure) (see FIG. 1(C)); a G on the sense strand could hydrogen bond with an arginine at position 77 and a C on the antisense strand could hydrogen bond with a glutamic acid at position 26 (see FIG. 1(D)); an A on the sense strand could hydrogen bond with a glutamine at position 77 and a T on the antisense strand could form hydrophobic contacts with an alanine at position 26 (see FIG. 1(E)). If the base specific contact is provided by position 77, then the wild-type contact, Q26, can be substituted (e.g., with a serine residue) to reduce or remove its influence on specificity. Alternatively, complementary mutations at positions 26 and 77 can be combined to specify a particular base pair (e.g., A26 specifies a T on the antisense strand and Q77 specifies an A on the sense strand (FIG. 1(E)). These predicted residue substitutions have all been validated experimentally.

Thus, in accordance with the invention, a substantial number of amino acid modifications to the DNA recognition domain of the I-CreI meganuclease have been identified which, singly or in combination, result in recombinant meganucleases with specificities altered at individual bases within the DNA recognition sequence half-site, such that these rationally-designed meganucleases have half-sites different from the wild-type enzyme. The amino acid modifications of I-CreI and the resulting change in recognition sequence half-site specificity are shown in Table 1:

TABLE 1

| | Favored Sense-Strand Base | | | | | | | | | | |
|---|---|---|---|---|---|---|---|---|---|---|---|
| Posn. | A | C | G | T | A/T | A/C | A/G | C/T | G/T | A/G/T | A/C/G/T |
| −1 | Y75 | R70* | K70 | Q70* | | | | T46* | | | G70 |
| | L75* | H75* | E70* | C70 | | | | | | | A70 |
| | C75* | R75* | E75* | L70 | | | | | | | S70 |
| | Y139* | H46* | E46* | Y75* | | | | | | | G46* |
| | C46* | K46* | D46* | Q75* | | | | | | | |
| | A46* | R46* | | H75* | | | | | | | |
| | | | | H139 | | | | | | | |
| | | | | Q46* | | | | | | | |
| | | | | H46* | | | | | | | |
| −2 | Q70 | E70 | H70 | Q44* | C44* | | | | | | |
| | T44* | D70 | D44* | | | | | | | | |
| | A44* | K44* | E44* | | | | | | | | |
| | V44* | R44* | | | | | | | | | |
| | I44* | | | | | | | | | | |
| | L44* | | | | | | | | | | |
| | N44* | | | | | | | | | | |
| −3 | Q68 | E68 | R68 | M68 | | H68 | | Y68 | K68 | | |
| | C24* | F68 | | C68 | | | | | | | |
| | I24* | K24* | | L68 | | | | | | | |
| | | R24* | | F68 | | | | | | | |
| −4 | A26* | E77 | R77 | | | | | S77 | | | S26* |
| | Q77 | K26* | E26* | | | | | Q26* | | | |
| −5 | | E42 | R42 | | K28* | C28* | | | | | M66 |
| | | | | | | Q42 | | | | | K66 |
| −6 | Q40 | E40 | R40 | C40 | A40 | | | | | | S40 |
| | C28* | R28* | | I40 | A79 | | | | | | S28* |
| | | | | V40 | A28* | | | | | | |
| | | | | C79 | H28* | | | | | | |
| | | | | I79 | | | | | | | |
| | | | | V79 | | | | | | | |
| | | | | Q28* | | | | | | | |
| −7 | N30* | E38 | K38 | I38 | | | C38 | | | | H38 |
| | Q38 | K30* | R38 | L38 | | | | | | | N38 |
| | | R30* | E30* | | | | | | | | Q30* |
| −8 | F33 | E33 | F33 | L33 | | R32* | R33 | | | | |
| | Y33 | D33 | H33 | V33 | | | | | | | |
| | | | | I33 | | | | | | | |
| | | | | F33 | | | | | | | |
| | | | | C33 | | | | | | | |
| −9 | | E32 | R32 | L32 | | | | D32 | | | S32 |
| | | | K32 | V32 | | | | I32 | | | N32 |
| | | | | A32 | | | | | | | H32 |
| | | | | C32 | | | | | | | Q32 |
| | | | | | | | | | | | T32 |

Bold entries are wild-type contact residues and do not constitute "modifications" as used herein.
An asterisk indicates that the residue contacts the base on the antisense strand.

2.2.2 Meganucleases Derived from I-MsoI

In another aspect, the present invention relates to rationally-designed meganucleases which are based upon or derived from the I-MsoI meganuclease of *Monomastix* sp. The wild-type amino acid sequence of the I-MsoI meganuclease is shown in SEQ ID NO: 6, which corresponds to Genbank Accession #AAL34387. Two recognition sequence half-sites of the wild-type I-MsoI meganuclease from crystal structure PDB #1M5X are shown below:

```
Position     -9-8-7-6-5-4-3-2-1
          5'-C A G A A C G T C G T G A G A C A G T T C C-3' SEQ ID NO: 7

3'-G T C T T G C A G C A C T C T G T C A A G G-5' SEQ ID NO: 8
Position                         -1-2-3-4-5-6-7-8-9
```

Note that the recognition sequence is not perfectly palindromic, even outside the central four base pairs. The two recognition sequence half-sites are shown in bold on their respective sense strands.

In accordance with the invention, a substantial number of amino acid modifications to the DNA recognition domain of the I-MsoI meganuclease have been identified which, singly or in combination, can result in recombinant meganucleases with specificities altered at individual bases within the DNA recognition sequence half-sites, such that these rationally-designed meganucleases have recognition sequences different from the wild-type enzyme. Amino acid modifications of I-MsoI and the predicted change in recognition sequence half-site specificity are shown in Table 2:

TABLE 2

| Position | Favored Sense-Strand Base | | | |
|---|---|---|---|---|
| | A | C | G | T |
| −1 | K75* | D77 | K77 | C77 |
| | Q77 | E77 | R77 | L77 |
| | A49* | K49* | E49* | Q79* |
| | C49* | R75* | E79* | |
| | K79* | K75* | | |
| | | R79* | | |
| | | K79* | | |
| −2 | Q75 | E75 | K75 | A75 |
| | K81 | D75 | E47* | C75 |
| | C47* | R47* | E81* | V75 |
| | I47* | K47* | | I75 |
| | L47* | K81* | | T75 |
| | | R81* | | Q47* |
| | | | | Q81* |
| −3 | Q72 | E72 | R72 | K72 |
| | C26* | Y72 | K72 | Y72 |
| | L26* | H26* | Y26* | H26* |
| | V26* | K26* | F26* | |
| | A26* | R26* | | |
| | I26* | | | |
| −4 | K28 | K28* | R83 | K28 |
| | Q83 | R28* | K83 | K83 |
| | | E83 | | Q28* |
| −5 | K28 | K28* | R45 | Q28* |
| | C28* | R28* | E28* | |
| | L28* | | | |
| | I28* | | | |
| −6 | I30* | E43 | R43 | K43 |
| | V30* | E85 | K43 | I85 |
| | S30* | K30* | K85 | V85 |
| | L30* | R30* | R85 | L85 |
| | Q43 | | E30* | Q30* |
| | | | D30* | |
| −7 | Q41 | E32 | R32 | K32 |
| | | E41 | R41 | M41 |
| | | | K41 | L41 |
| | | | | I41 |
| −8 | Y35 | E32 | R32 | K32 |
| | K35 | | K32 | K35 |
| | | | K35 | |
| | | | R35 | |
| −9 | N34 | D34 | K34 | S34 |
| | H34 | E34 | R34 | C34 |
| | | S34 | H34 | V34 |
| | | | | T34 |
| | | | | A34 |

Bold entries are represent wild-type contact residues and do not constitute "modifications" as used herein.
An asterisk indicates that the residue contacts the base on the antisense strand.

2.2.3 Meganucleases Derived from I-SceI

In another aspect, the present invention relates to rationally-designed meganucleases which are based upon or derived from the I-SceI meganuclease of *Saccharomyces cerevisiae*. The wild-type amino acid sequence of the I-SceI meganuclease is shown in SEQ ID NO: 9, which corresponds to Genbank Accession #CAA09843. The recognition sequence of the wild-type I-SceI meganuclease from crystal structure PDB #1R7M is shown below:

```
Sense      5'-T T A C C C T G T  T  A  T  C  C  C  T  A  G-3' SEQ ID NO: 10

Antisense  3'-A A T G G G A C A  A  T  A  G  G  G  A  T  C-5' SEQ ID NO: 11
Position      1 2 3 4 5 6 7 8 9 10 11 12 13 14 15 16 17 18
```

Note that the recognition sequence is non-palindromic and there are not four base pairs separating half-sites.

In accordance with the invention, a substantial number of amino acid modifications to the DNA recognition domain of the I-SceI meganuclease have been identified which, singly or in combination, can result in recombinant meganucleases with specificities altered at individual bases within the DNA recognition sequence, such that these rationally-designed meganucleases have recognition sequences different from the wild-type enzyme. The amino acid modifications of I-SceI and the predicted change in recognition sequence specificity are shown in Table 3:

TABLE 3

| | Favored Sense-Strand Base | | | |
|---|---|---|---|---|
| Position | A | C | G | T |
| 4 | K50 | R50* | E50* | K57 |
| | K50* | R57 | M57 | |
| | E57 | K57 | Q50* | |
| 5 | K48 | R48* | E48* | Q48* |
| | Q102 | K48* | K102 | C102 |
| | | E102 | R102 | L102 |
| | | E59 | | V102 |
| 6 | K59 | R59* | K84 | Q59* |
| | | K59* | E59* | Y46 |
| 7 | C46* | R46* | K86 | K68 |
| | L46* | K46* | R86 | C86 |
| | V46* | E86 | E46* | L86 |
| | | | | Q46* |
| 8 | K61* | E88 | E61* | K88 |
| | S61* | R61* | R88 | Q61* |
| | V61* | H61* | K88 | H61* |
| | A61* | | | |
| | L61* | | | |
| 9 | T98* | R98* | E98* | Q98* |
| | C98* | K98* | D98* | |
| | V98* | | | |
| | L98* | | | |
| 10 | V96* | K96* | D96* | Q96* |
| | C96* | R96* | E96* | |
| | A96* | | | |
| 11 | C90* | K90* | E90* | Q90* |
| | L90* | R90* | | |
| 12 | Q193 | E165 | K165 | C165 |
| | | E193 | R165 | L165 |
| | | D193 | | C193 |
| | | | | V193 |

TABLE 3-continued

| | Favored Sense-Strand Base | | | |
|---|---|---|---|---|
| Position | A | C | G | T |
| 13 | C193* | K193* | E193* | Q193* |
| | L193* | R193* | D193* | C163 |
| | | | | A193 |
| | | | | T193 |
| | | | | S193 |
| 14 | L192* | D192 | K163 | L163 |
| | C192* | E161 | R192 | K161 |
| | | R192* | K147 | Q192* |
| | | K192* | K161 | |
| | | | R161 | |
| | | | R197 | |
| | | | D192* | |
| | | | E192* | |
| 15 | | E151 | K151 | C151 |
| | | | | L151 |
| | | | | K151 |
| 17 | N152* | K152* | N152* | Q152* |
| | S152* | K150* | S152* | Q150* |
| | C150* | | D152* | |
| | L150* | | D150* | |
| | V150* | | E150* | |
| | T150* | | | |
| 18 | K155* | R155* | E155* | H155* |
| | C155* | K155* | | Y155* |

Bold entries are wild-type contact residues and do not constitute "modifications" as used herein.
An asterisk indicates that the residue contacts the base on the antisense strand.

2.2.4 Meganucleases Derived from I-CeuI

In another aspect, the present invention relates to rationally-designed meganucleases which are based upon or derived from the I-CeuI meganuclease of *Chlamydomonas eugametos*. The wild-type amino acid sequence of the I-CeuI meganuclease is shown in SEQ ID NO: 12, which corresponds to Genbank Accession #P32761. Two recognition sequence half sites of the wild-type I-CeuI meganuclease from crystal structure PDB #2EX5 are shown below:

```
Position       -9-8-7-6-5-4-3-2-1
            5'-A T A A C G G T C C T A A G G T A G C G A A-3' SEQ ID NO: 13

3'-T A T T G C C A G G A T T C C A T C G C T T-5' SEQ ID NO: 14
Position                          -1-2-3-4-5-6-7-8-9
```

Note that the recognition sequence is non-palindromic, even outside the central four base pairs, despite the fact that I-CeuI is a homodimer, due to the natural degeneracy in the I-CeuI recognition interface (Spiegel et al. (2006), *Structure* 14:869-80). The two recognition sequence half-sites are shown in bold on their respective sense strands.

In accordance with the invention, a substantial number of amino acid modifications to the DNA recognition domain of the I-CeuI meganuclease have been identified which, singly or in combination, result in recombinant meganucleases with specificities altered at individual bases within the DNA recognition sequence half-site, such that these rationally-designed meganucleases can have recognition sequences different from the wild-type enzyme. The amino acid modifications of I-CeuI and the predicted change in recognition sequence specificity are shown in Table 4:

TABLE 4

| Position | Favored Sense-Strand Base | | | |
|---|---|---|---|---|
| | A | C | G | T |
| −1 | C92* | K116* | E116* | Q116* |
| | A92* | R116* | E92* | Q92* |
| | V92* | D116* | | |
| | | K92* | | |
| −2 | Q117 | E117 | K117 | C117 |
| | C90* | D117 | R124 | V117 |
| | L90* | R174* | K124 | T117 |
| | V90* | K124* | E124* | Q90* |
| | | K90* | E90* | |
| | | R90* | D90* | |
| | | K68* | | |
| −3 | C70* | K70* | E70* | Q70* |
| | V70* | | E88* | |
| | T70* | | | |
| | L70* | | | |
| | K70* | | | |
| −4 | Q126 | E126 | R126 | K126 |
| | N126 | D126 | K126 | L126 |
| | K88* | R88* | E88* | Q88* |
| | L88* | K88* | D88* | |
| | C88* | K72* | | |
| | C72* | | | |
| | L72* | | | |
| | V72* | | | |
| −5 | C74* | K74* | E74* | C128 |
| | L74* | | K128 | L128 |
| | V74* | | R128 | V128 |
| | T74* | | E128 | T128 |
| −6 | Q86 | D86 | K128 | K86 |
| | | E86 | R128 | C86 |
| | | R84* | R86 | L86 |
| | | K84* | K86 | |
| | | | E84* | |
| −7 | L76* | R76* | E76* | H76* |
| | C76* | K76* | R84 | Q76* |
| | K76* | H76* | | |
| −8 | Y79 | D79 | R79 | C79 |
| | R79 | E79 | K79 | L79 |
| | Q76 | D76 | K76 | V79 |
| | | E76 | R76 | L76 |
| −9 | Q78 | D78 | R78 | K78 |
| | N78 | E78 | K78 | V78 |
| | H78 | | H78 | L78 |
| | K78 | | | C78 |
| | | | | T78 |

Bold entries are wild-type contact residues and do not constitute "modifications" as used herein.
An asterisk indicates that the residue contacts the base on the antisense strand.

2.2.5 Specifically-Excluded Recombinant Meganucleases

The present invention is not intended to embrace certain recombinant meganucleases which have been described in the prior art, and which have been developed by alternative methods. These excluded meganucleases include those described by Arnould et al. (2006), *J. Mol. Biol.* 355: 443-58; Sussman et al. (2004), *J. Mol. Biol.* 342: 31-41; Chames et al. (2005), *Nucleic Acids Res.* 33: e178; Seligman et al. (2002), *Nucleic Acids Res.* 30: 3870-9; and Ashworth et al. (2006), *Nature* 441(7093):656-659; the entire disclosures of which are hereby incorporated by reference, including recombinant meganucleases based on I-CreI with single substitutions selected from C33, R33, A44, H33, K32, F33, R32, A28, A70, E33, V33, A26, and R66. Also excluded are recombinant meganucleases based on I-CreI with three substitutions selected from A68/N70/N75 and D44/D70/N75, or with four substitutions selected from K44/T68/G60/N75 and R44/A68/T70/N75. Lastly, specifically excluded is the recombinant meganuclease based on I-MsoI with the pair of substitutions L28 and R83. These substitutions or combinations of substitutions are referred to herein as the "excluded modifications."

2.2.6 Meganucleases with Multiple Changes in the Recognition Sequence Half-Site In another aspect, the present invention relates to rationally-designed meganucleases which are produced by combining two or more amino acid modifications as described in sections 2.2.1-2.2.4 above, in order to alter half-site preference at two or more positions in a DNA recognition sequence half-site. For example, without limitation, and as more fully described below, the enzyme DJ1 was derived from I-CreI by incorporating the modifications R30/E38 (which favor C at position −7), R40 (which favors G at position −6), R42 (which favors at G at position −5), and N32 (which favors complete degeneracy at position −9). The rationally-designed DJ1 meganuclease invariantly recognizes $C_{-7} G_{-6} G_{-5}$ compared to the wild-type preference for $A_{-7} A_{-6} C_{-5}$, and has increased tolerance for A at position −9.

The ability to combine residue substitutions that affect different base positions is due in part to the modular nature of the LAGLIDADG meganucleases. A majority of the base contacts in the LAGLIDADG recognition interfaces are made by individual amino acid side chains, and the interface is relatively free of interconnectivity or hydrogen bonding networks between side chains that interact with adjacent bases. This generally allows manipulation of residues that interact with one base position without affecting side chain interactions at adjacent bases. The additive nature of the mutations listed in sections 2.2.1-2.2.4 above is also a direct result of the method used to identify these mutations. The method predicts side chain substitutions that interact directly with a single base. Interconnectivity or hydrogen bonding networks between side chains is generally avoided to maintain the independence of the substitutions within the recognition interface.

Certain combinations of side chain substitutions are completely or partially incompatible with one another. When an incompatible pair or set of amino acids are incorporated into a rationally-designed meganuclease, the resulting enzyme will have reduced or eliminated catalytic activity. Typically, these incompatibilities are due to steric interference between the side chains of the introduced amino acids and activity can be restored by identifying and removing this interference. Specifically, when two amino acids with large side chains (e.g., amino acids from group 2 or 3) are incorporated at amino acid positions that are adjacent to one another in the meganuclease structure (e.g., positions 32 and 33, 28 and 40, 28 and 42, 42 and 77, or 68 and 77 in the case of meganucleases derived from I-CreI), it is likely that these two amino acids will interfere with one another and reduce enzyme activity. This interference be eliminated by substituting one or both incompatible amino acids to an amino acid with a smaller side chain (e.g., group 1 or group 2). For example, in rationally-designed meganucleases derived from I-CreI, K28 interferes with both R40 and R42. To maximize enzyme activity, R40 and R42 can be combined with a serine or aspartic acid at position 28.

Combinations of amino substitutions, identified as described herein, can be used to rationally alter the specificity of a wild-type meganuclease (or a previously modified meganuclease) from an original recognition sequence to a desired recognition sequence which may be present in a nucleic acid of interest (e.g., a genome). FIG. 2A, for example, shows the "sense" strand of the I-CreI meganuclease recognition sequence WT (SEQ ID NO: 4) as well as a number of other sequences for which a rationally-designed meganuclease would be useful. Conserved bases between the WT recognition sequence and the desired recognition sequence are shaded. In accordance with the invention, recombinant meganucleases based on the I-CreI meganuclease can be rationally-designed for each of these desired recognition sequences, as well as any others, by suitable amino acid substitutions as described herein.

3. Rationally-Designed Meganucleases with Altered DNA-Binding Affinity

As described above, the DNA-binding affinity of the recombinant meganucleases of the invention can be modulated by altering certain amino acids that form the contact surface with the phosphodiester backbone of DNA. The contact surface comprises those amino acids in the enzyme with β-carbons less than 9 Å from the DNA backbone, and with side chains oriented toward the DNA, irrespective of whether the residues make contacts with the DNA backbone in the wild-type meganuclease-DNA complex. Because DNA-binding is a necessary precursor to enzyme activity, increases/decreases in DNA-binding affinity have been shown to cause increases/decreases, respectively, in enzyme activity. However, increases/decreases in DNA-binding affinity also have been shown to cause decreases/increases in the meganuclease sequence-specificity. Therefore, both activity and specificity can be modulated by modifying the phosphodiester backbone contacts.

Specifically, to increase enzyme activity/decrease enzyme specificity:

(i) Remove electrostatic repulsion between the enzyme and DNA backbone. If an identified amino acid has a negatively-charged side chain (e.g., aspartic acid, glutamic acid) which would be expected to repulse the negatively-charged DNA backbone, the repulsion can be eliminated by substituting an amino acid with an uncharged or positively-charged side chain, subject to effects of steric interference. An experimentally verified example is the mutation of glutamic acid 80 in I-CreI to glutamine.

(ii) Introduce electrostatic attraction interaction between the enzyme and the DNA backbone. At any of the positions of the contact surface, the introduction of an amino acid with a positively-charged side chain (e.g., lysine or arginine) is expected to increase binding affinity, subject to effects of steric interference.

(iii) Introduce a hydrogen-bond between the enzyme and the DNA backbone. If an amino acid of the contact surface does not make a hydrogen bond with the DNA backbone because it lacks an appropriate hydrogen-bonding functionality or has a side chain that is too short, too long, and/or too inflexible to interact with the DNA backbone, a polar amino acid capable of donating a hydrogen bond (e.g., serine, threonine, tyrosine, histidine, glutamine, asparagine, lysine, cysteine, or arginine) with the appropriate length and flexibility can be introduced, subject to effects of steric interference.

Specifically, to decrease enzyme activity/increase enzyme specificity:

(i) Introduce electrostatic repulsion between the enzyme and the DNA backbone. At any of the positions of the contact surface, the introduction of an amino acid with a negatively-charged side chain (e.g., glutamic acid, aspartic acid) is expected to decrease binding affinity, subject to effects of steric interference.

(ii) Remove electrostatic attraction between the enzyme and DNA. If any amino acid of the contact surface has a positively-charged side chain (e.g., lysine or arginine) that interacts with the negatively-charged DNA backbone, this favorable interaction can be eliminated by substituting an amino acid with an uncharged or negatively-charged side chain, subject to effects of steric interference. An experimentally verified example is the mutation of lysine 116 in I-CreI to aspartic acid.

(iii) Remove a hydrogen-bond between the enzyme and the DNA backbone. If any amino acid of the contact surface makes a hydrogen bond with the DNA backbone, it can be substituted to an amino acid that would not be expected to make a similar hydrogen bond because its side chain is not appropriately functionalized or it lacks the necessary length/flexibility characteristics.

For example, in some recombinant meganucleases based on I-CreI, the glutamic acid at position 80 in the I-CreI meganuclease is altered to either a lysine or a glutamine to increase activity. In another embodiment, the tyrosine at position 66 of I-CreI is changed to arginine or lysine, which increases the activity of the meganuclease. In yet another embodiment, enzyme activity is decreased by changing the lysine at position 34 of I-CreI to aspartic acid, changing the tyrosine at position 66 to aspartic acid, and/or changing the lysine at position 116 to aspartic acid.

The activities of the recombinant meganucleases can be modulated such that the recombinant enzyme has anywhere from no activity to very high activity with respect to a particular recognition sequence. For example, the DJ1 recombinant meganuclease when carrying glutamic acid mutation at position 26 loses activity completely. However, the combination of the glutamic acid substitution at position 26 and a glutamine substitution at position 80 creates a recombinant meganuclease with high specificity and activity toward a guanine at −4 within the recognition sequence half-site (see FIG. 1(D)).

In accordance with the invention, amino acids at various positions in proximity to the phosphodiester DNA backbone can be changed to simultaneously affect both meganuclease activity and specificity. This "tuning" of the enzyme specificity and activity is accomplished by increasing or decreasing the number of contacts made by amino acids with the phosphodiester backbone. A variety of contacts with the phosphodiester backbone can be facilitated by amino acid side chains. In some embodiments, ionic bonds, salt bridges, hydrogen bonds, and steric hindrance affect the association of amino acid side chains with the phosphodiester backbone. For example, for the I-CreI meganuclease, alteration of the lysine at position 116 to an aspartic acid removes a salt bridge between nucleic acid base pairs at positions −8 and −9, reducing the rate of enzyme cleavage but increasing the specificity.

The residues forming the backbone contact surface of each of the wild-type I-CreI (SEQ ID NO: 1), I-MsoI (SEQ ID NO: 6), I-SceI (SEQ ID NO: 9) and I-CeuI (SEQ ID NO: 12) meganucleases are identified in Table 5 below:

TABLE 5

| I-CreI | I-MsoI | I-SceI | I-CeuI |
|---|---|---|---|
| P29, K34, T46, K48, R51, V64, Y66, E80, I81, K82, L112, K116, D137, K139, T140, T143 | K36, Q41, R51, N70, I85, G86, S87, T88, H89, Y118, Q122, K123, Q139, K143, R144, E147, S150, N152 | N15, N17, L19, K20, K23, K63, L80, S81, H84, L92, N94, N120, K122, K148, Y151, K153, T156, N157, S159, N163, Q165, S166, Y188, K190, I191, K193, N194, K195, Y199, D201, S202, Y222, K223 | K21, D25, K28, K31, S68, N70, H94, R112, R114, S117, N120, D128, N129, R130, H172 |

To increase the affinity of an enzyme and thereby make it more active/less specific:
(1) Select an amino acid from Table 5 for the corresponding enzyme that is either negatively-charged (D or E), hydrophobic (A, C, F, G, I, L, M, P, V, W, Y), or uncharged/polar (H, N, Q, S, T).
(2) If the amino acid is negatively-charged or hydrophobic, mutate it to uncharged/polar (less effect) or positively-charged (K or R, more effect).
(3) If the amino acid is uncharged/polar, mutate it to positively-charged.

To decrease the affinity of an enzyme and thereby make it less active/more specific:
(1) Select an amino acid from Table 5 for the corresponding enzyme that is either positively-charged (K or R), hydrophobic (A, C, F, G, I, L, M, P, V, W, Y), or uncharged/polar (H, N, Q, S, T).
(2) If the amino acid is positively-charged, mutate it to uncharged/polar (less effect) or negatively-charged (more effect).
(3) If the amino acid is hydrophobic or uncharged/polar, mutate it to negatively-charged.

4. Heterodimeric Meganucleases

In another aspect, the invention provides meganucleases which are heterodimers formed by the association of two monomers, one of which may be a wild-type and one or both of which may be a non-naturally-occurring or recombinant form. For example, wild-type I-CreI meganuclease is normally a homodimer composed of two monomers that each bind to one half-site in the pseudo-palindromic recognition sequence. A heterodimeric recombinant meganuclease can be produced by combining two meganucleases that recognize different half-sites, for example by co-expressing the two meganucleases in a cell or by mixing two meganucleases in solution. The formation of heterodimers can be favored over the formation of homodimers by altering amino acids on each of the two monomers that affect their association into dimers. In particular embodiments, certain amino acids at the interface of the two monomers are altered from negatively-charged amino acids (D or E) to positively-charged amino acids (K or R) on a first monomer and from positively-charged amino acids to negatively-charged amino acids on a second monomer (Table 6). For example, in the case of meganucleases derived from I-CreI, lysines at positions 7 and 57 are mutated to glutamic acids in the first monomer and glutamic acids at positions 8 and 61 are mutated to lysines in the second monomer. The result of this process is a pair of monomers in which the first monomer has an excess of positively-charged residues at the dimer interface and the second monomer has an excess of negatively-charged residues at the dimer interface. The first and second monomer will, therefore, associate preferentially over their identical monomer pairs due to the electrostatic interactions between the altered amino acids at the interface.

TABLE 6

| I-CreI: First Monomer Substitutions | I-CreI: Second Monomer Substitutions |
|---|---|
| K7 to E7 or D7<br>K57 to E57 or D57<br>K96 to E96 or D96 | E8 to K8 or R8<br>E61 to K61 or R61 |
| I-MsoI: First Monomer Substitutions | I-MsoI: Second Monomer Substitutions |
| R302 to E302 or D302 | D20 to K60 or R60<br>E11 to K11 or R11<br>Q64 to K64 or R64 |
| I-CeuI: First Monomer Substitutions | I-CeuI: Second Monomer Substitutions |
| R93 to E93 or D93 | E152 to K152 or R152 |

Alternatively, or in addition, certain amino acids at the interface of the two monomers can be altered to sterically hinder homodimer formation. Specifically, amino acids in the dimer interface of one monomer are substituted with larger or bulkier residues that will sterically prevent the homodimer. Amino acids in the dimer interface of the second monomer optionally can be substituted with smaller residues to compensate for the bulkier residues in the first monomer and remove any clashes in the heterodimer, or can be unmodified.

In another alternative or additional embodiment, an ionic bridge or hydrogen bond can be buried in the hydrophobic core of a heterodimeric interface. Specifically, a hydrophobic residue on one monomer at the core of the interface can be substituted with a positively charged residue. In addition, a hydrophobic residue on the second monomer, that interacts in the wild type homodimer with the hydrophobic residue substituted in the first monomer, can be substituted with a negatively charged residue. Thus, the two substituted residues can form an ionic bridge or hydrogen bond. At the same time, the electrostatic repulsion of an unsatisfied charge buried in a hydrophobic interface should disfavor homodimer formation.

Finally, as noted above, each monomer of the heterodimer can have different amino acids substituted in the DNA recognition region such that each has a different DNA half-site and the combined dimeric DNA recognition sequence is non-palindromic.

5. Methods of Producing Recombinant Cells and Organisms

Aspects of the present invention further provide methods for producing recombinant, transgenic or otherwise genetically-modified cells and organisms using rationally-designed meganucleases. Thus, in certain embodiments, recombinant meganucleases are developed to specifically cause a double-stranded break at a single site or at relatively few sites in the genomic DNA of a cell or an organism to allow for precise insertion(s) of a sequence of interest by homologous recombination. In other embodiments, recombinant meganucleases are developed to specifically cause a double-stranded break at a single site or at relatively few sites in the genomic DNA of a cell or an organism to either (a) allow for rare insertion(s) of a sequence of interest by non-homologous end joining or (b) allow for the disruption of the target sequence by non-homologous end joining As used herein with respect to homologous recombination or non-homologous end joining of sequences of interest, the term "insertion" means the ligation of a sequence of interest into a chromosome such that the sequence of interest is integrated into the chromosome. In the case of homologous recombination, an inserted sequence can replace an endogenous sequence, such that the original DNA is replaced by exogenous DNA of equal length, but with an altered nucleotide sequence. Alternatively, an inserted sequence can include more or fewer bases than the sequence it replaces.

Therefore, in accordance with this aspect of the invention, the recombinant organisms include, but are not limited to, monocot plant species such as rice, wheat, corn (maize) and rye, and dicot species such as legumes (e.g., kidney beans, soybeans, lentils, peanuts, peas), alfalfa, clover, tobacco and *Arabidopsis* species. In addition, the recombinant organisms can include, but are not limited to, animals such as humans and non-human primates, horses, cows, goats, pigs, sheep, dogs, cats, guinea pigs, rats, mice, lizards, fish and insects such as *Drosophila* species. In other embodiments, the organism is a fungus such as a *Candida, Neurospora* or *Saccharomyces* species.

In some embodiments, the methods of the invention involve the introduction of a sequence of interest into a cell such as a germ cell or stem cell that can become a mature recombinant organism or allow the resultant genetically-modified organism to give rise to progeny carrying the inserted sequence of interest in its genome.

Meganuclease proteins can be delivered into cells to cleave genomic DNA, which allows for homologous recombination or non-homologous end joining at the cleavage site with a sequence of interest, by a variety of different mechanisms known in the art. For example, the recombinant meganuclease protein can introduced into a cell by techniques including, but not limited to, microinjection or liposome transfections (see, e.g., Lipofectamine™, Invitrogen Corp., Carlsbad, Calif.). The liposome formulation can be used to facilitate lipid bilayer fusion with a target cell, thereby allowing the contents of the liposome or proteins associated with its surface to be brought into the cell. Alternatively, the enzyme can be fused to an appropriate uptake peptide such as that from the HIV TAT protein to direct cellular uptake (see, e.g., Hudecz et al. (2005), *Med. Res. Rev.* 25: 679-736).

Alternatively, gene sequences encoding the meganuclease protein are inserted into a vector and transfected into a eukaryotic cell using techniques known in the art (see, e.g., Ausubel et. al., *Current Protocols in Molecular Biology*, Wiley 1999). The sequence of interest can be introduced in the same vector, a different vector, or by other means known in the art.

Non-limiting examples of vectors for DNA transfection include virus vectors, plasmids, cosmids, and YAC vectors. Transfection of DNA sequences can be accomplished by a variety of methods known to those of skill in the art. For instance, liposomes and immunoliposomes are used to deliver DNA sequences to cells (see, e.g., Lasic et al. (1995), *Science* 267: 1275-76). In addition, viruses can be utilized to introduce vectors into cells (see, e.g., U.S. Pat. No. 7,037, 492). Alternatively, transfection strategies can be utilized such that the vectors are introduced as naked DNA (see, e.g., Rui et al. (2002), *Life Sci.* 71(15): 1771-8).

General methods for delivering nucleic acids into cells include: (1) chemical methods (Graham et al. (1973), *Virology* 54(2):536-539; Zatloukal et al. (1992), *Ann. N.Y. Acad. Sci.*, 660:136-153; (2) physical methods such as microinjection (Capecchi (1980), *Cell* 22(2):479-488, electroporation (Wong et al. (1982), *Biochim. Biophys. Res. Commun.* 107 (2):584-587; Fromm et al. (1985), *Proc. Nat'l Acad. Sci. USA* 82(17):5824-5828; U.S. Pat. No. 5,384,253) and ballistic injection (Johnston et al. (1994), *Methods Cell. Biol.* 43(A): 353-365; Fynan et al. (1993), *Proc. Nat'l Acad. Sci. USA* 90(24): 11478-11482); (3) viral vectors (Clapp (1993), *Clin. Perinatol.* 20(1): 155-168; Lu et al. (1993), *J. Exp. Med.* 178(6): 2089-2096 Eglitis et al. (1988), *Avd. Exp. Med. Biol.* 241:19-27; Eglitis et al. (1988), *Biotechniques* 6(7):608-614); and (4) receptor-mediated mechanisms (Curiel et al. (1991), *Proc. Nat'l Acad. Sci. USA* 88(19):8850-8854; Curiel et al. (1992), *Hum. Gen. Ther.* 3(2):147-154; Wagner et al. (1992), *Proc. Nat'l Acad. Sci. USA* 89 (13): 6099-6103).

In certain embodiments, a genetically-modified plant is produced, which contains the sequence of interest inserted into the genome. In certain embodiments, the genetically-modified plant is produced by transfecting the plant cell with DNA sequences corresponding to the recombinant meganuclease and the sequence of interest, which may or may not be flanked by the meganuclease recognition sequences and/or sequences substantially identical to the target sequence. In other embodiments, the genetically-modified plant is produced by transfecting the plant cell with DNA sequences corresponding to the recombinant meganuclease only, such that cleavage promotes non-homologous end joining and disrupts the target sequence containing the recognition sequence. In such embodiments, the meganuclease sequences are under the control of regulatory sequences that allow for expression of the meganuclease in the host plant cells. These regulatory sequences include, but are not limited to, constitutive plant promoters such as the NOS promoter, chemically-inducible gene promoters such as the dexamethasone-inducible promoter (see, e.g., Gremillon et al. (2004), *Plant J.* 37:218-228), and plant tissue specific promoters such as the LGC1 promoter (see, e.g., Singh et al. (2003), FEBS Lett. 542:47-52).

Suitable methods for introducing DNA into plant cells include virtually any method by which DNA can be introduced into a cell, including but not limited to *Agrobacterium* infection, PEG-mediated transformation of protoplasts (Omirulleh et al. (1993), *Plant Molecular Biology*, 21:415-428), desiccation/inhibition-mediated DNA uptake, electroporation, agitation with silicon carbide fibers, ballistic injection or microprojectile bombardment, and the like.

In other embodiments, a genetically-modified animal is produced using a recombinant meganuclease. As with plant cells, the nucleic acid sequences can be introduced into a germ cell or a cell that will eventually become a transgenic organism. In some embodiments, the cell is a fertilized egg, and exogenous DNA molecules can be injected into the pronucleus of the fertilized egg. The micro-injected eggs are then transferred into the oviducts of pseudopregnant foster mothers and allowed to develop. The recombinant meganuclease is expressed in the fertilized egg (e.g., under the control of a constitutive promoter, such as 3-phosphoglycerate kinase), and facilitates homologous recombination of the sequence of interest into one or a few discrete sites in the genome. Alternatively, the genetically-modified animals can be obtained by utilizing recombinant embryonic stem ("ES") cells for the generation of the transgenics, as described by Gossler et al. (1986), *Proc. Natl. Acad. Sci. USA* 83:9065 9069.

In certain embodiments, a recombinant mammalian expression vector is capable of directing tissue-specific expression of the nucleic acid preferentially in a particular cell type. Tissue-specific regulatory elements are known in the art. Non-limiting examples of suitable tissue-specific promoters include the albumin promoter (liver-specific; Pinkert et al. (1987), *Genes Dev.* 1: 268-277), lymphoid-specific promoters (Calame and Eaton (1988), *Adv. Immunol.* 43: 235-275), in particular promoters of T cell receptors (Winoto and Baltimore (1989), *EMBO J.* 8: 729-733) and immunoglobulins (Banerji et al. (1983), *Cell* 33: 729-740; Queen and Baltimore (1983), *Cell* 33: 741-748), neuron-specific promoters (e.g., the neurofilament promoter; Byrne and Ruddle (1989), *Proc. Natl. Acad. Sci. USA* 86: 5473-5477), pancreas-specific promoters (Edlund et al. (1985), *Science* 230: 912-916), and mammary gland-specific promoters (e.g., milk whey promoter; U.S. Pat. No. 4,873,316 and European Pat. Pub. EP 0 264 166). Developmentally-regulated promoters are also encompassed, e.g., the murine hox promoters (Kessel and Gruss (1990), *Science* 249: 374-379) and the α-fetoprotein promoter (Campes and Tilghman (1989), *Genes Dev.* 3: 537-546).

In certain embodiments, a rationally-designed meganuclease may be tagged with a peptide epitope (e.g., an HA, FLAG, or Myc epitope) to monitor expression levels or localization. In some embodiments, the meganuclease may be fused to a sub-cellular localization signal such as a nuclear-localization signal (e.g., the nuclear localization signal from SV40) or chloroplast or mitochondrial localization signals. In other embodiments, the meganuclease may be fused to a nuclear export signal to localize it to the cytoplasm. The meganuclease may also be fused to an unrelated protein or protein domain such as a protein that stimulates DNA-repair or homologous recombination (e.g., recA, RAD51, RAD52, RAD54, RAD57 or BRCA2).

6. Methods for Gene Therapy

Aspects of the invention allow for the use of recombinant meganuclease for gene therapy. As used herein, "gene therapy" means therapeutic treatments that comprise introducing into a patient a functional copy of at least one gene, or gene regulatory sequence such as a promoter, enhancer, or silencer to replace a gene or gene regulatory region that is defective in its structure and/or function. The term "gene therapy" can also refer to modifications made to a deleterious gene or regulatory element (e.g., oncogenes) that reduce or eliminate expression of the gene. Gene therapy can be performed to treat congenital conditions, conditions resulting from mutations or damage to specific genetic loci over the life of the patient, or conditions resulting from infectious organisms.

In some aspects of the invention, dysfunctional genes are replaced or disabled by the insertion of exogenous nucleic acid sequences into a region of the genome affecting gene expression. In certain embodiments, the recombinant meganuclease is targeted to a particular sequence in the region of the genome to be modified so as to alleviate the condition. The sequence can be a region within an exon, intron, promoter, or other regulatory region that is causing dysfunctional expression of the gene. As used herein, the term "dysfunctional expression" means aberrant expression of a gene product either by the cell producing too little of the gene product, too much of the gene product, or producing a gene product that has a different function such as lacking the necessary function or having more than the necessary function.

Exogenous nucleic acid sequences inserted into the modified region can be used to provide "repaired" sequences that normalize the gene. Gene repair can be accomplished by the introduction of proper gene sequences into the gene allowing for proper function to be reestablished. In these embodiments, the nucleic acid sequence to be inserted can be the entire coding sequence for a protein or, in certain embodiments, a fragment of the gene comprising only the region to be repaired. In other embodiments the nucleic acid sequence to be inserted comprises a promoter sequence or other regulatory elements such that mutations causing abnormal expression or regulation are repaired. In other embodiments, the nucleic acid sequence to be inserted contains the appropriate translation stop codon lacking in a mutated gene. The nucleic acid sequence can also have sequences for stopping transcription in a recombinant gene lacking appropriate transcriptional stop signals.

Alternatively, the nucleic acid sequences can eliminate gene function altogether by disrupting the regulatory sequence of the gene or providing a silencer to eliminate gene function. In some embodiments, the exogenous nucleic acid sequence provides a translation stop codon to prevent expression of the gene product. In other embodiments, the exogenous nucleic acid sequences provide transcription stop element to prevent expression of a full length RNA molecule. In still other embodiments, gene function is disrupted directly by the meganuclease by introducing base insertions, base deletions, and/or frameshift mutations through non-homologous end-joining.

In many instances, it is desirable to direct the proper genetic sequences to a target cell or population of cells that is the cause of the disease condition. Such targeting of therapeutics prevents healthy cells from being targeted by the therapeutics. This increases the efficacy of the treatment, while decreasing the potentially adverse effects that the treatment could have on healthy cells.

Delivery of recombinant meganuclease genes and the sequence of interest to be inserted into the genome to the cells of interest can be accomplished by a variety of mechanisms. In some embodiments, the nucleic acids are delivered to the cells by way of viruses with particular viral genes inactivated to prevent reproduction of the virus. Thus, a virus can be altered so that it is capable only of delivery and maintenance within a target cell, but does not retain the ability to replicate within the target cell or tissue. One or more DNA sequences can be introduced to the altered viral genome, so as to produce a viral genome that acts like a vector, and may or may not be inserted into a host genome and subsequently expressed. More specifically, certain embodiments include employing a retroviral vector such as, but not limited to, the MFG or pLJ vectors. An MFG vector is a simplified Moloney murine leukemia virus vector (MoMLV) in which the DNA sequences encoding the pol and env proteins have been deleted to render it replication defective. A pLJ retroviral vector is also a form of the MoMLV (see, e.g., Korman et al. (1987), *Proc. Nat'l Acad. Sci.*, 84:2150-2154). In other embodiments, a recombinant adenovirus or adeno-associated virus can be used as a delivery vector.

In other embodiments, the delivery of recombinant meganuclease protein and/or recombinant meganuclease gene sequences to a target cell is accomplished by the use of liposomes. The production of liposomes containing nucleic acid and/or protein cargo is known in the art (see, e.g., Lasic et al. (1995), *Science* 267: 1275-76). Immunoliposomes incorporate antibodies against cell-associated antigens into liposomes, and can delivery DNA sequences for the meganuclease or the meganuclease itself to specific cell types (see, e.g., Lasic et al. (1995), *Science* 267: 1275-76; Young et al. (2005), *J. Calif. Dent. Assoc.* 33(12): 967-71; Pfeiffer et al. (2006), *J. Vasc. Surg.* 43(5):1021-7). Methods for producing and using liposome formulations are well known in the art, (see, e.g., U.S. Pat. No. 6,316,024, U.S. Pat. No. 6,379,699, U.S. Pat. No. 6,387,397, U.S. Pat. No. 6,511,676 and U.S. Pat. No. 6,593,308, and references cited therein). In some embodiments, liposomes are used to deliver the sequences of interest as well as the recombinant meganuclease protein or recombinant meganuclease gene sequences.

7. Methods for Treating Pathogen Infection.

Aspects of the invention also provide methods of treating infection by a pathogen. Pathogenic organisms include viruses such as, but not limited to, herpes simplex virus 1, herpes simplex virus 2, human immunodeficiency virus 1, human immunodeficiency virus 2, variola virus, polio virus, Epstein-Barr virus, and human papilloma virus and bacterial organisms such as, but not limited to, *Bacillus anthracis, Haemophilus* species, *Pneumococcus* species, *Staphylococcus aureus, Streptococcus* species, methicillin-resistant *Staphylococcus aureus*, and *Mycoplasma tuberculosis*. Pathogenic organisms also include fungal organisms such as, but not limited to, *Candida, Blastomyces, Cryptococcus*, and *Histoplasma* species.

In some embodiments, a rationally-designed meganuclease can be targeted to a recognition sequence within the pathogen genome, e.g., to a gene or regulatory element that is essential for growth, reproduction, or toxicity of the pathogen. In certain embodiments, the recognition sequence may be in a bacterial plasmid. Meganuclease-mediated cleavage of a recognition sequence in a pathogen genome can stimulate mutation within a targeted, essential gene in the form of an insertion, deletion or frameshift, by stimulating non-homologous end-joining. Alternatively, cleavage of a bacterial plasmid can result in loss of the plasmid along with any genes encoded on it, such as toxin genes (e.g., *B. anthracis* Lethal Factor gene) or antibiotic resistance genes. As noted above, the meganuclease may be delivered to the infected patient, animal, or plant in either protein or nucleic acid form using techniques that are common in the art. In certain embodiments, the meganuclease gene may be incorporated into a bacteriophage genome for delivery to pathogenic bacteria.

Aspects of the invention also provide therapeutics for the treatment of certain forms of cancer. Because human viruses are often associated with tumor formation (e.g., Epstein-Barr Virus and nasopharyngeal carcinomas; Human Papilloma Virus and cervical cancer) inactivation of these viral pathogens may prevent cancer development or progression. Alternatively, double-stranded breaks targeted to the genomes of these tumor-associated viruses using rationally-designed meganucleases may be used to trigger apoptosis through the DNA damage response pathway. In this manner, it may be possible to selectively induce apoptosis in tumor cells harboring the viral genome.

8. Methods for Genotyping and Pathogen Identification

Aspects of the invention also provide tools for in vitro molecular biology research and development. It is common in the art to use site-specific endonucleases (e.g., restriction enzymes) for the isolation, cloning, and manipulation of nucleic acids such as plasmids, PCR products, BAC sequences, YAC sequences, viruses, and genomic sequences from eukaryotic and prokaryotic organisms (see, e.g., Ausubel et al., *Current Protocols in Molecular Biology*, Wiley 1999). Thus, in some embodiments, a rationally-designed meganuclease may be used to manipulate nucleic acid sequences in vitro. For example, rationally-designed meganucleases recognizing a pair of recognition sequences within the same DNA molecule can be used to isolate the intervening DNA segment for subsequent manipulation such as ligation into a bacterial plasmid, BAC, or YAC.

In another aspect, this invention provides tools for the identification of pathogenic genes and organisms. In one embodiment, rationally-designed meganucleases can be used to cleave recognition sites corresponding to polymorphic genetic regions correlated to disease to distinguish disease-causing alleles from healthy alleles (e.g., a rationally-designed meganuclease which recognizes the $\Delta$F-508 allele of the human CFTR gene, see example 4). In this embodiment, DNA sequences isolated from a human patient or other organism are digested with a rationally-designed meganuclease, possibly in conjunction with additional site-specific nucleases, and the resulting DNA fragment pattern is analyzed by gel electrophoresis, capillary electrophoresis, mass spectrometry, or other methods known in the art. This fragmentation pattern and, specifically, the presence or absence of cleavage by the rationally-designed meganuclease, indicates the genotype of the organism by revealing whether or not the recognition sequence is present in the genome. In another embodiment, a rationally-designed meganuclease is targeted to a polymorphic region in the genome of a pathogenic virus, fungus, or bacterium and used to identify the organism. In this embodiment, the rationally-designed meganuclease cleaves a recognition sequence that is unique to the pathogen (e.g., the spacer region between the 16S and 23S rRNA genes in a bacterium; see, e.g., van der Giessen et al. (1994), *Microbiology* 140:1103-1108) and can be used to distinguish the pathogen from other closely-related organisms following endonuclease digest of the genome and subsequent analysis of the fragmentation pattern by electrophoresis, mass spectrometry, or other methods known in the art.

9. Methods for the Production of Custom DNA-Binding Domains.

In another aspect, the invention provides rationally-designed DNA-binding proteins that lack endonuclease cleavage activity. The catalytic activity of a rationally-designed meganuclease can be eliminated by mutating amino acids involved in catalysis (e.g., the mutation of Q47 to E in I-CreI, see Chevalier et al. (2001), *Biochemistry.* 43:14015-14026); the mutation of D44 or D145 to N in I-SceI; the mutation of E66 to Q in I-CeuI; the mutation of D22 to N in I-MsoI). The inactivated meganuclease can then be fused to an effector domain from another protein including, but not limited to, a transcription activator (e.g., the GAL4 transactivation domain or the VP16 transactivation domain), a transcription repressor (e.g., the KRAB domain from the Kruppel protein), a DNA methylase domain (e.g., M.CviPI or M.SssI), or a histone acetyltransferase domain (e.g., HDAC1 or HDAC2). Chimeric proteins consisting of an engineered DNA-binding domain, most notably an engineered zinc finger domain, and an effector domain are known in the art (see, e.g., Papworth et al. (2006), *Gene* 366:27-38).

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below. Examples 1-4 below refer specifically to rationally-designed meganucleases based on I-CreI, but rationally-designed meganucleases based on I-SceI, I-MsoI, I-CeuI, and other LAGL-IDADG meganucleases can be similarly produced and used, as described herein.

Example 1

Rational Design of Meganucleases Recognizing the HIV-1 TAT Gene

1. Meganuclease Design

A pair of meganucleases were designed to recognize and cleave the DNA site 5'-GAAGAGCTCATCAGAA-CAGTCA-3' (SEQ ID NO: 15) found in the HIV-1 TAT Gene. In accordance with Table 1, two meganucleases, TAT1 and TAT2, were designed to bind the half-sites 5'-GAA-GAGCTC-3' (SEQ ID NO: 16) and 5'-TGACTGTTC-3' (SEQ ID NO: 17), respectively, using the following base contacts (non-WT contacts are in bold):

| Position | −9 | −8 | −7 | −6 | −5 | −4 | −3 | −2 | −1 |
|---|---|---|---|---|---|---|---|---|---|
| TAT1: | | | | | | | | | |
| Base | G | A | A | G | A | G | C | T | C |
| Contact Residues | S32 | Y33 | N30/ Q38 | R40 | K28 | S26/ R77 | K24/ Y68 | Q44 | R70 |
| TAT2: | | | | | | | | | |
| Base | T | G | A | C | T | G | T | T | C |
| Contact Residues | C32 | R33 | N30/ Q38 | R28/ E40 | M66 | S26/ R77 | Y68 | Q44 | R70 |

The two enzymes were cloned, expressed in *E. coli*, and assayed for enzyme activity against the corresponding DNA recognition sequence as described below. In both cases, the rationally-designed meganucleases were found to be inactive. A second generation of each was then produced in which E80 was mutated to Q to improve contacts with the DNA backbone. The second generation TAT2 enzyme was found to be active against its intended recognition sequence while the second generation TAT1 enzyme remained inactive. Visual inspection of the wild-type I-CreI co-crystal structure suggested that TAT1 was inactive due to a steric clash between R40 and K28. To alleviate this clash, TAT1 variants were produced in which K28 was mutated to an amino acid with a smaller side chain (A, S, T, or C) while maintaining the Q80 mutation. When these enzymes were produced in *E. coli* and assayed, the TAT1 variants with S28 and T28 were both found to be active against the intended recognition sequence while maintaining the desired base preference at position −7.

2. Construction of Recombinant Meganucleases

Mutations for the redesigned I-CreI enzymes were introduced using mutagenic primers in an overlapping PCR strategy. Recombinant DNA fragments of I-CreI generated in a primary PCR were joined in a secondary PCR to produce full-length recombinant nucleic acids. All recombinant I-CreI constructs were cloned into pET21*a* vectors with a six histidine tag fused at the 3' end of the gene for purification (Novagen Corp., San Diego, Calif.). All nucleic acid sequences were confirmed using Sanger Dideoxynucleotide sequencing (see Sanger et al. (1977), *Proc. Natl. Acad. Sci. USA*. 74(12): 5463-7).

Wild-type I-CreI and all engineered meganucleases were expressed and purified using the following method. The constructs cloned into a pET21*a* vector were transformed into chemically competent BL21 (DE3) pLysS, and plated on standard 2×YT plates containing 200 µg/ml carbanicillin. Following overnight growth, transformed bacterial colonies were scraped from the plates and used to inoculate 50 ml of 2×YT broth. Cells were grown at 37° C. with shaking until they reached an optical density of 0.9 at a wavelength of 600 nm. The growth temperature was then reduced from 37° C. to 22° C. Protein expression was induced by the addition of 1 mM IPTG, and the cells were incubated with agitation for two and a half hours. Cells were then pelleted by centrifugation for 10 min. at 6000×g. Pellets were resuspended in 1 ml binding buffer (20 mM Tris-HCL, pH 8.0, 500 mM NaCl, 10 mM imidazole) by vortexing. The cells were then disrupted with 12 pulses of sonication at 50% power and the cell debris was pelleted by centrifugation for 15 min. at 14,000×g. Cell supernatants were diluted in 4 ml binding buffer and loaded onto a 200 µl nickel-charged metal-chelating Sepharose column (Pharmacia).

The column was subsequently washed with 4 ml wash buffer (20 mM Tris-HCl pH 8.0, 500 mM NaCl, 60 mM imidazole) and with 0.2 ml elution buffer (20 mM Tris-HCl, pH 8.0, 500 mM NaCl, 400 mM imidazole). Meganuclease enzymes were eluted with an additional 0.6 ml of elution buffer and concentrated to 50-130 µl using Vivospin disposable concentrators (ISC, Inc., Kaysville, Utah). The enzymes were exchanged into SA buffer (25 mM Tris-HCL, pH 8.0, 100 mM NaCl, 5 mM MgCl$_2$, 5 mM EDTA) for assays and storage using Zeba spin desalting columns (Pierce Biotechnology, Inc., Rockford, Ill.). The enzyme concentration was determined by absorbance at 280 nm using an extinction coefficient of 23,590 M$^{-1}$ cm$^{-1}$. Purity and molecular weight of the enzymes was then confirmed by MALDI-TOF mass spectrometry.

Heterodimeric enzymes were produced either by purifying the two proteins independently, and mixing them in vitro or by constructing an artificial operon for tandem expression of the two proteins in *E. coli*. In the former case, the purified meganucleases were mixed 1:1 in solution and pre-incubated at 42° C. for 20 minutes prior to the addition of DNA substrate. In the latter case, the two genes were cloned sequentially into the pET-21a expression vector using NdeI/EcoRI and EcoRI/HindIII. The first gene in the operon ends with two stop codons to prevent read-through errors during transcription. A 12-base pair nucleic acid spacer and a Shine-Dalgarno sequence from the pET21 vector separated the first and second genes in the artificial operon.

3. Cleavage Assays

All enzymes purified as described above were assayed for activity by incubation with linear, double-stranded DNA substrates containing the meganuclease recognition sequence. Synthetic oligonucleotides corresponding to both sense and antisense strands of the recognition sequence were annealed and were cloned into the SmaI site of the pUC19 plasmid by blunt-end ligation. The sequences of the cloned binding sites were confirmed by Sanger dideoxynucleotide sequencing. All plasmid substrates were linearized with XmnI, ScaI or BpmI concurrently with the meganuclease digest. The enzyme digests contained 5 µl 0.05 µM DNA substrate, 2.5 µl 5 µM recombinant I-CreI meganuclease, 9.5 µl SA buffer, and 0.5 µl XmnI, ScaI, or BpmI. Digests were incubated at either 37° C., or 42° C. for certain meganuclease enzymes, for four hours. Digests were stopped by adding 0.3 mg/ml Proteinase K and 0.5% SDS, and incubated for one hour at 37° C. Digests were analyzed on 1.5% agarose and visualized by ethidium bromide staining.

To evaluate meganuclease half-site preference, rationally-designed meganucleases were incubated with a set of DNA substrates corresponding to a perfect palindrome of the intended half-site as well as each of the 27 possible single-base-pair substitutions in the half-site. In this manner, it was possible to determine how tolerant each enzyme is to deviations from its intended half-site.

4. Recognition Sequence-Specificity

Figure 3:
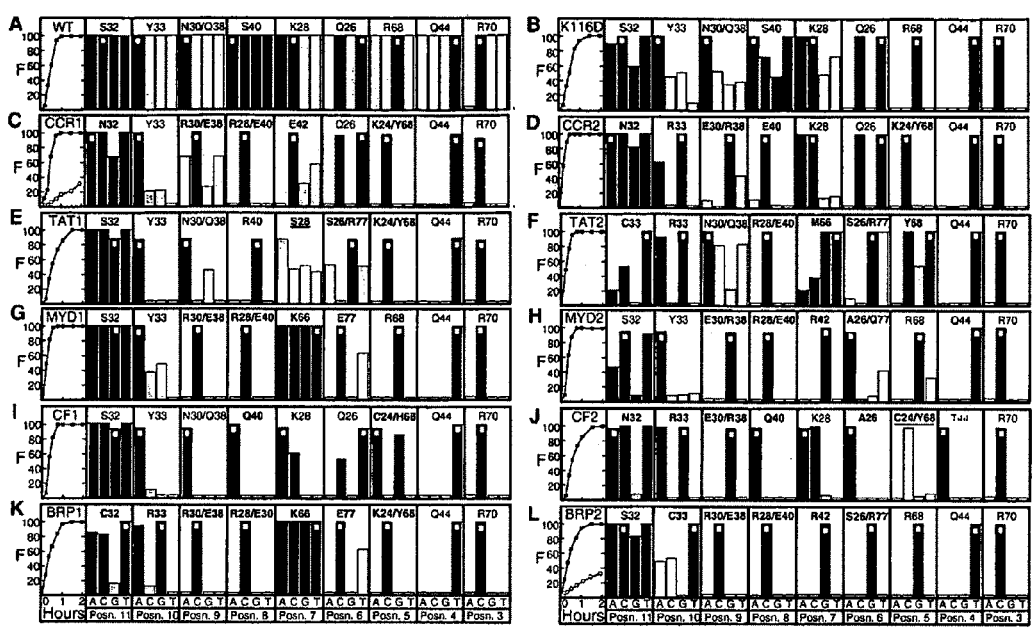
FIG. 3 illustrates cleavage patterns of wild-type and rationally-designed I-CreI homodimers. (A) wild type I-CreI. (B) I-CreI K116D. (C-L) rationally-designed meganucleases of the invention. Enzymes were incubated with a set of plasmids harboring palindromes of the intended cleavage half-site the 27 corresponding single-base pair variations. Bar graphs show fractional cleavage (F) in 4 hours at 37° C. Black bars: expected cleavage patterns based on Table 1. Gray bars: DNA sites that deviate from expected cleavage patterns. White circles indicate bases in the intended recognition site. Also shown are cleavage time-courses over two hours. The open circle time-course plots in C and L correspond to cleavage by the CCR1 and BRP2 enzymes lacking the E80Q mutation. The cleavage sites correspond to the 5' (left column) and 3' (right column) half-sites for the heterodimeric enzymes described in FIG. 2(A).

Purified recombinant TAT1 and TAT2 meganucleases recognized DNA sequences that were distinct from the wild-type meganuclease recognition sequence (FIG. 2(B)). The wild-type I-CreI meganuclease cleaves the WT recognition sequence, but cuts neither the intended sequence for TAT1 nor the intended sequence for TAT2. TAT1 and TAT2, likewise, cut their intended recognition sequences but not the wild-type sequence. The meganucleases were then evaluated for half-site preference and overall specificity (FIG. 3). Wild-type I-CreI was found to be highly tolerant of single-base-pair substitutions in its natural half-site. In contrast, TAT1 and TAT2 were found to be highly-specific and completely intolerant of base substitutions −1, −2, −3, −6, and −8 in the case of TAT1, and positions −1, −2, and −6 in the case of TAT2.

Example 2

Rational Design of Meganucleases with Altered DNA-Binding Affinity

1. Meganucleases with Increased Affinity and Increased Activity

The meganucleases CCR1 and BRP2 were designed to cleave the half-sites 5'-AACCCTCTC-3' (SEQ ID NO: 18) and 5'-CTCCGGGTC-3' (SEQ ID NO: 19), respectively. These enzymes were produced in accordance with Table 1 as in Example 1:

| Position | −9 | −8 | −7 | −6 | −5 | −4 | −3 | −2 | −1 |
|---|---|---|---|---|---|---|---|---|---|
| CCR1: | | | | | | | | | |
| Base | A | A | C | C | C | T | C | T | C |
| Contact Residues | N32 | Y33 | R30/ E38 | R28/ E40 | E42 | Q26 | K24/ Y68 | Q44 | R70 |
| BRP2: | | | | | | | | | |
| Base | C | T | C | C | G | G | G | T | C |
| Contact Residues | S32 | C33 | R30/ E38 | R28/ E40 | R42 | S26/ R77 | R68 | q44 | R70 |

Both enzymes were expressed in *E. coli*, purified, and assayed as in Example 1. Both first generation enzymes were found to cleave their intended recognition sequences with rates that were considerably below that of wild-type I-CreI with its natural recognition sequence. To alleviate this loss in activity, the DNA-binding affinity of CCR1 and BRP2 was increased by mutating E80 to Q in both enzymes. These second-generation versions of CCR1 and BRP2 were found to cleave their intended recognition sequences with substantially increased catalytic rates.

2. Meganucleases with Decreased DNA-binding Affinity and Decreased Activity but Increased Specificity.

Wild-type I-CreI was found to be highly-tolerant of substitutions to its half-site (FIG. 3(A)). In an effort to make the enzyme more specific, the lysine at position 116 of the enzyme, which normally makes a salt-bridge with a phosphate in the DNA backbone, was mutated to aspartic acid to reduce DNA-binding affinity. This rationally-designed enzyme was found to cleave the wild-type recognition sequence with substantially reduced activity but the recombinant enzyme was considerably more specific than wild-type. The half-site preference of the K116D variant was evaluated as in Example 1 and the enzyme was found to be entirely intolerant of deviation from its natural half-site at positions −1, −2, and −3, and displayed at least partial base preference at the remaining 6 positions in the half-site (FIG. 3(B)).

Example 3

Rationally-Designed Meganuclease Heterodimers

1. Cleavage of Non-Palindromic DNA Sites by Meganuclease Heterodimers Formed in Solution Two meganucleases, LAM1 and LAM2, were designed to cleave the half-sites 5'-TGCGGTGTC-3' (SEQ ID NO: 20) and 5'-CAGGCTGTC-3' (SEQ ID NO: 21), respectively. The heterodimer of these two enzymes was expected to recognize the DNA sequence 5'-TGCGGTGTCCGGCGACAGCCTG-3' (SEQ ID NO: 22) found in the bacteriophage λp05 gene.

| Position | −9 | −8 | −7 | −6 | −5 | −4 | −3 | −2 | −1 |
|---|---|---|---|---|---|---|---|---|---|
| LAM1: | | | | | | | | | |
| Base | T | G | C | G | G | T | G | T | C |
| Contact Residues | C32 | R33 | R30/ E38 | D28/ R40 | R42 | Q26 | R68 | Q44 | R70 |
| LAM2: | | | | | | | | | |
| Base | C | A | G | G | C | T | G | T | C |
| Contact Residues | S32 | Y33 | E30/ R38 | R40 | K28/ E42 | Q26 | R68 | Q44 | R70 |

LAM1 and LAM 2 were cloned, expressed in *E. coli*, and purified individually as described in Example 1. The two enzymes were then mixed 1:1 and incubated at 42° C. for 20 minutes to allow them to exchange subunits and re-equilibrate. The resulting enzyme solution, expected to be a mixture of LAM1 homodimer, LAM2 homodimer, and LAM1/LAM2 heterodimer, was incubated with three different recognition sequences corresponding to the perfect palindrome of the LAM1 half-site, the perfect palindrome of the LAM2 half-site, and the non-palindromic hybrid site found in the bacteriophage λ genome. The purified LAM1 enzyme alone cuts the LAM1 palindromic site, but neither the LAM2 palindromic site, nor the LAM1/LAM2 hybrid site. Likewise, the purified LAM2 enzyme alone cuts the LAM2 palindromic site but neither the LAM1 palindromic site nor the LAM1/LAM2 hybrid site. The 1:1 mixture of LAM1 and LAM2, however, cleaves all three DNA sites. Cleavage of the LAM1/LAM2 hybrid site indicates that two distinct redesigned meganucleases can be mixed in solution to form a heterodimeric enzyme capable of cleaving a non-palindromic DNA site.

2. Cleavage of Non-Palindromic DNA Sites by Meganuclease Heterodimers Formed by Co-Expression Genes encoding the LAM1 and LAM2 enzymes described above were arranged into an operon for simultaneous expression in *E. coli* as described in Example 1. The co-expressed enzymes were purified as in Example 1 and the enzyme mixture incubated with the three potential recognition sequences described above. The co-expressed enzyme mixture was found to cleave all three sites, including the LAM 1/LAM2 hybrid site, indicating that two distinct rationally-designed meganucleases can be co-expressed to form a heterodimeric enzyme capable of cleaving a non-palindromic DNA site.

3. Preferential Cleavage of Non-Palindromic DNA Sites by Meganuclease Heterodimers with Modified Protein-Protein Interfaces.

For applications requiring the cleavage of non-palindromic DNA sites, it is desirable to promote the formation of enzyme heterodimers while minimizing the formation of homodimers that recognize and cleave different (palindromic) DNA sites. To this end, variants of the LAM1 enzyme were produced in which lysines at positions 7, 57, and 96 were changed to glutamic acids. This enzyme was then co-expressed and purified as in above with a variant of LAM2 in which glutamic acids at positions 8 and 61 were changed to lysine. In this case, formation of the LAM1 homodimer was expected to be reduced due to electrostatic repulsion between E7, E57, and E96 in one monomer and E8 and E61 in the other monomer. Likewise, formation of the LAM2 homodimer was expected to be reduced due to electrostatic repulsion between K7, K57, and K96 on one monomer and K8 and K61 on the other monomer. Conversely, the LAM1/LAM2 heterodimer was expected to be favored due to electrostatic attraction between E7, E57, and E96 in LAM1 and K8 and K61 in LAM2. When the two meganucleases with modified interfaces were co-expressed and assayed as described above, the LAM1/LAM2 hybrid site was found to be cleaved preferentially over the two palindromic sites, indicating that substitutions in the meganuclease protein-protein interface can drive the preferential formation of heterodimers.

Example 4

Additional Meganuclease Heterodimers Which Cleave Physiologic DNA Sequences

1. Meganuclease Heterodimers which Cleave DNA Sequences Relevant to Gene Therapy A rationally-designed meganuclease heterodimer (ACH1/ACH2) can be produced that cleaves the sequence 5'-CTGG-GAGTCTCAGGACAGCCTG-3' (SEQ ID NO: 23) in the human FGFR3 gene, mutations in which cause achondroplasia. For example, a meganuclease was designed based on the I-CreI meganuclease, as described above, with the following contact residues and recognition sequence half-sites:

| Position | −9 | −8 | −7 | −6 | −5 | −4 | −3 | −2 | −1 |
|---|---|---|---|---|---|---|---|---|---|
| ACH1: | | | | | | | | | |
| Base Contact Residues | C D32 | T C33 | G E30/ R38 | G R40/ D28 | G R42 | A A26/ Q77 | G R68 | T Q44 | C R70 |
| ACH2: | | | | | | | | | |
| Base Contact Residues | C D32 | A Y33 | G E30/ R38 | G R40 | C K28/ E42 | T Q26 | G R68 | T Q44 | C R70 |

A rationally-designed meganuclease heterodimer (HGH1/HGH2) can be produced that cleaves the sequence 5'-CCAG-GTGTCTCTGGACTCCTCC-3' (SEQ ID NO: 24) in the promoter of the Human Growth Hormone gene. For example, a meganuclease was designed based on the I-CreI meganuclease, as described above, with the following contact residues and recognition sequence half-sites:

| Position | −9 | −8 | −7 | −6 | −5 | −4 | −3 | −2 | −1 |
|---|---|---|---|---|---|---|---|---|---|
| HGH1: | | | | | | | | | |
| Base Contact Residues | C D32 | C C33 | A N30/ Q38 | G R40/ D28 | G R42 | T Q26 | G R68 | T Q44 | C R70 |
| HGH2: | | | | | | | | | |
| Base Contact Residues | G K32 | G R33 | A N30/ Q38 | G R40/ D28 | G R42 | A A26 | G R68 | T Q44 | C R70 |

A rationally-designed meganuclease heterodimer (CF1/CF2) can be produced that cleaves the sequence 5'-GAAAATATCATTGGTGTTTCCT-3' (SEQ ID NO: 25) in the ΔF508 allele of the human CFTR gene. For example, a meganuclease was designed based on the I-CreI meganuclease, as described above, with the following contact residues and recognition sequence half-sites:

| Position | −9 | −8 | −7 | −6 | −5 | −4 | −3 | −2 | −1 |
|---|---|---|---|---|---|---|---|---|---|
| CF1: | | | | | | | | | |
| Base Contact Residues | G S32 | A Y33 | A N30/ Q38 | A Q40 | A K28 | T Q26 | A H68/ C24 | T Q44 | C R70 |
| CF2: | | | | | | | | | |
| Base Contact Residues | A N32 | G R33 | G E30/ R38 | A Q40 | A K28 | A A26 | C Y68/ C24 | A T44 | C R70 |

A rationally-designed meganuclease heterodimer (CCR1/CCR2) can be produced that cleaves the sequence 5'-AAC-CCTCTCCAGTGAGATGCCT-3' (SEQ ID NO: 26) in the human CCR5 gene (an HIV co-receptor). For example, a meganuclease was designed based on the I-CreI meganuclease, as described above, with the following contact residues and recognition sequence half-sites:

| Position | −9 | −8 | −7 | −6 | −5 | −4 | −3 | −2 | −1 |
|---|---|---|---|---|---|---|---|---|---|
| CCR1: | | | | | | | | | |
| Base Contact Residues | A N32 | A Y33 | C R30/ E38 | C E40/ R28 | C E42 | T Q26 | C Y68/ K24 | T Q44 | C R70 |
| CCR2: | | | | | | | | | |
| Base Contact Residues | A N32 | G R33 | G E30/ R38 | C E40 | A K28 | T Q26 | C Y68/ K24 | T Q44 | C R70 |

A rationally-designed meganuclease heterodimer (MYD1/MYD2) can be produced that cleaves the sequence 5'-GAC-CTCGTCCTCCGACTCGCTG-3' (SEQ ID NO: 27) in the 3' untranslated region of the human DM kinase gene. For example, a meganuclease was designed based on the I-CreI meganuclease, as described above, with the following contact residues and recognition sequence half-sites:

| Position | −9 | −8 | −7 | −6 | −5 | −4 | −3 | −2 | −1 |
|---|---|---|---|---|---|---|---|---|---|
| MYD1: | | | | | | | | | |
| Base Contact Residues | G S32 | A Y33 | C R30/ E38 | C E40/ R28 | T K66 | C Q26/ E77 | G R68 | T Q44 | C R70 |
| MYD1: | | | | | | | | | |
| Base Contact Residues | C S32 | A Y33 | G E30/ R38 | C E40/ R28 | G R42 | A A26/ Q77 | G R68 | T Q44 | C R70 |

2. Meganuclease Heterodimers which Cleave DNA Sequences in Pathogen Genomes

A rationally-designed meganuclease heterodimer (HSV1/HSV2) can be produced that cleaves the sequence 5'-CTC-GATGTCGGACGACACGGCA-3' (SEQ ID NO: 28) in the UL36 gene of Herpes Simplex Virus-1 and Herpes Simplex Virus-2. For example, a meganuclease was designed based on the I-CreI meganuclease, as described above, with the following contact residues and recognition sequence half-sites:

| Position | −9 | −8 | −7 | −6 | −5 | −4 | −3 | −2 | −1 |
|---|---|---|---|---|---|---|---|---|---|
| HSV1: | | | | | | | | | |
| Base Contact Residues | C S32 | T C33 | C R30/ E38 | G R40/ K28 | A Q42/ | T Q26 | G R68 | T Q44 | C R70 |
| HSV2: | | | | | | | | | |
| Base Contact Residues | T C32 | G R33 | C R30/ E38 | C E40/ R28 | G R42 | T Q26 | G R68 | T Q44 | C R70 |

A rationally-designed meganuclease heterodimer (ANT1/ANT2) can be produced that cleaves the sequence 5'-ACAAGTGTCTATGGACAGTTTA-3' (SEQ ID NO: 29) in the *Bacillus anthracis* genome. For example, a meganuclease was designed based on the I-CreI meganuclease, as described above, with the following contact residues and recognition sequence half-sites:

| Position | −9 | −8 | −7 | −6 | −5 | −4 | −3 | −2 | −1 |
|---|---|---|---|---|---|---|---|---|---|
| ANT1: | | | | | | | | | |
| Base Contact Residues | A N32 | C C33 | A N30/ Q38 | A Q40/ A28 | G R42 | T Q26 | G R68 | T Q44 | C R70 |
| ANT2: | | | | | | | | | |
| Base Contact Residues | T C32 | A Y33 | A N30/ Q38 | A Q40 | C E42 | T Q26 | G R68 | T Q44 | C R70 |

A rationally-designed meganuclease heterodimer (POX1/POX2) can be produced that cleaves the sequence 5'-AAAACTGTCAAATGACATCGCA-3' (SEQ ID NO: 30) in the Variola (smallpox) virus gp009 gene. For example, a meganuclease was designed based on the I-CreI meganuclease, as described above, with the following contact residues and recognition sequence half-sites:

| Position | −9 | −8 | −7 | −6 | −5 | −4 | −3 | −2 | −1 |
|---|---|---|---|---|---|---|---|---|---|
| POX1: | | | | | | | | | |
| Base Contact Residues | A N32 | A C33 | A N30/ Q38 | A Q40 | C K28 | T Q26 | G R68 | T Q44 | C R70 |
| POX2: | | | | | | | | | |
| Base Contact Residues | T C32 | G R33 | C R30/ E38 | G R40 | A C28/ Q42 | T Q26 | G R68 | T Q44 | C R70 |

A rationally-designed meganuclease homodimer (EBB1/EBB1) can be produced that cleaves the pseudo-palindromic sequence 5'-CGGGGTCTCGTGCGAGGCCTCC-3' (SEQ ID NO: 31) in the Epstein-Barr Virus BALF2 gene. For example, a meganuclease was designed based on the I-CreI meganuclease, as described above, with the following contact residues and recognition sequence half-sites:

| Position | −9 | −8 | −7 | −6 | −5 | −4 | −3 | −2 | −1 |
|---|---|---|---|---|---|---|---|---|---|
| EBB1: | | | | | | | | | |
| Base Contact Residues | C S32 | G R33 | G D30/ Q38 | G R40/ D28 | G R42 | T Q26 | C Y68/ K24 | T Q44 | C R70 |
| EBB1: | | | | | | | | | |
| Base Contact Residues | G S32 | G R33 | A D30/ Q38 | G R40/ D28 | G R42 | C Q26 | C Y68/ K24 | T Q44 | C R70 |

3. Meganuclease Heterodimers which Cleave DNA Sequences in Plant Genomes

A rationally-designed meganuclease heterodimer (GLA1/GLA2) can be produced that cleaves the sequence 5'-CACTAACTCGTATGAGTCGGTG-3' (SEQ ID NO: 32) in the *Arabidopsis thalianna* GL2 gene. For example, a meganuclease was designed based on the I-CreI meganuclease, as described above, with the following contact residues and recognition sequence half-sites:

| Position | −9 | −8 | −7 | −6 | −5 | −4 | −3 | −2 | −1 |
|---|---|---|---|---|---|---|---|---|---|
| GLA1: | | | | | | | | | |
| Base Contact Residues | C S32 | A Y33 | C R30/ E38 | T S40/ C79 | A K28 | A A26/ Q77 | C Y68/ K24 | T Q44 | C R70 |
| GLA2: | | | | | | | | | |
| Base Contact Residues | C S32 | A Y33 | C R30/ E38 | C E40/ R28 | G R42 | A A26/ Q77 | C Y68/ K24 | T Q44 | C R70 |

A rationally-designed meganuclease heterodimer (BRP1/BRP2) can be produced that cleaves the sequence 5'-TGC-CTCCTCTAGAGACCCGGAG-3' (SEQ ID NO: 33) in the *Arabidopsis thalianna* BPI gene. For example, a meganuclease was designed based on the I-CreI meganuclease, as described above, with the following contact residues and recognition sequence half-sites:

| Position | −9 | −8 | −7 | −6 | −5 | −4 | −3 | −2 | −1 |
|---|---|---|---|---|---|---|---|---|---|
| BRP1: | | | | | | | | | |
| Base | T | G | C | C | T | C | C | T | C |
| Contact Residues | C32 | R33 | R30/ E38 | R28/ E40 | K66 | Q26/ E77 | Y68/ K24 | Q44 | R70 |
| BRP2: | | | | | | | | | |
| Base | C | T | C | C | G | G | G | T | C |
| Contact Residues | S32 | C33 | R30/ E38 | E40/ R28 | R42 | S26 R77 | R68 | Q44 | R70 |

A rationally-designed meganuclease heterodimer (MGC1/MGC2) can be produced that cleaves the sequence 5'-TAAAATCTCTAAGGTCTGTGCA-3' (SEQ ID NO: 34) in the *Nicotiana tabacum* Magnesium Chelatase gene. For example, a meganuclease was designed based on the I-CreI meganuclease, as described above, with the following contact residues and recognition sequence half-sites:

| Position | −9 | −8 | −7 | −6 | −5 | −4 | −3 | −2 | −1 |
|---|---|---|---|---|---|---|---|---|---|
| MGC1: | | | | | | | | | |
| Base | T | A | A | A | A | T | C | T | C |
| Contact Residues | C32 | Y33 | N30/ Q38 | Q40/ | K28 | Q26 | Y68/ K24 | Q44 | R70 |
| MGC2: | | | | | | | | | |
| Base | T | G | C | A | C | A | G | A | C |
| Contact Residues | S32 | R33 | R30/ E38 | Q40 | K28 | A26 Q77 | R68 | T44 | R70 |

A rationally-designed meganuclease heterodimer (CYP/HGH2) can be produced that cleaves the sequence 5'-CAA-GAATTCAAGCGAGCATTAA-3' (SEQ ID NO: 35) in the *Nicotiana tabacum* CYP82E4 gene. For example, a meganuclease was designed based on the I-CreI meganuclease, as described above, with the following contact residues and recognition sequence half-sites:

| Position | −9 | −8 | −7 | −6 | −5 | −4 | −3 | −2 | −1 |
|---|---|---|---|---|---|---|---|---|---|
| CYP: | | | | | | | | | |
| Base | C | A | A | G | A | A | T | T | C |
| Contact Residues | D32 | Y33 | N30/ Q38 | R40/ | K28 | Q77/ A26 | Y68 | Q44 | R70 |
| HGH2: | | | | | | | | | |
| Base | T | T | A | A | T | G | C | T | C |
| Contact Residues | S32 | C33 | N30/ Q38 | Q40 | K66 | R77/ S26 | Y68 K24 | Q44 | R70 |

4. Meganuclease Heterodimers which Cleave DNA Sequences in Yeast Genomes

A rationally-designed meganuclease heterodimer (URA1/URA2) can be produced that cleaves the sequence 5'-TTA-GATGACAAGGGAGACGCAT-3' (SEQ ID NO: 36) in the *Saccharomyces cerevisiae* URA3 gene. For example, a meganuclease was designed based on the I-CreI meganuclease, as described above, with the following contact residues and recognition sequence half-sites:

| Position | −9 | −8 | −7 | −6 | −5 | −4 | −3 | −2 | −1 |
|---|---|---|---|---|---|---|---|---|---|
| URA1: | | | | | | | | | |
| Base | T | T | A | G | A | T | G | A | C |
| Contact Residues | S32 | C33 | N30/ Q38 | R40 | K28 | Q26 | R68 | T44 | R70 |
| URA2: | | | | | | | | | |
| Base | A | T | G | C | G | T | C | T | C |
| Contact Residues | N32 | C33 | E30/ R38 | E40/ R28 | R42 | Q26 | Y68/ K24 | Q44 | R70 |

5. Recognition Sequence Specificity

The rationally-designed meganucleases outlined above in this Example were cloned, expressed in *E. coli*, and purified as in Example 1. Each purified meganuclease was then mixed 1:1 with its corresponding heterodimerization partner (e.g., ACH1 with ACH2, HGH1 with HGH2, etc.) and incubated with a linearized DNA substrate containing the intended non-palindromic DNA recognition sequence for each meganuclease heterodimer. As shown in FIG. 3, each rationally-designed meganuclease heterodimer cleaves its intended DNA site.

The invention claimed is:

1. A method of cleaving a target recognition site in double-stranded DNA in a non-human cell or an isolated human cell, wherein said target recognition site has a sequence that differs by at least one nucleotide modification from the wild-type I-CreI meganuclease recognition sequence of SEQ ID NO: 4:

```
Position    -9-8-7-6-5-4-3-2-1
     5'-C A A A C T G T C G T G A G A C A G T T T G-3'  (SEQ ID NO: 4)
``` wherein said target recognition site has a sequence that comprises a substitution at a position corresponding to position −3 of the I-CreI recognition site of SEQ ID NO: 4, wherein the nucleotide corresponding to position −3 of the I-CreI meganuclease recognition sequence of SEQ ID NO: 4 has been altered to an A or a C, the method comprising:

(a) introducing into a cell (i) a recombinant meganuclease, or (ii) a nucleic acid that encodes a recombinant meganuclease and causes expression of the recombinant meganuclease in said cell, wherein the recombinant meganuclease comprises a polypeptide having at least 85% sequence identity to residues 2-153 of the I-CreI meganuclease of SEQ ID NO: 1, and which differs from residues 2-153 of the I-CreI meganuclease of SEQ ID NO: 1 by a specificity-altering amino acid modification at a position corresponding to position 24 of SEQ ID NO: 1; and wherein (i) if the nucleotide corresponding to position −3 of the I-CreI meganuclease recognition sequence of SEQ ID NO: 4 has been altered to an A, the specificity-altering amino acid modification corresponds to a substitution in SEQ ID NO: 1 of I24C; and (ii) if the nucleotide corresponding to position −3 of the I-CreI meganuclease recognition sequence of SEQ ID NO: 4 has been altered to a C, the specificity-altering amino acid modification corresponds to a substitution in SEQ ID NO: 1 selected from the group consisting of I24K and I24R; and (b) contacting the recombinant meganuclease with the double-stranded DNA, whereby the meganuclease cleaves the target recognition site.

2. A method of cleaving a target recognition site in double-stranded DNA in a non-human cell or an isolated human cell, wherein said target recognition site has a sequence that differs by at least one nucleotide modification in the wild-type I-CreI meganuclease recognition sequence of SEQ ID NO: 4:

```
Position     -9-8-7-6-5-4-3-2-1
       5'-C A A C T G T C G T G A G A C A G T T T G-3'  (SEQ ID NO: 4)
``` wherein said target recognition site has a sequence that comprises a substitution at a position corresponding to position −3 of the I-CreI recognition site of SEQ ID NO: 4, the method comprising:
  (a) introducing into a cell (i) a recombinant meganuclease, or (ii) a nucleic acid that encodes a recombinant meganuclease and causes expression of the recombinant meganuclease in said cell, wherein:
    the recombinant meganuclease comprises a polypeptide having at least 85% sequence identity to residues 2-153 of the I-CreI meganuclease of SEQ ID NO: 1, and which differs from residues 2-153 of the I-CreI meganuclease of SEQ ID NO: 1 by at least a first specificity-altering amino acid modification at a position corresponding to a position of SEQ ID NO: 1 selected from the group consisting of positions 24, 26, 28, 30, 32, 33, 38, 40, 42, 44, 46, 66, 68, 70, 75, 77, 79 and 139;
  wherein:
    (i) if the nucleotide corresponding to position −3 of the I-CreI meganuclease recognition sequence of SEQ ID NO: 4 has been altered to an A, the first specificity-altering amino acid modification corresponds to a substitution in SEQ ID NO: 1 selected from the group consisting of R68Q and I24C;
    (ii) if the nucleotide corresponding to position −3 of the I-CreI meganuclease recognition sequence of SEQ ID NO: 4 has been altered to a C, the first specificity-altering amino acid modification corresponds to a substitution in SEQ ID NO: 1 selected from the group consisting of R68F, R68Y, I24K and I24R;
    (iii) if the nucleotide corresponding to position −3 of the I-CreI meganuclease recognition sequence of SEQ ID NO: 4 has been altered to a T, the first specificity-altering amino acid modification corresponds to a substitution in SEQ ID NO: 1 selected from the group consisting of R68M, R68C, R68L, R68F, R68Y, and R68K; and
  wherein:
    the recombinant meganuclease comprises at least a second specificity-altering amino acid modification corresponding to a substitution in SEQ ID NO: 1 selected from the group consisting of:
      I24C, I24K, I24R, Q26A, Q26E, Q26K, Q26S, K28A, K28C, K28H, K28Q, K28R, K28S, N30E, N30K, N30Q, N30R, S32A, S32C, S32D, S32E, S32H, S32I, S32K, S32L, S32N, S32Q, S32R, S32T, S32V, Y33C, Y33D, Y33E, Y33F, Y33H, Y33I, Y33L, Y33R, Y33V, Q38C, Q38E, Q38H, Q38I, Q38K, Q38L, Q38N, Q38R, S40A, S40C, S40E, S40I, S40Q, S40R, S40V, A42E, A42Q, A42R, Q44A, Q44C, Q44D, Q44E, Q44I, Q44K, Q44L, Q44N, Q44R, Q44T, Q44V, T46A, T46C, T46D, T46E, T46G, T46H, T46K, T46Q, T46R, Y66K, Y66M, R68C, R68E, R68F, R68H, R68K, R68L, R68M, R68Q, R68Y, R70A, R70C, R70D, R70E, R70O, R70H, R70K, R70L, R70Q, R70S, D75C, D75E, D75H, D75L, D75Q, D75R, D75Y, I77E, I77Q, I77R, I77S, S79A, S79C, S79I, S79V, K139H and K139Y; and
  (b) contacting the recombinant meganuclease with the double-stranded DNA, whereby the meganuclease cleaves the target recognition site.

3. The method of claim 2 wherein the nucleotide corresponding to position −3 of the I-CreI meganuclease recognition site of SEQ ID NO: 4 has been altered to an A and the first specificity-altering amino acid modification corresponds to a substitution of R68Q in SEQ ID NO: 1.

4. The method of claim 2 wherein the nucleotide corresponding to position −3 of the I-CreI meganuclease recognition site of SEQ ID NO: 4 has been altered to an A and the first specificity-altering amino acid modification corresponds to a substitution of I24C in SEQ ID NO: 1.

5. The method of claim 2 wherein the nucleotide corresponding to position −3 of the I-CreI meganuclease recognition site of SEQ ID NO: 4 has been altered to a C and the first specificity-altering amino acid modification corresponds to a substitution of R68F in SEQ ID NO: 1.

6. The method of claim 2 wherein the nucleotide corresponding to position −3 of the I-CreI meganuclease recognition site of SEQ ID NO: 4 has been altered to a C and the first specificity-altering amino acid modification corresponds to a substitution of R68Y in SEQ ID NO: 1.

7. The method of claim 2 wherein the nucleotide corresponding to position −3 of the I-CreI meganuclease recognition site of SEQ ID NO: 4 has been altered to a C and the first specificity-altering amino acid modification corresponds to a substitution of I24K in SEQ ID NO: 1.

8. The method of claim 2 wherein the nucleotide corresponding to position −3 of the I-CreI meganuclease recognition site of SEQ ID NO: 4 has been altered to a C and the first specificity-altering amino acid modification corresponds to a substitution of I24R in SEQ ID NO: 1.

9. The method of claim 2 wherein the nucleotide corresponding to position −3 of the I-CreI meganuclease recognition site of SEQ ID NO: 4 has been altered to a T and the first specificity-altering amino acid modification corresponds to a substitution of R68M in SEQ ID NO: 1.

10. The method of claim 2 wherein the nucleotide corresponding to position −3 of the I-CreI meganuclease recognition site of SEQ ID NO: 4 has been altered to a T and the first specificity-altering amino acid modification corresponds to a substitution of R68C in SEQ ID NO: 1.

11. The method of claim 2 wherein the nucleotide corresponding to position −3 of the I-CreI meganuclease recognition site of SEQ ID NO: 4 has been altered to a T and the first specificity-altering amino acid modification corresponds to a substitution of R68L in SEQ ID NO: 1.

12. The method of claim 2 wherein the nucleotide corresponding to position −3 of the I-CreI meganuclease recognition site of SEQ ID NO: 4 has been altered to a T and the first specificity-altering amino acid modification corresponds to a substitution of R68F in SEQ ID NO: 1.

13. The method of claim 2 wherein the nucleotide corresponding to position −3 of the I-CreI meganuclease recognition site of SEQ ID NO: 4 has been altered to a T and the first specificity-altering amino acid modification corresponds to a substitution of R68Y in SEQ ID NO: 1.

14. The method of claim 2 wherein the nucleotide corresponding to position −3 of the I-CreI meganuclease recognition site of SEQ ID NO: 4 has been altered to a T and the first specificity-altering amino acid modification corresponds to a substitution of R68K in SEQ ID NO: 1.

15. The method of claim 2 wherein said cell is a plant cell.

16. The method of claim 15 wherein said nucleic acid is introduced into said cell by an *Agrobacterium* vector.

17. The method of claim 15 wherein said cell is a protoplast and said nucleic acid is introduced into said cell by PEG-mediated transformation.

18. The method of claim 15 wherein said nucleic acid is introduced into said cell by a method selected from the group consisting of ballistic injection and microprojectile bombardment.

19. The method of claim 15 wherein said nucleic acid is introduced into said cell by electroporation.

20. The method of claim 2 wherein said cell is a mammalian cell.

21. The method of claim 20 wherein the nucleic acid is introduced into said cell by an adenovirus or adeno-associated virus vector.

22. The method of claim 20 wherein the nucleic acid is introduced into said cell by microinjection.

23. The method of claim 20 wherein the nucleic acid is introduced into said cell by a method selected from the group consisting of ballistic injection and microprojectile bombardment.

24. The method of claim 20 wherein the nucleic acid is introduced into said cell by electroporation.

25. The method of claim 20 wherein the nucleic acid is introduced into said cell by liposome transfection.

* * * * *

(12) EX PARTE REEXAMINATION CERTIFICATE (10162nd)
United States Patent
Smith et al.

(10) Number: US 8,143,015 C1
(45) Certificate Issued: May 14, 2014

(54) METHODS OF CLEAVING DNA WITH RATIONALLY-DESIGNED MEGANUCLEASES

(75) Inventors: James Jefferson Smith, Durham, NC (US); Derek Jantz, Durham, NC (US); Homme W. Hellinga, Durham, NC (US)

(73) Assignee: Duke University, Durham, NC (US)

Reexamination Request:
No. 90/012,704, Oct. 15, 2012

Reexamination Certificate for:
Patent No.: 8,143,015
Issued: Mar. 27, 2012
Appl. No.: 13/245,650
Filed: Sep. 26, 2011

Related U.S. Application Data

(63) Continuation of application No. 13/223,852, filed on Sep. 1, 2011, now abandoned, which is a continuation of application No. 11/583,368, filed on Oct. 18, 2006, now Pat. No. 8,021,867.

(60) Provisional application No. 60/727,512, filed on Oct. 18, 2005.

(51) Int. Cl.
*C12Q 1/34* (2006.01)
*C07K 14/00* (2006.01)
*C12N 9/16* (2006.01)
*C12P 21/00* (2006.01)
*C12N 15/90* (2006.01)
*C12N 9/22* (2006.01)

(52) U.S. Cl.
CPC ............... *C12N 15/902* (2013.01); *C12N 9/22* (2013.01)
USPC ............ 435/18; 435/196; 435/6.1; 435/69.1; 530/350

(58) Field of Classification Search
None
See application file for complete search history.

(56) References Cited

To view the complete listing of prior art documents cited during the proceeding for Reexamination Control Number 90/012,704, please refer to the USPTO's public Patent Application Information Retrieval (PAIR) system under the Display References tab.

*Primary Examiner* — Shri Ponnaluri

(57) ABSTRACT

Rationally-designed LAGLIDADG meganucleases and methods of making such meganucleases are provided. In addition, methods are provided for using the meganucleases to generate recombinant cells and organisms having a desired DNA sequence inserted into a limited number of loci within the genome, as well as methods of gene therapy, for treatment of pathogenic infections, and for in vitro applications in diagnostics and research.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-25 is confirmed.

\* \* \* \* \*